United States Patent
Daly et al.

(10) Patent No.: US 10,632,194 B2
(45) Date of Patent: *Apr. 28, 2020

(54) ANTI-ERBB3 ANTIBODIES AND USES THEREOF

(71) Applicant: Regeneron Pharmaceuticals, Inc., Tarrytown, NY (US)

(72) Inventors: Christopher Daly, New York, NY (US); Douglas MacDonald, New York, NY (US); Xunbao Duan, Horsham, PA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 114 days.

This patent is subject to a terminal disclaimer.

(21) Appl. No.: 15/793,756

(22) Filed: Oct. 25, 2017

(65) Prior Publication Data

US 2018/0036406 A1 Feb. 8, 2018

Related U.S. Application Data

(60) Continuation of application No. 15/011,978, filed on Feb. 1, 2016, now Pat. No. 9,827,310, which is a continuation of application No. 14/308,527, filed on Jun. 18, 2014, now Pat. No. 9,284,380, which is a division of application No. 13/623,885, filed on Sep. 21, 2012, now Pat. No. 8,791,244.

(60) Provisional application No. 61/541,312, filed on Sep. 30, 2011, provisional application No. 61/557,460, filed on Nov. 9, 2011, provisional application No. 61/614,565, filed on Mar. 23, 2012.

(51) Int. Cl.
| | |
|---|---|
| *C07K 16/28* | (2006.01) |
| *C07K 16/30* | (2006.01) |
| *A61K 39/395* | (2006.01) |
| *C07K 16/32* | (2006.01) |
| *A61K 31/517* | (2006.01) |
| *A61K 31/5377* | (2006.01) |
| *C07K 16/40* | (2006.01) |
| *A61K 39/00* | (2006.01) |

(52) U.S. Cl.
CPC ...... *A61K 39/39558* (2013.01); *A61K 31/517* (2013.01); *A61K 31/5377* (2013.01); *A61K 39/3955* (2013.01); *C07K 16/2863* (2013.01); *C07K 16/3023* (2013.01); *C07K 16/3046* (2013.01); *C07K 16/3053* (2013.01); *C07K 16/32* (2013.01); *C07K 16/40* (2013.01); *A61K 2039/505* (2013.01); *A61K 2039/507* (2013.01); *C07K 2317/21* (2013.01); *C07K 2317/34* (2013.01); *C07K 2317/56* (2013.01); *C07K 2317/565* (2013.01); *C07K 2317/73* (2013.01); *C07K 2317/76* (2013.01); *C07K 2317/77* (2013.01); *C07K 2317/92* (2013.01)

(58) Field of Classification Search
CPC .......... A61K 39/3955; A61K 39/39558; A61K 2039/505; A61K 2039/507
See application file for complete search history.

(56) References Cited

U.S. PATENT DOCUMENTS

| | | | |
|---|---|---|---|
| 4,943,533 A | 7/1990 | Mendelsohn et al. | |
| 5,480,968 A | 1/1996 | Kraus et al. | |
| 5,844,093 A | 12/1998 | Kettleborough et al. | |
| 5,916,755 A | 6/1999 | Kraus et al. | |
| 5,968,511 A | 10/1999 | Akita et al. | |
| 7,060,808 B1 | 6/2006 | Goldstein et al. | |
| 7,153,828 B2 | 12/2006 | Sliwkowski et al. | |
| 7,247,301 B2 | 7/2007 | van de Winkel et al. | |
| 7,332,580 B2 | 2/2008 | Adams et al. | |
| 7,332,585 B2 | 2/2008 | Adams et al. | |
| 7,595,378 B2 | 9/2009 | van de Winkel et al. | |
| 7,662,374 B2 | 2/2010 | Greene et al. | |
| 7,705,130 B2 | 4/2010 | Rothe et al. | |
| 7,723,484 B2 | 5/2010 | Beidler et al. | |
| 7,846,440 B2 | 12/2010 | Schoeberl et al. | |
| 7,939,072 B2 | 5/2011 | Yarden et al. | |
| 8,791,244 B2 | 7/2014 | Daly et al. | |
| 9,101,760 B2 * | 8/2015 | Hettmann | A61K 39/39558 |
| 9,273,143 B2 * | 3/2016 | Daly | C07K 16/32 |
| 9,284,380 B2 * | 3/2016 | Daly | C07K 16/32 |
| 9,827,310 B2 * | 11/2017 | Daly | C07K 16/32 |
| 2004/0082510 A1 | 4/2004 | Ullrich et al. | |

(Continued)

FOREIGN PATENT DOCUMENTS

| | | |
|---|---|---|
| EP | 1053009 B1 | 9/2004 |
| EP | 0896586 B1 | 10/2006 |

(Continued)

OTHER PUBLICATIONS

Arteaga et al., "ERBB Receptors: From Oncogene Discovery to Basic Science to Mechanism-Based Cancer Therapeutics," Cancer Cell, 25:282-303, (2014).

(Continued)

*Primary Examiner* — Hong Sang

(74) *Attorney, Agent, or Firm* — Schwabe, Williamson & Wyatt PC; Lisa Dornbach Flanagan

(57) ABSTRACT

The present invention provides antibodies that bind to ErbB3 and methods of using same. According to certain embodiments of the invention, the antibodies are fully human antibodies that bind to human ErbB3. In certain embodiments, the antibodies of the present invention block the interaction of ErbB3 with an ErbB3 ligand such as neuregulin 1. The antibodies of the invention are useful for the treatment of various cancers.

8 Claims, No Drawings

Specification includes a Sequence Listing.

(56) References Cited

U.S. PATENT DOCUMENTS

| | | |
|---|---|---|
| 2004/0197332 A1 | 10/2004 | Ullrich et al. |
| 2007/0258984 A1 | 11/2007 | Fyfe et al. |
| 2008/0274114 A1 | 11/2008 | Beidler et al. |
| 2009/0123476 A1 | 5/2009 | Elvin et al. |
| 2010/0183631 A1 | 7/2010 | Rothe et al. |
| 2010/0184766 A1 | 7/2010 | Kunzer et al. |
| 2010/0266584 A1 | 10/2010 | Schoeberl et al. |
| 2010/0310557 A1 | 12/2010 | Keyt et al. |
| 2011/0033482 A1 | 2/2011 | Ullrich et al. |
| 2011/0123523 A1 | 5/2011 | Schoeberl et al. |
| 2011/0217237 A1 | 9/2011 | Chen et al. |
| 2011/0229406 A1 | 9/2011 | Hettmann et al. |
| 2013/0344093 A1 | 12/2013 | Daly et al. |

FOREIGN PATENT DOCUMENTS

| | | |
|---|---|---|
| EP | 1414494 B1 | 3/2009 |
| EP | 1355658 B1 | 3/2011 |
| WO | 97/035885 A1 | 10/1997 |
| WO | 03/013602 A1 | 2/2003 |
| WO | 04/008099 A2 | 1/2004 |
| WO | 05/079434 A2 | 9/2005 |
| WO | 07/077028 A2 | 7/2007 |
| WO | 08/100624 A2 | 8/2008 |
| WO | 10/019952 A2 | 2/2010 |
| WO | 10/085845 A1 | 8/2010 |
| WO | 10/108127 A1 | 9/2010 |
| WO | 11/022727 A2 | 2/2011 |
| WO | 11/044311 A2 | 4/2011 |
| WO | 11/056997 A1 | 5/2011 |
| WO | 11/076683 A1 | 6/2011 |
| WO | 11/112953 A2 | 9/2011 |
| WO | 11/136911 A2 | 11/2011 |
| WO | 12/019024 A2 | 2/2012 |
| WO | 12/022814 A1 | 2/2012 |
| WO | 13/048883 A2 | 4/2013 |
| WO | 14/004427 A2 | 1/2014 |

OTHER PUBLICATIONS

Aurisicchio et al., "Novel Anti-ErbB3 monoclonal antibodies show therapeutic efficacy in xenografted and spontaneous mouse tumors," J. Cellular Physiol., 227(10):3381-3388, (2011).

Aurisicchio et al., "The promise of anti-ErbB3 monoclonals as new cancer therapeuticals," Oncotarget, 3(8):744-758, (2012).

Bendig, "Humanization of Rodent Monoclonal Antibodies by CDR Grafting," Methods: A Companion to Methods in Enzymology, 8:83-93, (1995).

Bonner et al., "Radiotherapy plus Cetuximab for Squamous-Cell Carcinoma of the Head and Neck," N Engl J Med, 354:567-578, (2006). [Retrieved from the Internet Jun. 24, 2013: <URL: http://nejm.org>].

Cai et al., "Differential binding patterns of monoclonal antibody 2C4 to the ErbB3-p185her2/neu and the EGFR-p185her2/neu complexes," Oncogene, 27(27):3870, doi:10.1038/onc.2008.13, 9 pages, (2008).

Capdevila et al., "Anti-Tumour Treatment: Anti-epidermal growth factor receptor monoclonal antibodies in cancer treatment," Cancer Treatment Reviews, 35:354-363, (2009).

Carter et al., "Identification and validation of cell surface antigens for antibody targeting in oncology," Endocrine-Related Cancer, 11:659-687, (2004).

Cho et al., "Structure of the Extracellular Region of HER3 Reveals an Interdomain Tether," Science 297:1330-1333, doi:10.1126/science.1074611, (2002).

Cimini et al., "Innovative Therapies against Human Glioblastoma Multiforme," ISRN Oncol., 2011:787490, Epub, doi: 10.5402/2011/787490, (2011). Abstract only. [Retrieved from the Internet Sep. 10, 2015: <URL: http://www.ncbi.nlm.nih.gov/pubmed/22091432>].

Colman, "Effects of amino acid sequence changes on antibody-antigen interactions," Research in Immunology, 145:33-36, (1994).

Cook et al., "ErbB3 Ablation Impairs PI3K/Akt-Dependent Mammary Tumorigenesis," Cancer Res, 71:3941-3951, (2011).

Cunningham et al., "Cetuximab Monotherapy and Cetuximab plus Irinotecan in Irinotecan-Refractory Metastatic Colorectal Cancer," N Engl J Med, 351:337-345, (2004). [Retrieved from the Internet Jun. 24, 2013: <URL: http://nejm.org>].

Franklin et al., "Insights into ErbB signaling from the structure of the ErbB2-pertuzumab complex," Cancer Cell, 5:317-328, (2004).

Gajadhar et al., "In Situ Analysis of Mutant EGFRs Prevalent in Glioblastoma Multiforme Reveals Aberrant Dimerization, Activation, and Differential Response to Anti-EGFR Targeted Therapy," Mol Cancer Res, 10(3):428-440, (2012). [Retrieved from the Internet Mar. 6, 2014: <URL: http://mcr.aacrjournals.org/>].

Goffin et al., "Epidermal Growth Factor Receptor: Pathway, Therapies, and Pipeline," Clinical Therapeutics, 35(9):1282-1303 (2013).

Hubbard, "EGF receptor inhibition: Attacks on multiple fronts," Cancer Cell, 7:287-288. (2005).

Hynes et al., "ERBB Receptors and Cancer: the Complexity of Targeted Inhibitors," Nat. Rev. Cancer, 5:341-354, (2005).

Jaiswal et al., "Oncogenic ERBB3 Mutations in Human Cancers," Cancer Cell, 23:603-617, (2013).

Jathal et al., "Targeting ErbB3: the New RTK(id) on the Prostate Cancer Block," Immunol. Endocr. Metab. Agents Med. Chem., 11(2):131-149, (2011).

Kamath et al., "Preclinical pharmacokinetics of MEHD7945A, a novel EGFR/ HER3 dual-action antibody, and prediction of its human pharmacokinetics and efficacious clinical dose," Cancer Chemother Pharmacol, doi:10.1007/s00280-011-1806-6, 7 pages, (2011).

Leung, K., "44-[18F]Fluorobenzoyl-Phe-Ala-Leu-Gly-Glu-Ala-NH2," Molecular Imaging and Contrast Agent Database (MICAD), National Center for Biotechnology Information (US), (2011). Excerpt Only. [Retrieved from the Internet Sep. 10, 2015: <URL: http://www.ncbi.nlm.nih.gov/pubmed/22171398>].

Lin et al., "Soluble ErbB3 Levels in Bone Marrow and Plasma of Men with Prostate Cancer," Clin. Cancer Res., 14:3729-3736, (2008).

Paul, "Fundamental Immunology, 3rd Edition," Raven Press, Ltd., ISBN 0-7817-0022-1, pp. 292-295, (1993).

Robinson et al., "Targeting ErbB2 and ErbB3 with a bispecific single-chain Fv enhances targeting selectivity and induces a therapeutic effect in vitro," Br. J. Cancer, 99(9):1415-1425, (2008).

Rudikoff et al., "Single amino acid substitution altering antigen-binding specificity," Proc. Natl. Acad. Sci. USA, 79(6):1979-1983, (1982).

Sala et al., "An ErbB-3 antibody, MP-RM-1, inhibits tumor growth by blocking ligand-dependent and independent activation of ErbB-3/Akt signaling," Oncogene, 31:1275-1286, (2011).

Schaefer et al., "A Two-in-One Antibody against HER3 and EGFR Has Superior Inhibitory Activity Compared with Monospecific Antibodies," Cancer Cell, 20:472-486, (2011).

Schoeberl et al., "An ErbB3 antibody, MM-121, is active in cancers with ligand-dependent activation," Cancer Res., 70(6):2485-2494, (2010).

Sergina et al., "Escape from HER-family tyrosine kinase inhibitor therapy by the kinase-inactivated HER3," Nature, 445:437-441, (2007).

Takeuchi et al., "Target Therapy for Cancer: Anti-cancer Drugs Targeting Growth-Factor Signaling Molecules," Biol. Pharm. Bull., 34(12):1774-1780, (2011).

Tanaka et al., "Oncogenic EGFR signaling activates an mTORC2-NF-KB pathway that promotes chemotherapy resistance," Cancer Discov, (6):524-638, (2011). Abstract Only. [Retrieved from the Internet Sep. 10, 2015: <URL: http://www.ncbi.nlm.nih.gov/pubmed/22145100>].

Tebbutt et al., "Targeting the ERBB family in cancer: couples therapy," Nature Reviews, Cancer, 13:663-673, (2013).

U.S. Appl. No. 13/623,885, Non-Final Office Action dated Oct. 31, 2013.

U.S. Appl. No. 13/623,885, Notice of Allowance and Examiner Initiated Interview Summary dated Mar. 20, 2014.

U.S. Appl. No. 13/623,885, Requirement for Restriction/Election dated Aug. 21, 2013.

(56) References Cited

OTHER PUBLICATIONS

U.S. Appl. No. 14/082,780, Non-Final Office Action dated Jun. 26, 2015.
U.S. Appl. No. 14/082,780, Notice of Allowance and Examiner-Initiated Interview Summary dated Oct. 26, 2015.
U.S. Appl. No. 14/308,527, Non-Final Office Action dated Jun. 25, 2015.
U.S. Appl. No. 14/308,527, Notice of Allowance and Examiner-Initiated Interview Summary dated Oct. 30, 2015.
U.S. Appl. No. 15/011,978, Non-Final Office Action dated Mar. 22, 2017.
U.S. Appl. No. 15/011,978, Notice of Allowance dated Jul. 25, 2017.
Van Cutsem et al., "Cetuximab and Chemotherapy as Initial Treatment for Metastatic Colorectal Cancer," N Engl J Med, 360(14):1408-1417, (2009). [Retrieved from the Internet Jun. 24, 2013: <URL: http://nejm.org>].
Van Der Horst et al., "Anti-Her-3 MAbs inhibit HER-3-mediated signaling in breast cancer cell lines resistant to anti-HER-2 antibodies," Int. J. Cancer, 115(4):519-527, (2005).
Wang et al., "Genetically Dependent ERBB3 Expression Modulates Antigen Presenting Cell Function and Type 1 Diabetes Risk," PLoS ONE, 5(7):e11789, doi:10.1371/journal.pone.0011789, 10 pages, (2010).
WIPO Application No. PCT/US2012/056446, PCT International Search Report dated May 7, 2013.
WIPO Application No. PCT/US2012/056446, PCT Written Opinion of the International Searching Authority dated May 7, 2013.
Zhang et al., "REGN1400, a fully-human ERBB3 antibody, potently inhibits tumor growth in preclinical models, both as a monotherapy and in combination with EGFR or HER2 blockers," Cancer Res., 72(8), suppl 1, Abstract No. 2718, (2012).

\* cited by examiner

ANTI-ERBB3 ANTIBODIES AND USES THEREOF

CROSS-REFERENCE TO RELATED APPLICATIONS

This application is a continuation of U.S. application Ser. No. 15/011,978, filed Feb. 1, 2016, now U.S. Pat. No. 9,827,310, which is a continuation of U.S. application Ser. No. 14/308,527, filed Jun. 18, 2014, now U.S. Pat. No. 9,284,380, which is a division of U.S. application Ser. No. 13/623,885, filed Sep. 21, 2012, now U.S. Pat. No. 8,791,244, which claims the benefit under 35 USC § 119(e) of U.S. Provisional Application Nos. 61/541,312, filed on Sep. 30, 2011; 61/557,460, filed on Nov. 9, 2011; and 61/614,565, filed on Mar. 23, 2012, the disclosures of which are herein incorporated by reference in their entireties.

REFERENCE TO A SEQUENCE LISTING

This application includes an electronic sequence listing in a file named "230247-Sequence.txt", created on Oct. 25, 2017 and containing 184,064 bytes, which is hereby incorporated by reference in its entirety for all purposes.

FIELD OF THE INVENTION

The present invention relates to antibodies, and antigen-binding fragments thereof, which are specific for human ErbB3.

BACKGROUND

ErbB3 (also known as HER3) is a member of the ErbB/HER family of receptor tyrosine kinases (RTKs). Other members of this family include EGFR (also known as ErbB1 or HER1), ErbB2 (also known as HER2 or Neu), and HER4. ErbB receptors regulate cell proliferation, survival and differentiation by activating intracellular signaling cascades that lead to alterations in gene expression.

ErbB receptors are activated by the formation of either homo- or heterodimers. For example, when ErbB3 is co-expressed with ErbB2, an active heterodimeric signaling complex is formed. ErbB3 dimer formation is promoted by its ligand binding. Neuregulin 1 (NRG1) is the primary ligand for ErbB3 that promotes homo- or heterodimerization of the receptor.

ErbB3 has been found to be overexpressed in various cancer types, including breast, gastrointestinal, and pancreatic cancers. Anti-ErbB3 antibodies have been shown to inhibit the growth of several human tumor cell lines in mouse xenografts models. Anti-ErbB3 antibodies are mentioned in, e.g., U.S. Pat. Nos. 5,480,968; 5,968,511; US 2004/0197332; U.S. Pat. Nos. 7,332,580; 7,705,130; and 7,846,440. Nonetheless, there is a need in the art for novel ErbB3 antagonists, such as anti-ErbB3 antibodies, for the treatment of cancer and other related disorders.

BRIEF SUMMARY OF THE INVENTION

The present invention provides antibodies that bind human ErbB3. The antibodies of the invention are useful, inter alia, for inhibiting ErbB3-mediated signaling and for treating diseases and disorders caused by or related to ErbB3 activity and/or signaling.

The antibodies of the present invention, according to certain embodiments, block the interaction between ErbB3 and an ErbB3 ligand (e.g., NRG1 and/or NRG2). The antibodies may also possess one or more additional biological properties such as, e.g., inducing cell surface ErbB3 internalization, inhibiting NRG1-stimulated tumor growth in vitro, and/or inhibiting tumor growth in vivo.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, J. Immunol. 164:1925-1933).

The present invention provides an antibody or antigen-binding fragment of an antibody comprising a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466 and 482, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474 and 490, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/458, 466/474 and 482/490.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 472 and 488 or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 464, 480 and 496, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, 376/384, 392/400, 408/416, 424/432, 440/448, 456/464, 472/480 and 488/496.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 468 and 484, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 470 and 486, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 460, 476 and 492, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 462, 478 and 494, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H4H2084P); 20-22-24-28-30-32 (e.g. H4H2092P); 36-38-40-44-46-48 (e.g. H4H2094P); 52-54-56-60-62-64 (e.g. H4H2098P); 68-70-72-76-78-80 (e.g. H4H2102P); 84-86-88-92-94-96 (e.g. H4H2108P); 100-102-104-108-110-112 (e.g. H4H2111P); 116-118-120-124-126-128 (e.g. H4H2114P); 132-134-136-140-142-144 (e.g. H4H2132P); 148-150-152-156-158-160 (e.g., H4H2138P); 164-166-168-172-174-176 (e.g. H4H2140P); 180-182-184-188-190-192 (e.g., H4H2143P); 196-198-200-204-206-208 (e.g. H4H2146P); 212-214-216-220-222-224 (e.g. H4H2147P); 228-230-232-236-238-240 (e.g. H4H2148P); 244-246-248-252-254-256 (e.g. H4H2151P); 260-262-264-268-270-272 (e.g. H4H2153P); 276-278-280-284-286-288 (e.g. H4H2154P); 292-294-296-300-302-304 (e.g. H4H2290P); 308-310-312-316-318-320 (e.g. H1M1819N); 324-326-328-332-334-336 (e.g. H2M1821N); 340-342-344-348-350-352 (e.g. H2M1824N); 356-358-360-364-366-368 (e.g. H2M1827N); 372-374-376-380-382-384 (e.g. H1M1828N); 388-390-392-396-398-400 (e.g. H2M1829N); 404-406-408-412-414-416 (e.g. H2M1930N); 420-422-424-428-430-432 (e.g. H2M1943N); 436-438-440-444-446-448 (e.g. H2M1936N); 452-454-456-460-462-464 (e.g. H2M1937N); 468-470-472-476-478-480 (e.g. H2M1938N); and 484-486-488-492-494-496 (e.g. H1M1940N).

In a related embodiment, the invention includes an antibody or antigen-binding fragment of an antibody which specifically binds ErbB3, wherein the antibody or fragment comprises the heavy and light chain CDR domains contained within heavy and light chain sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/458, 466/474 and 482/490. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-ErbB3 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337, 353, 369, 385, 401, 417, 433, 449, 465 and 481, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, 377, 393, 409, 425, 441, 457, 473 and 489, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343, 359, 375, 391, 407, 423, 439, 455, 471 and 478, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, 383, 399, 415, 431, 447, 463, 479 and 495, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, 371, 387, 403, 419, 435, 451, 467 and 483 or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341, 357, 373, 389, 405, 421, 437, 453, 469 and 485, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, 379, 395, 411, 427, 443, 459, 475 and 491, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349, 365, 381, 397, 413, 429, 445, 461, 477 and 493, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: SEQ ID NOs: 1 and 9 (e.g. H4H2084P), 17 and 25 (e.g. H4H2092P), 33 and 41 (e.g. H4H2094P), 49 and 57 (e.g. H4H2098P), 65 and 73 (e.g. H4H2102P), 81 and 89 (e.g. H4H2108P), 97 and 105 (e.g. H4H2111P), 113 and 121 (e.g. H4H2114P), 129 and 137 (e.g. H4H2132P), 145 and 153 (e.g. H4H2138P), 161 and 169 (e.g. H4H2140P), 177 and 185 (e.g. H4H2143P), 193 and 201 (e.g. H4H2146P), 209 and 217 (e.g. H4H2147P), 225 and 233 (e.g. H4H2148P), 241 and 249 (e.g. H4H2151P), 257 and 265 (e.g. H4H2153P), 273 and 281 (e.g. H4H2154P), 289 and 297 (e.g. H4H2290P), 305 and 313 (e.g. H1M1819N), 321 and 329 (e.g. H2M1821N), 337 and 345 (e.g. H2M1824N), 353 and 361 (e.g. H2M1827N), 369 and 377 (e.g. H1M1828N), 385 and 393 (e.g. H2M1829N), 401 and 409 (e.g. H2M1930N), 417 and 425 (e.g. H2M1934N), 433 and 441 (e.g. H2M1936N), 449 and 457 (e.g. H2M1937N), 465 and 473 (e.g. H2M1938N), or 481 and 489 (e.g. H1M1940N).

The present invention includes anti-ErbB3 antibodies having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds ErbB3 and a pharmaceutically acceptable carrier. In a related aspect, the invention features a composition which is a combination of an ErbB3 inhibitor and a second therapeutic agent. In one embodiment, the ErbB3 inhibitor is an antibody or fragment thereof. In one embodiment, the second therapeutic agent is any agent that is advantageously combined with an ErbB3 inhibitor. Exemplary agents that may be advantageously combined with an ErbB3 inhibitor include, without limitation, other agents that inhibit ErbB3 activity (including other antibodies or antigen-binding fragments thereof, peptide inhibitors, small molecule antagonists, etc) and/or agents which interfere with ErbB3 upstream or downstream signaling.

In yet another aspect, the invention provides methods for inhibiting ErbB3 activity using an anti-ErbB3 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of ErbB3 activity. The anti-ErbB3 antibody or antibody fragment of the invention may function to block the interaction between ErbB3 and an ErbB3 binding partner (e.g., neuregulin-1), or otherwise inhibit the signaling activity of ErbB3.

The present invention also includes the use of an anti-ErbB3 antibody or antigen binding portion of an antibody of the invention in the manufacture of a medicament for the treatment of a disease or disorder related to or caused by ErbB3 activity in a patient.

Other embodiments will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "ErbB3" and "ErbB3 fragment," as used herein refer to the human ErbB3 protein or fragment unless specified as being from a non-human species (e.g., "mouse ErbB3," "mouse ErbB3 fragment," "monkey ErbB3," "monkey ErbB3 fragment," etc.). The extracellular domain of human ErbB3 has the amino acid sequence shown in, e.g., amino acids 1-613 of SEQ ID NOs:497-499.

The term "ErbB3 ligand," as used herein, means a protein capable of binding to the extracellular domain of human ErbB3 protein to transmit a biological signal in vivo. The term "ErbB3 ligand" includes neuregulin-1 (NRG1) and neuregulin-2 (NRG2).

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-ErbB3 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; $V_H$—$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" human ErbB3, as used in the context of the present invention, includes antibodies that bind human ErbB3 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. (See, e.g., Example 3, herein). An isolated antibody that specifically binds human ErbB3 may, however, have cross-reactivity to other antigens, such as ErbB3 molecules from other (non-human) species.

A "neutralizing" or "blocking" antibody, as used herein, is intended to refer to an antibody whose binding to ErbB3: (i) interferes with the interaction between ErbB3 or an ErbB3 fragment and an ErbB3 ligand (e.g., neuregulin 1), and/or (ii) results in inhibition of at least one biological function of ErbB3. The inhibition caused by an ErbB3 neutralizing or blocking antibody need not be complete so long as it is detectable using an appropriate assay. Exemplary assays for detecting ErbB3 inhibition are described herein.

The anti-ErbB3 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-ErbB3 antibodies comprising variants of any of the HCVR, LCVR, and/or CDR amino acid sequences disclosed herein having one or more conservative substitutions. For example, the present invention includes anti-ErbB3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Biological Characteristics of the Antibodies

The antibodies of the present invention block the interaction between ErbB3 and its ligand neuregulin-1 (NRG1). As used herein, the expression "blocks the interaction between ErbB3 and NRG1" means that, in an assay in which the physical interaction between ErbB3 and NRG1 can be detected and/or quantified, the addition of an antibody of the invention reduces the interaction between ErbB3 and NRG1 by at least 50%. A non-limiting, exemplary assay that can be used to determine if an antibody blocks the interaction between human ErbB3 and NRG1 is illustrated in Example 4, herein. In this Example, antibodies are mixed with ErbB3 protein, and then the antibody/ErbB3 mixture is applied to a surface coated with NRG1 protein. After washing away unbound molecules, the amount of ErbB3 bound to the NRG1-coated surface is measured. By using varying amounts of antibody in this assay format, the amount of antibody required to block 50% of ErbB3 binding to NRG1 can be calculated and expressed as an $IC_{50}$ value. The present invention includes anti-ErbB3 antibodies that exhibit an $IC_{50}$ of less than about 600 pM when tested in an ErbB3/NRG1 binding assay as described above, or a substantially similar assay. For example, the invention includes anti-ErbB3 antibodies that exhibit an $IC_{50}$ of less than about 600, 500, 400, 300, 290, 280, 270, 260, 250, 240, 230, 220, 210, 200, 190, 180, 170, 160, 150, 140, 130, 120, 110, 100, 90, 80, 70, 60, 50, 40, 30, 20, 10, 18, 16, 14, 12, 10, 9, 8, 7, 6, 5, 4, 3, 2, or 1 pM when tested in an ErbB3/NRG1 binding assay as described above, or a substantially similar assay.

Alternatively, one can determine whether an antibody blocks the interaction between ErbB3 and NRG1 by using a cell-based assay format that detects changes in NRG1-induced cellular signaling. Exemplary assay formats of this type are illustrated in Examples 6 and 8, herein. In these Examples, the extent of phosphorylation of the kinase Akt and/or ErbB3 in cells following treatment with NRG1 in the presence of varying amounts of anti-ErbB3 antibody is measured. In these assay formats, the percent inhibition of Akt and/or ErbB3 phosphorylation caused by the presence of an anti-ErbB3 antibody serves as an indicator of the extent to which the antibody blocks the interaction between ErbB3 and NRG1. The present invention includes antibodies that inhibit Akt or ErbB3 phosphorylation by at least 60% when tested in an Akt or ErbB3 phosphorylation assay as described above, or a substantially similar assay. For example, the invention includes anti-ErbB3 antibodies that inhibit Akt or ErbB3 phosphorylation by at least about 60%, 65%, 70%, 75%, 80%, 85%, 90%, 95%, or 100% when tested in an Akt or ErbB3 phosphorylation assay as described above, or a substantially similar assay.

The anti-ErbB3 antibodies of the present invention also exhibit one or more of the following properties: (1) the ability to induce internalization of cell surface expressed ErbB3 (see, e.g., Example 5, herein); (2) the ability to inhibit NRG1-stimulated tumor cell growth in vitro, either alone or in combination with EGFR inhibition (see, e.g., Example 7, herein); and (3) the ability to inhibit tumor growth in animals (see, e.g., Example 9, herein).

Epitope Mapping and Related Technologies

The ErbB3 protein, like all ErbB/HER family members, contains four extracellular domains, referred to as "Domain I," "Domain II," "Domain III," and "Domain IV." Domain I is the sequence of amino acids represented by amino acids 1 through 190 of SEQ ID NO:498; Domain II is the sequence of amino acids represented by amino acids 191 through 308 of SEQ ID NO:498; Domain III is the sequence of amino acids represented by amino acids 309 through 499 of SEQ ID NO:498; and Domain IV is the sequence of amino acids represented by amino acids 500 through 624 of SEQ ID NO:498.

The present invention includes anti-ErbB3 antibodies which interact with one or more epitopes found within Domain III of the extracellular domain of ErbB3. The epitope(s) may consist of one or more contiguous sequences of 3 or more (e.g., 3, 4, 5, 6, 7, 8, 9, 10, 11, 12, 13, 14, 15, 16, 17, 18, 19, 20 or more) amino acids located within Domain III of ErbB3. Alternatively, the epitope may consist of a plurality of non-contiguous amino acids (or amino acid sequences) located within Domain III of ErbB3. According to certain embodiments of the present invention, anti-ErbB3 antibodies are provided which interact with one or more amino acids located within one or more Domain III amino acid segments selected from the group consisting of amino acids 345-367 of SEQ ID NO:498, amino acids 423-439 of SEQ ID NO:498; and amino acids 451-463 of SEQ ID NO:498. For example, the present invention includes anti-ErbB3 antibodies which interact with at least one amino acid within each of the aforementioned Domain III amino acid segments (i.e., within each of amino acids 345-367, 423-439, and 451-463 of SEQ ID NO:498).

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. (See, e.g., Example 11 herein). In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-ErbB3 antibodies that bind to the same epitope as any of the specific exemplary antibodies described herein (e.g., H1M1819N, H2M1821N, H2M1824N, H2M1827N, H1M1828N, H2M1829N, H2M1930N, H2M1934N, H2M1938N, H1M1940N, etc.). Likewise, the present invention also includes anti-ErbB3 antibodies that compete for binding to ErbB3 or an ErbB3 fragment with any of the specific exemplary antibodies described herein (e.g., H1M1819N, H2M1821N, H2M1824N, H2M1827N, H1M1828N, H2M1829N, H2M1930N, H2M1934N, H2M1938N, H1M1940N, etc.).

One can easily determine whether an antibody binds to the same epitope as, or competes for binding with, a reference anti-ErbB3 antibody by using routine methods known in the art. For example, to determine if a test antibody binds to the same epitope as a reference anti-ErbB3 antibody of the invention, the reference antibody is allowed to bind to an ErbB3 protein or peptide under saturating conditions. Next, the ability of a test antibody to bind to the ErbB3 molecule is assessed. If the test antibody is able to bind to ErbB3 following saturation binding with the reference anti-ErbB3 antibody, it can be concluded that the test antibody binds to a different epitope than the reference anti-ErbB3 antibody. On the other hand, if the test antibody is not able to bind to the ErbB3 molecule following saturation binding with the reference anti-ErbB3 antibody, then the test antibody may bind to the same epitope as the epitope bound by the reference anti-ErbB3 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-ErbB3 antibody, the above-described binding methodology is performed in two orientations: In a first orientation, the reference antibody is allowed to bind to an ErbB3 molecule under saturating conditions followed by assessment of binding of the test antibody to the ErbB3 molecule. In a second orientation, the test antibody is allowed to bind to an ErbB3 molecule under saturating conditions followed by assessment of binding of the reference antibody to the ErbB3 molecule. If, in both orientations, only the first (saturating) antibody is capable of binding to the ErbB3 molecule, then it is concluded that the test antibody and the reference antibody compete for binding to ErbB3. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human ErbB3.

Using VELOCIMMUNE™ technology or any other known method for generating monoclonal antibodies, high affinity chimeric antibodies to ErbB3 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-ErbB3 antibodies and antibody fragments of the present invention encompass proteins having amino acid sequences that vary from those of the described antibodies but that retain the ability to bind human ErbB3. Such variant antibodies and antibody fragments comprise one or more additions, deletions, or substitutions of amino acids when compared to parent sequence, but exhibit biological activity that is essentially equivalent to that of the described antibodies. Likewise, the anti-ErbB3 antibody-encoding DNA sequences of the present invention encompass sequences that comprise one or more additions, deletions, or substitutions of nucleotides when compared to the disclosed sequence, but that encode an anti-ErbB3 antibody or antibody fragment that is essentially bioequivalent to an anti-ErbB3 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-ErbB3 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-ErbB3 antibody variants comprising amino acid changes which modify the glycosylation characteristics of the antibodies, e.g., mutations which eliminate or remove glycosylation.

Species Selectivity and Species Cross-Reactivity

According to certain embodiments of the invention, the anti-ErbB3 antibodies bind to human ErbB3 but not to ErbB3 from other species. The present invention also includes anti-ErbB3 antibodies that bind to human ErbB3 and to ErbB3 from one or more non-human species. For example, the anti-ErbB3 antibodies of the invention may bind to human ErbB3 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee ErbB3.

Immunoconjugates

The invention encompasses anti-ErbB3 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-ErbB3 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human ErbB3 or a fragment thereof, and the other arm of the immunoglobulin is specific for a second therapeutic target (e.g., EGFR, EGFRvIII, ErbB2/HER2, ErbB4, VEGF or Ang2) or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides pharmaceutical compositions comprising the anti-ErbB3 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with ErbB3 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-ErbB3 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by ErbB3 activity or treatable by blocking the interaction between ErbB3 and an ErbB3 ligand (e.g., NRG1). The antibodies and antigen-binding fragments of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the invention are used to treat one or more of the following cancers: renal cell carcinoma, pancreatic carcinoma, breast cancer, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer (e.g., EGFR-dependent non-small cell lung cancer), synovial sarcoma, thyroid cancer, or melanoma.

The present invention also provides methods for treating a tumor which is resistant to, or has become resistant to anti-EGFR or anti-HER2 therapy. For example, the present invention includes methods which comprise (a) identifying a patient having a tumor which is resistant, or has become resistant, to one or more of an anti-EGFR antibody (e.g., cetuximab), a small molecule inhibitor of EGFR (e.g., erlotinib), an anti-HER2 antibody (e.g. trastuzumab), and/or a small molecule inhibitor of HER2; and (b) administering to the patient an anti-ErbB3 antibody of the present invention, either alone, or in combination with an anti-EGFR antibody (e.g., cetuximab), a small molecule inhibitor of EGFR (e.g., erlotinib), an anti-HER2 antibody (e.g. trastuzumab), and/or a small molecule inhibitor of HER2. Combination therapies are discussed in more detail below.

Combination Therapies

The present invention includes therapeutic administration regimens which comprise administering an anti-ErbB3 antibody of the present invention in combination with at least one additional therapeutically active component. Non-limiting examples of such additional therapeutically active components include other ErbB3 antagonists (e.g., a second anti-ErbB3 antibody or small molecule inhibitor of ErbB3), an antagonist of ErbB2/HER2 (e.g., anti-HER2 antibody [e.g., trastuzumab] or small molecule inhibitor of HER2 activity), an antagonist of ErbB4 (e.g., anti-ErbB4 antibody or small molecule inhibitor of ErbB4 activity), an antagonist of epidermal growth factor receptor (EGFR) (e.g., anti-EGFR antibody [e.g., cetuximab or panitumumab] or small molecule inhibitor of EGFR activity [e.g., erlotinib or gefitinib]), an antagonist of EGFRvIII (e.g., an antibody that specifically binds EGFRvIII), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib), or an anti-DLL4 antibody (e.g., an anti-DLL4 antibody disclosed in US 2009/0142354 such as REGN421), etc.). Other agents that may be beneficially administered in combination with the anti-ErbB3 antibodies of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention also includes therapeutic combinations comprising any of the anti-ErbB3 antibodies mentioned herein and an inhibitor of one or more of VEGF, DLL4, EGFR, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The anti-ErbB3 antibodies of the invention may also be administered in combination with antivirals, antibiotics, analgesics, corticosteroids and/or NSAIDs. The anti-ErbB3 antibodies of the invention may also be administered as part of a treatment regimen that also includes radiation treatment and/or conventional chemotherapy. The additional therapeutically active component(s) may be administered prior to, concurrent with, or after the administration of an anti-ErbB3 antibody of the present invention; (for purposes of the present disclosure, such administration regimens are considered the administration of an anti-ErbB3 antibody "in combination with" a therapeutically active component of the invention).

Administration Regimens

According to certain embodiments of the present invention, multiple doses of an anti-ErbB3 antibody may be administered to a subject over a defined time course. The methods according to this aspect of the invention comprise sequentially administering to a subject multiple doses of an anti-ErbB3 antibody. As used herein, "sequentially administering" means that each dose of anti-ErbB3 antibody is administered to the subject at a different point in time, e.g., on different days separated by a predetermined interval (e.g., hours, days, weeks or months). The present invention includes methods which comprise sequentially administering to the patient a single initial dose of an anti-ErbB3 antibody, followed by one or more secondary doses of the anti-ErbB3 antibody, and optionally followed by one or more tertiary doses of the anti-ErbB3 antibody.

The terms "initial dose," "secondary doses," and "tertiary doses," refer to the temporal sequence of administration of the anti-ErbB3 antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-ErbB3 antibody, but generally may differ from one another in terms of frequency of administration. In certain embodiments, however, the amount of anti-ErbB3 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-ErbB3 antibody which is administered to a patient prior to the administration of the very next dose in the sequence with no intervening doses.

The methods according to this aspect of the invention may comprise administering to a patient any number of secondary and/or tertiary doses of an anti-ErbB3 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Any of the exemplary anti-ErbB3 antibodies disclosed herein may be used in the context of the foregoing administration regimens.

Diagnostic Uses of the Antibodies

The anti-ErbB3 antibodies of the present invention may also be used to detect and/or measure ErbB3 in a sample, e.g., for diagnostic purposes. For example, an anti-ErbB3 antibody, or fragment thereof, may be used to diagnose a condition or disease characterized by aberrant expression (e.g., over-expression, under-expression, lack of expression, etc.) of ErbB3. Exemplary diagnostic assays for ErbB3 may comprise, e.g., contacting a sample, obtained from a patient, with an anti-ErbB3 antibody of the invention, wherein the anti-ErbB3 antibody is labeled with a detectable label or reporter molecule. Alternatively, an unlabeled anti-ErbB3 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure ErbB3 in a sample include enzyme-linked immunosorbent assay (ELISA), radioimmunoassay (RIA), and fluorescence-activated cell sorting (FACS).

Samples that can be used in ErbB3 diagnostic assays according to the present invention include any tissue or fluid sample obtainable from a patient which contains detectable quantities of ErbB3 protein, or fragments thereof, under normal or pathological conditions. Generally, levels of ErbB3 in a particular sample obtained from a healthy patient (e.g., a patient not afflicted with a disease or condition associated with abnormal ErbB3 levels or activity) will be measured to initially establish a baseline, or standard, level of ErbB3. This baseline level of ErbB3 can then be compared against the levels of ErbB3 measured in samples obtained from individuals suspected of having a ErbB3 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human ErbB3

An immunogen comprising the ecto-domain of human ErbB3 was administered directly, with an adjuvant to stimulate the immune response, to a VELOCIMMUNE® mouse comprising DNA encoding human Immunoglobulin heavy and kappa light chain variable regions. The antibody immune response was monitored by a ErbB3-specific immunoassay. When a desired immune response was achieved splenocytes were harvested and fused with mouse myeloma cells to preserve their viability and form hybridoma cell lines. The hybridoma cell lines were screened and selected to identify cell lines that produce ErbB3-specific antibodies. Using this technique several anti-ErbB3 chimeric antibodies (i.e., antibodies possessing human variable domains and mouse constant domains) were obtained; exemplary antibodies generated in this manner were designated as follows: H1M1819N, H2M1821N, H2M1824N, H2M1827N, H1M1828N, H2M1829N, H2M1930N, H2M1934N, H2M1936N, H2M1937N, H2M1938N, and H1M1940N.

Anti-ErbB3 antibodies were also isolated directly from antigen-positive B cells without fusion to myeloma cells, as described in US 2007/0280945A1. Using this method, several fully human anti-ErbB3 antibodies (i.e., antibodies possessing human variable domains and human constant domains) were obtained; exemplary antibodies generated in this manner were designated as follows: H4H2084P, H4H2092P, H4H2094P, H4H2098P, H4H2102P, H4H2108P, H4H2111P, H4H2114P, H4H2132P, H4H2138P, H4H2140P, H4H2143P, H4H2146P, H4H2147P, H4H2148P, H4H2151P, H4H2153P, H4H2154P, and H4H2290P.

Certain biological properties of the exemplary anti-ErbB3 antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs of selected anti-ErbB3 antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 2084P | 2 | 4 | 6 | 8 | 10 | 12 | 14 | 16 |
| 2092P | 18 | 20 | 22 | 24 | 26 | 28 | 30 | 32 |
| 2094P | 34 | 36 | 38 | 40 | 42 | 44 | 46 | 48 |
| 2098P | 50 | 52 | 54 | 56 | 58 | 60 | 62 | 64 |
| 2102P | 66 | 68 | 70 | 72 | 74 | 76 | 78 | 80 |
| 2108P | 82 | 84 | 86 | 88 | 90 | 92 | 94 | 96 |
| 2111P | 98 | 100 | 102 | 104 | 106 | 108 | 110 | 112 |
| 2114P | 114 | 116 | 118 | 120 | 122 | 124 | 126 | 128 |
| 2132P | 130 | 132 | 134 | 136 | 138 | 140 | 142 | 144 |
| 2138P | 146 | 148 | 150 | 152 | 154 | 156 | 158 | 160 |
| 2140P | 162 | 164 | 166 | 168 | 170 | 172 | 174 | 176 |
| 2143P | 178 | 180 | 182 | 184 | 186 | 188 | 190 | 192 |
| 2146P | 194 | 196 | 198 | 200 | 202 | 204 | 206 | 208 |
| 2147P | 210 | 212 | 214 | 216 | 218 | 220 | 222 | 224 |
| 2148P | 226 | 228 | 230 | 232 | 234 | 236 | 238 | 240 |
| 2151P | 242 | 244 | 246 | 248 | 250 | 252 | 254 | 256 |
| 2153P | 258 | 260 | 262 | 264 | 266 | 268 | 270 | 272 |
| 2154P | 274 | 276 | 278 | 280 | 282 | 284 | 286 | 288 |
| 2290P | 290 | 292 | 294 | 296 | 298 | 300 | 302 | 304 |
| 1819N | 306 | 308 | 310 | 312 | 314 | 316 | 318 | 320 |
| 1821N | 322 | 324 | 326 | 328 | 330 | 332 | 334 | 336 |
| 1824N | 338 | 340 | 342 | 344 | 346 | 348 | 350 | 352 |
| 1827N | 354 | 356 | 358 | 360 | 362 | 364 | 366 | 368 |
| 1828N | 370 | 372 | 374 | 376 | 378 | 380 | 382 | 384 |
| 1829N | 386 | 388 | 390 | 392 | 394 | 396 | 398 | 400 |
| 1930N | 402 | 404 | 406 | 408 | 410 | 412 | 414 | 416 |
| 1934N | 418 | 420 | 422 | 424 | 426 | 428 | 430 | 432 |
| 1936N | 434 | 436 | 438 | 440 | 442 | 444 | 446 | 448 |
| 1937N | 450 | 452 | 454 | 456 | 458 | 460 | 462 | 464 |
| 1938N | 466 | 468 | 470 | 472 | 474 | 476 | 478 | 480 |
| 1940N | 482 | 484 | 486 | 488 | 490 | 492 | 494 | 496 |

Antibodies are typically referred to herein according to the following nomenclature: Fc prefix (e.g. "H4H", "H1M", "H2M"), followed by a numerical identifier (e.g. "2084" as shown in Table 1), followed by a "P" or "N" suffix. Thus, according to this nomenclature, an antibody may be referred to herein as, e.g., "H4H2084P". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs)—which are indicated by the numerical identifiers shown in Table 1—will remain the same. The P and N suffixes on the antibody designations used herein refer to antibodies having heavy and light chains with identical CDR sequences but with sequence variations in regions that fall outside of the CDR sequences (i.e., in the framework regions). Thus, P and N variants of a particular antibody have identical CDR sequences within their heavy and light chain variable regions but differ from one another within their framework regions.

Control Constructs Used in the Following Examples

Various control constructs (anti-ErbB3 antibodies) were included in the following experiments for comparative purposes. The control constructs are designated as follows: Control I: a human anti-ErbB3 antibody with heavy and light chain variable domains having the amino acid sequences of the corresponding domains of "Mab#6," as set forth in U.S. Pat. No. 7,846,440; Control II: a human anti-ErbB3 antibody with heavy and light chain variable domains having the amino acid sequences of the corresponding domains of "U1-59," as set forth in U.S. Pat. No. 7,705,130; and Control III: a human anti-ErbB3 antibody with heavy and light chain variable domains having the amino acid sequences of the corresponding domains of "U1-53," as set forth in U.S. Pat. No. 7,705,130.

Example 3. Surface Plasmon Resonance Derived Binding Affinities and Kinetic Constants of Human Monoclonal Anti-ErbB3 Antibodies Binding affinities and kinetic constants of human monoclonal anti-ErbB3 antibodies were determined by surface plasmon resonance at 25° C. and 37° C. (Tables 2-4). Measurements were conducted on a Biacore 2000 or T100 instrument. Antibodies, expressed with either mouse Fc (prefix H1M; H2M) or human IgG4 Fc (prefix H4H), were captured on an anti-mouse or anti human-Fc sensor surface (Mab capture format), and soluble monomeric (ErbB3.mmh; SEQ ID NO:497,) or dimeric (ErbB3-hFc; SEQ ID NO:498 or ErbB3-mFc; SEQ ID NO:499) protein was injected over the surface. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(ln 2/(60*$k_d$). Several clones showed sub-nanomolar affinity to monomeric (hErbB3.mmh) ErbB3 protein.

TABLE 2

Biacore Binding Affinities of Hybridoma mAbs (H1M and H2M) at 25° C. Binding at 25° C./Mab Capture Format

| Antibody | Analyte | ka (Ms$^{-1}$) | kd (s$^{-1}$) | K$_D$ (Molar) | T½ |
|---|---|---|---|---|---|
| H1M1819N | hErbB3.mmh | 3.19E+05 | 3.22E−04 | 1.01E−09 | 36 |
|  | hErbB3.hFc | 4.80E+05 | 5.88E−05 | 1.22E−10 | 196 |
| H2M1821N | hErbB3.mmh | 2.29E+05 | 1.99E−04 | 8.67E−10 | 58 |
|  | hErbB3.hFc | 4.61E+05 | 1.90E−05 | 4.13E−11 | 608 |
| H2M1824N | hErbB3.mmh | 2.23E+05 | 4.56E−05 | 2.05E−10 | 254 |
|  | hErbB3.hFc | 4.31E+05 | 1.44E−06 | 3.34E−12 | 8026 |
| H2M1827N | hErbB3.mmh | 2.19E+05 | 8.96E−05 | 4.09E−10 | 129 |
|  | hErbB3.hFc | 4.39E+05 | 7.58E−06 | 1.73E−11 | 1524 |
| H1M1828N | hErbB3.mmh | 5.13E+05 | 2.65E−04 | 5.15E−10 | 44 |
|  | hErbB3.hFc | 1.56E+06 | 4.34E−05 | 2.79E−11 | 266 |
| H2M1829N | hErbB3.mmh | 2.30E+05 | 6.46E−05 | 2.81E−10 | 179 |
|  | hErbB3.hFc | 4.36E+05 | 8.61E−06 | 1.98E−11 | 1341 |
| H2M1930N | hErbB3.mmh | 1.96E+05 | 1.09E−04 | 5.59E−10 | 106 |
|  | hErbB3.hFc | 4.04E+05 | 8.27E−06 | 2.05E−11 | 1396 |
| H2M1934N | hErbB3.mmh | 1.68E+05 | 7.35E−05 | 4.38E−10 | 157 |
|  | hErbB3.hFc | 3.59E+05 | 7.97E−06 | 2.22E−11 | 1450 |
| H2M1936N | hErbB3.mmh | 4.32E+04 | 2.85E−04 | 6.59E−09 | 41 |
|  | hErbB3.hFc | 6.41E+04 | 6.97E−05 | 1.09E−09 | 166 |
| H2M1937N | hErbB3.mmh | 8.26E+04 | 5.63E−05 | 6.82E−10 | 205 |
|  | hErbB3.hFc | 1.10E+05 | 1.27E−05 | 1.16E−10 | 908 |
| H2M1938N | hErbB3.mmh | 2.41E+05 | 1.44E−04 | 5.99E−10 | 80 |
|  | hErbB3.hFc | 4.51E+05 | 1.36E−05 | 3.01E−11 | 851 |
| H1M1940N | hErbB3.mmh | 2.89E+05 | 1.38E−04 | 4.77E−10 | 84 |
|  | hErbB3.hFc | 4.60E+05 | 2.43E−05 | 5.29E−11 | 475 |
| Control I | hErbB3.mmh | 5.14E+04 | 2.15E−04 | 4.18E−09 | 54 |
|  | hErbB3.hFc | 4.63E+04 | 1.63E−05 | 3.51E−10 | 711 |
| Control II | hErbB3.mmh | 1.41E+05 | 3.24E−04 | 2.30E−09 | 36 |
|  | hErbB3.hFc | 1.53E+05 | 4.28E−05 | 2.80E−10 | 270 |
| Control III | hErbB3.mmh | 1.54E+06 | 3.15E−02 | 2.05E−08 | 0.4 |
|  | hErbB3.hFc | 3.78E+06 | 8.84E−05 | 2.34E−11 | 131 |

TABLE 3

Biacore Binding Affinities of Human Fc mAbs (H4H) at 25° C.
Binding at 25° C./Mab Capture Format

| | Analyte | ka (Ms$^{-1}$) | kd (s$^{-1}$) | K$_D$ (Molar) | T½ |
|---|---|---|---|---|---|
| H4H1819N | hErbB3.mmh | 8.10E+06 | 3.51E-04 | 4.35E-11 | 33 |
| | hErbB3.mFc | 1.64E+07 | 1.54E-05 | 9.43E-13 | 748 |
| H4H1821N | hErbB3.mmh | 3.80E+06 | 1.92E-04 | 5.10E-11 | 60 |
| | hErbB3.mFc | 1.22E+07 | 4.33E-06 | 3.55E-13 | 2665 |
| H4H2084P | hErbB3.mmh | 2.49E+06 | 5.96E-05 | 2.39E-11 | 179 |
| | hErbB3.mFc | 3.83E+06 | 3.95E-06 | 1.03E-12 | 2695 |
| H4H2092P | hErbB3.mmh | 3.72E+06 | 1.03E-04 | 2.78E-11 | 103 |
| | hErbB3.mFc | 5.16E+06 | 7.46E-06 | 1.45E-12 | 1429 |
| H4H2094P | hErbB3.mmh | 1.89E+06 | 1.37E-05 | 7.22E-12 | 780 |
| | hErbB3.mFc | 3.03E+06 | 1.37E-06 | 4.52E-13 | 7779 |
| H4H2098P | hErbB3.mmh | 1.14E+06 | 7.89E-05 | 6.90E-11 | 135 |
| | hErbB3.mFc | 2.21E+06 | 8.97E-06 | 4.06E-12 | 1188 |
| H4H2102P | hErbB3.mmh | 8.86E+05 | 4.88E-05 | 5.51E-11 | 218 |
| | hErbB3.mFc | 1.58E+06 | 2.26E-06 | 1.43E-12 | 4721 |
| H4H2108P | hErbB3.mmh | 1.95E+06 | 8.13E-05 | 4.18E-11 | 131 |
| | hErbB3.mFc | 2.96E+06 | 4.33E-06 | 1.46E-12 | 2458 |
| H4H2111P | hErbB3.mmh | 2.21E+06 | 1.18E-04 | 5.31E-11 | 91 |
| | hErbB3.mFc | 3.50E+06 | 8.69E-06 | 2.49E-12 | 1225 |
| H4H2114P | hErbB3.mmh | 9.29E+05 | 9.88E-05 | 1.06E-10 | 108 |
| | hErbB3.mFc | 1.48E+06 | 7.98E-06 | 5.41E-12 | 1335 |
| H4H2132P | hErbB3.mmh | 2.16E+06 | 3.81E-05 | 1.77E-11 | 279 |
| | hErbB3.mFc | 3.49E+06 | 3.35E-06 | 9.58E-13 | 3183 |
| H4H2138P | hErbB3.mmh | 2.39E+06 | 5.01E-05 | 2.09E-11 | 213 |
| | hErbB3.mFc | 3.71E+06 | 5.46E-06 | 1.47E-12 | 1952 |
| H4H2140P | hErbB3.mmh | 1.66E+06 | 3.27E-05 | 1.98E-11 | 326 |
| | hErbB3.mFc | 2.51E+06 | 9.86E-07 | 3.93E-13 | 10797 |
| H4H2143P | hErbB3.mmh | 1.83E+06 | 9.73E-05 | 5.31E-11 | 109 |
| | hErbB3.mFc | 2.86E+06 | 4.63E-06 | 1.75E-12 | 2302 |
| H4H2146P | hErbB3.mmh | 2.79E+06 | 3.46E-05 | 1.24E-11 | 308 |
| | hErbB3.mFc | 4.54E+06 | 1.98E-06 | 4.35E-13 | 5392 |
| H4H2147P | hErbB3.mmh | 2.47E+06 | 1.08E-04 | 4.38E-11 | 98 |
| | hErbB3.mFc | 3.33E+06 | 4.58E-06 | 1.50E-12 | 2325 |
| H4H2148P | hErbB3.mmh | 3.98E+06 | 3.47E-05 | 8.71E-12 | 307 |
| | hErbB3.mFc | 5.91E+06 | 1.74E-06 | 2.95E-13 | 6110 |
| H4H2151P | hErbB3.mmh | 3.04E+06 | 2.86E-05 | 9.42E-12 | 372 |
| | hErbB3.mFc | 4.48E+06 | 9.52E-07 | 2.13E-13 | 11186 |
| H4H2153P | hErbB3.mmh | 2.94E+06 | 3.43E-05 | 1.17E-11 | 311 |
| | hErbB3.mFc | 3.67E+06 | 1.24E-06 | 3.37E-13 | 8603 |
| H4H2154P | hErbB3.mmh | 2.13E+06 | 3.73E-05 | 1.76E-11 | 285 |
| | hErbB3.mFc | 3.25E+06 | 9.77E-07 | 3.00E-13 | 10901 |
| H4H2290P | hErbB3.mmh | 5.82E+05 | 6.72E-05 | 1.15E-10 | 159 |
| | hErbB3.mFc | 8.00E+05 | 1.13E-05 | 1.40E-11 | 945 |

TABLE 4

Biacore Binding Affinities of Select mAbs at 37° C.
Binding at 37° C./Mab Capture Format

| | Analyte | ka (Ms$^{-1}$) | kd (s$^{-1}$) | K$_D$ (Molar) | T½ |
|---|---|---|---|---|---|
| H4H1819N | hErbB3.mmh | 1.21E+07 | 1.56E-03 | 1.29E-10 | 7 |
| | hErbB3.mFc | 3.68E+07 | 5.62E-05 | 1.53E-12 | 206 |
| H4H1821N | hErbB3.mmh | 6.49E+06 | 1.08E-03 | 1.67E-10 | 11 |
| | hErbB3.mFc | 1.87E+07 | 3.55E-05 | 1.89E-12 | 326 |
| Control I | hErbB3.mmh | 1.58E+05 | 5.48E-04 | 3.47E-09 | 21 |
| | hErbB3.mFc | 2.60E+05 | 1.01E-04 | 3.90E-10 | 114 |
| Control II | hErbB3.mmh | 3.23E+05 | 1.34E-03 | 4.13E-09 | 9 |
| | hErbB3.mFc | 1.44E+06 | 1.37E-04 | 9.50E-11 | 84 |
| Control III | hErbB3.mmh | 3.40E+06 | 7.90E-02 | 2.40E-08 | 0.1 |
| | hErbB3.mFc | 1.05E+07 | 1.77E-04 | 1.68E-11 | 65 |

As shown in Tables 2-4, many of the exemplary antibodies tested in this Example exhibited high affinity binding to ErbB3 that was superior or equivalent to the binding affinities of the control antibodies tested. Of note, several of the anti-ErbB3 antibodies of the present invention exhibited sub-nanomolar affinity to monomeric (hErbB3.mmh) ErbB3 protein.

Example 4. Anti-ErbB3 Antibodies Block Neuregulin 1b Binding to Human ErbB3

To further characterize anti-hErbB3 mAbs of the present invention, their ability to block ligand binding was examined via ELISA. Plates were coated with neuregulin 1b (1 μg/ml) overnight and then antibodies (0-50 nM) were incubated (1 hr, 25° C.) with either 50 pM ErbB3-hFc (SEQ ID NO:498; for hybridomas) or 50 pM ErbB3-mFc (SEQ ID NO:499; for hIgG4 antibodies) and then added to coated plates and allowed to incubate for an additional 1 hr at 25° C. Plates were washed and non-sequestered (plate bound) ErbB3 was detected with an anti-Fc poly conjugated with horseradish peroxidase (HRP). Plates were developed with TMB (3,3',5,5'-tetramethylbenzidine) and neutralized with sulfuric acid before reading absorbance at 450 nm on a Victor X5 plate reader. Data analysis used a sigmoidal dose-response model within Prism™ software. The calculated IC$_{50}$ value, defined as 50% of the antibody concentration required to achieve maximum blocking, was used as an indicator of blocking potency. Maximal blocking for each antibody was calculated by taking the difference in absorbance from zero to 50 nM antibody on the inhibition curve, divided by the difference in absorbance from 50 pM to zero ErbB3 on the dose curve. Results are shown in Tables 5 and 6.

TABLE 5

IC$_{50}$ Values for Anti-ErbB3 Hybridoma mAbs (H1M and H2M)

| Antibody | IC50(M) | Maximal Blocking (%) |
|---|---|---|
| H1M1819N | 3.15E−11 | 92 |
| H2M1821N | 2.85E−11 | 96 |
| H2M1824N | 2.51E−11 | 99 |
| H2M1827N | 2.29E−11 | 98 |
| H1M1828N | 3.00E−11 | 95 |
| H2M1829N | 2.38E−11 | 98 |
| H2M1930N | 2.22E−11 | 87 |
| H2M1934N | 2.61E−11 | 80 |
| H2M1936N | 5.27E−10 | 91 |
| H2M1937N | 4.40E−11 | 95 |
| H2M1938N | 2.49E−11 | 85 |
| H1M1940N | 5.30E−10 | 80 |

TABLE 6

IC$_{50}$ Values for Anti-ErbB3 Human Fc mAbs (H4H)

| Antibody | IC50(M) | Maximal Blocking (%) |
|---|---|---|
| H4H1819N | 2.00E−11 | 99 |
| H4H1821N | 1.80E−11 | 99 |
| H4H2084P | 8.73E−11 | 95 |
| H4H2092P | 5.94E−11 | 100 |
| H4H2094P | 9.00E−11 | 92 |
| H4H2098P | 1.35E−10 | 95 |
| H4H2102P | 1.86E−10 | 90 |
| H4H2108P | 1.16E−10 | 91 |
| H4H2111P | 4.97E−11 | 92 |
| H4H2114P | 1.63E−10 | 91 |
| H4H2132P | 9.57E−11 | 94 |
| H4H2138P | 1.06E−10 | 96 |
| H4H2140P | 9.46E−11 | 83 |
| H4H2143P | 8.35E−11 | 92 |
| H4H2146P | 1.77E−10 | 83 |
| H4H2147P | 5.06E−11 | 99 |
| H4H2148P | 5.08E−11 | 100 |
| H4H2151P | 7.51E−11 | 85 |
| H4H2153P | 7.40E−11 | 82 |
| H4H2154P | 9.01E−11 | 91 |

TABLE 6-continued

IC$_{50}$ Values for Anti-ErbB3 Human Fc mAbs (H4H)

| Antibody | IC50(M) | Maximal Blocking (%) |
|---|---|---|
| H4H2290P | 6.64E−11 | 99 |
| Control I | 5.74E−10 | 98 |
| Control III | 8.32E−11 | 96 |

As shown in Tables 5 and 6, several anti-ErbB3 antibodies of the present invention showed potent blocking and had IC$_{50}$ values that were at the theoretical bottom (25 pM) of the assay.

Example 5. Anti-ErbB3 mAbs Effectively Internalize Cell Surface ErbB3

To determine if anti-ErbB3 mAbs effectively internalize cell surface bound ErbB3, MCF-7 cells were incubated with select anti-ErbB3 antibody (10 µg/ml) for 30 minutes on ice, washed and then stained with a Dylight 488 conjugated anti-human Fab (10 µg/ml) for 30 minutes on ice. Tubes were then washed and split between an on ice and 37° C. incubation for 1 hour. After incubation all tubes were placed on ice and a Dylight 488 quenching antibody (50 µg/ml) was added. Solutions were incubated an additional 1 hour on ice. Fluorescent signals were measured using an Accuri flow cytometer.

As a relative measure of the amount of ErbB3 that was internalized upon antibody binding and subsequent incubation at 37° C., the internalized mean fluorescent intensity (MFI) was calculated as follows:

Internalized MFI = Total MFI − Surface MFI where:

Surface MFI = (Total MFI − MFI of Quenched Sample)/QE and

QE = 1 − [MFI of quenched sample at 4° C./MFI of unquenched sample at 4° C.]

The calculation of QE (quenching efficiency) assumes that no internalization occurs at 4° C. Table 7 shows that all antibodies tested induce HER3 internalization.

TABLE 7

Antibody-Induced HER3 Internalization at 37° C.

| Antibody | Total MFI mean ± S.D. | Surface MFI mean ± S.D. | Internalized MFI mean ± S.D. | % Internalized mean ± S.D. |
|---|---|---|---|---|
| H4H1819N | 39233 ± 9261 | 22663 ± 5026 | 16570 ± 5329 | 42 ± 7 |
| H4H1821N | 32351 ± 5658 | 11607 ± 4781 | 20744 ± 4993 | 64 ± 14 |
| Control I | 19004 ± 5903 | 11598 ± 6602 | 7406 ± 1776 | 42 ± 20 |
| Control II | 41517 ± 5696 | 23540 ± 11994 | 17977 ± 6299 | 45 ± 21 |
| Control III | 27349 ± 5310 | 8010 ± 729 | 19338 ± 5934 | 69 ± 8 |

Example 6. Inhibition of NRG1-Dependent Akt Phosphorylation by Anti-ErbB3 Antibodies Anti-ErbB3 antibodies were tested for their ability to inhibit phosphorylation of Akt in DU145 prostate cancer cells. Binding of NRG1 to ErbB3 results in ErbB3 phosphorylation, which leads to recruitment and activation of phosphatidylinositol 3-kinase (PI3-K). Activated PI3-K phosphorylates and activates the kinase Akt. Thus, Akt phosphorylation is a downstream marker of ErbB3 receptor activation. DU145 cells were seeded in 96-well plates and then serum-starved in medium containing 1% FBS overnight. Cells were then stimulated with 0.5 nM NRG1 (R&D Systems) for 30 min in the presence of 0.5 µg/ml human Fc control protein or various anti-ErbB3 antibodies at concentrations of 0.01, 0.1 or 0.5 µg/ml. Each concentration of antibody was tested in triplicate. Cells were lysed and the relative levels of phosphorylated Akt were determined using a phospho-Akt cell-based ELISA kit (R&D Systems), according to the manufacturer's instructions. The average percent inhibition of Akt phosphorylation for each anti-ErbB3 antibody versus the Fc control group is shown in Table 8.

TABLE 8

Inhibition of Akt phosphorylation by Anti-ErbB3 Antibodies

| | Percent inhibition of Akt phosphorylation | | |
|---|---|---|---|
| Antibody | 0.01 µg/ml ErbB3 antibody | 0.1 µg/ml ErbB3 antibody | 0.5 µg/ml ErbB3 antibody |
| H1M1819N | 29 | 72 | 75 |
| H2M1821N | 11 | 68 | 73 |
| H2M1824N | 25 | 63 | 74 |
| H2M1827N | 16 | 73 | 75 |
| H1M1828N | 22 | 66 | 75 |
| H2M1829N | 22 | 74 | 74 |
| H2M1930N | 39 | 64 | 66 |
| H2M1934N | 20 | 56 | 67 |
| H2M1936N | 6 | 30 | 67 |
| H2M1937N | −13 | 41 | 71 |
| H2M1938N | 40 | 63 | 74 |
| H1M1940N | 13 | 50 | 68 |
| Control I | −1 | 46 | 60 |
| Control II | 4 | 7 | 51 |
| Control III | 3 | 45 | 55 |

This example illustrates that several of the anti-ErbB3 antibodies of the present invention exhibited more potent blockade of Akt phosphorylation than the control anti-ErbB3 antibodies. For example, antibodies H1M1819N, H2M1821N, H2M1824N, H2M1827N, H1M1828N, H2M1829N, H2M1930N and H2M1938N inhibited Akt phosphorylation by at least 60% at the 0.1 µg/ml dose, while none of the control ErbB3 antibodies achieved an inhibition greater than 46% at that dose.

Example 7. Inhibition of Tumor Cell Growth by Anti-ErbB3 Antibodies

Select anti-ErbB3 antibodies were tested for their ability to inhibit the growth of A431 epidermoid carcinoma cells when used in combination with EGFR blockade. A431 cells in 96-well plates were incubated in medium containing 0.5% FBS and stimulated with 1 nM neuregulin-1 (NRG1) in the presence of an anti-EGFR antibody (1 µg/ml), an anti-ErbB3 antibody (1 µg/ml) or anti-EGFR (1 µg/ml) plus anti-ErbB3 antibody at 0.05, 0.25 or 1.0 µg/ml. The ligand (NRG1) and blocking antibodies (EGFR & ErbB3) were added at 0, 24 and 48 hrs during the 72-hour experiment. The relative change in the number of viable cells from the start of treatment until the 72-hour time point was reached was determined using standard methods (Cell Proliferation Assay Kit; Promega). The average percent decrease in cell growth for each anti-ErbB3 antibody versus an isotype control group is shown in Table 9.

TABLE 9

Inhibition of A431 Cell Growth by Anti-ErbB3 Antibodies

| | Percent decrease in the growth of A431 cells | | | |
|---|---|---|---|---|
| Antibody | 1.0 µg/ml ErbB3 antibody | anti-EGFR antibody + 0.05 µg/ml ErbB3 antibody | anti-EGFR antibody + 0.25 µg/ml ErbB3 antibody | anti-EGFR antibody + 1.0 µg/ml ErbB3 antibody |
| H1M1819N | 34 | 61 | 78 | 91 |
| H2M1821N | 16 | 35 | 62 | 85 |
| H2M1824N | 33 | 45 | 68 | 85 |
| H2M1827N | 15 | 53 | 75 | 84 |
| H1M1828N | 30 | 55 | 73 | 85 |
| H2M1829N | 31 | 53 | 76 | 89 |
| H2M1930N | 3 | 23 | 36 | 39 |
| H2M1934N | −3 | 24 | 30 | 28 |
| H2M1938N | 5 | 37 | 56 | 60 |
| H1M1940N | −4 | 19 | 20 | 19 |
| Control I | 19 | 31 | 37 | 56 |
| Control III | 7 | 22 | 21 | 32 |

This example illustrates that several of the anti-ErbB3 antibodies of the present invention exhibited more potent inhibition of A431 cell growth than the control anti-ErbB3 antibodies. For example, antibodies H1M1819N, H2M1821N, H2M1824N, H2M1827N, H1M1828N and H2M1829N inhibited cell growth by at least 60% at the 0.25 µg/ml dose when combined with anti-EGFR antibody, while control antibodies I and III inhibited cell growth by only 37% and 21%, respectively, under these experimental conditions.

Example 8. Inhibition of ErbB3 and Akt Phosphorylation by Anti-ErbB3 Antibodies

Select anti-ErbB3 antibodies were tested for their ability to inhibit NRG1-stimulated phosphorylation of ErbB3 and Akt in A431 epidermoid carcinoma and MCF7 breast cancer cells. In the first experiment, A431 cells were seeded in 6-well plates and incubated in complete medium overnight. Cells were then serum-starved (0.5% FBS) for 1 hr and stimulated with 1 nM NRG1 (R&D Systems) for 30 min in the presence of 5.0 µg/ml of isotype control or anti-ErbB3 antibody at 0.05, 0.25 or 5.0 µg/ml. Cells were lysed and Western blots were performed using antibodies against ErbB3 and Akt as well as their phosphorylated forms using standard methods. The ratios of phosphorylated ErbB3 or Akt to total ErbB3 or Akt were calculated and used to determine the percent inhibition of Akt or ErbB3 phosphorylation for each of the anti-ErbB3 antibodies relative to isotype control. Results for the inhibition of ErbB3 or AKT phosphorylation in A431 cells are shown in Tables 10 and 11, respectively.

TABLE 10

Percent Inhibition of ErbB3 Phosphorylation in A431 Cells

| Antibody | 0.05 µg/ml | 0.25 µg/ml | 5.0 µg/ml |
|---|---|---|---|
| H4H1819N | 98 | 105 | 107 |
| H4H1821N | 63 | 113 | 120 |
| Control I | −11 | 14 | 72 |
| Control III | −30 | −9 | −57 |

TABLE 11

Percent Inhibition of Akt Phosphorylation in A431 Cells

| Antibody | 0.05 µg/ml | 0.25 µg/ml | 5.0 µg/ml |
|---|---|---|---|
| H4H1819N | 84 | 104 | 113 |
| H4H1821N | 67 | 106 | 117 |
| Control I | 32 | 47 | 75 |
| Control III | 43 | 51 | 58 |

In a similar experiment, MCF7 cells were seeded in 6-well plates and incubated in complete medium for 2 days. Cells were then serum-starved (0.5% FBS) for 1 hr and then stimulated with 1 nM NRG1 (R&D Systems) for 30 min in the presence of 5.0 µg/ml of isotype control or anti-ErbB3 antibody at of 0.05, 0.25, 1.0 or 5.0 µg/ml. Western blots and data analysis were carried out in a similar manner for those experiments conducted with A431 cells. Results for the inhibition of ErbB3 or AKT phosphorylation in MCF7 cells are shown in Tables 12 and 13, respectively.

TABLE 12

Percent Inhibition of ErbB3 Phosphorylation in MCF7 Cells

| Antibody | 0.05 µg/ml | 0.25 µg/ml | 1.0 µg/ml | 5.0 µg/ml |
|---|---|---|---|---|
| H4H1819N | 37 | 79 | 92 | 96 |
| H4H1821N | 57 | 92 | 96 | 97 |
| Control I | 0 | 17 | 44 | 81 |
| Control III | 4 | 12 | 60 | 61 |

TABLE 13

Percent Inhibition of Akt Phosphorylation in MCF7 Cells

| Antibody | 0.05 µg/ml | 0.25 µg/ml | 1.0 µg/ml | 5.0 µg/ml |
|---|---|---|---|---|
| H4H1819N | 13 | 36 | 80 | 90 |
| H4H1821N | 17 | 69 | 82 | 89 |
| Control I | 21 | 29 | 34 | 46 |
| Control III | 35 | 28 | 29 | 35 |

This Example illustrates that representative anti-ErbB3 antibodies of the invention exhibited superior ability to inhibit phosphorylation of ErbB3 and Akt compared to control antibodies under most of the experimental conditions tested. In A431 cells, for example, H4H1819N and H4H1821N completely inhibited both ErbB3 and Akt phosphorylation at 0.25 µg/ml while the control antibodies never achieved complete inhibition, even at 5.0 µg/ml. Similarly, in MCF7 cells, H4H1819N and H4H1821N at 1.0 µg/ml inhibited ErbB3 and Akt phosphorylation to a greater extent than either of the control anti-ErbB3 antibodies even at 5.0 µg/ml.

Example 9. Inhibition of Tumor Growth by Anti-ErbB3 Antibodies

Select anti-ErbB3 antibodies were tested for their ability to inhibit the growth of human tumor xenografts in immunocompromised mice. Briefly, $1-5 \times 10^6$ A431 human epidermoid carcinoma cells or A549 human non-small cell lung cancer cells (ATCC) were implanted subcutaneously into the flank of 6-8 week old SCID mice (Taconic, Hudson, N.Y.). After tumors reached an average volume of 100-150 mm$^3$, mice were randomized into groups for treatment (n=6 mice per group). In the first experiment, mice bearing A431 tumors were administered human Fc (SEQ ID NO:500, 12.5 mg/kg), or anti-ErbB3 antibody (0.5 or 12.5 mg/kg). All antibodies were administered via subcutaneous injection twice per week for approximately 3 weeks. Tumor volumes were measured twice per week over the course of the experiment and tumor weights were determined upon excision of tumors at the conclusion of the experiment. Average tumor size relative to the Fc treated group as well as final tumor weights were calculated for each group. Results are summarized in Table 14.

TABLE 14

Inhibition of A431 Tumor Growth in SCID Mice (Hybridoma mAbs - H1M and H2M)

| Antibody (mg/kg) | Tumor Growth in mm$^3$ from Start of Treatment (mean ± S.D.) | Average % Decrease in Tumor Growth | Avg Tumor Weight (g) | Average % Decrease in Tumor Weight |
|---|---|---|---|---|
| hFc ctrl (12.5) | 860 ± 358 | — | 0.778 ± 0.268 | — |
| H1M1819N (0.5) | 355 ± 178 | 59 | 0.520 ± 0.155 | 33 |
| H2M1821N (0.5) | 280 ± 131 | 67 | 0.428 ± 0.209 | 45 |
| H2M1827N (0.5) | 246 ± 71 | 71 | 0.432 ± 0.152 | 45 |
| H2M1829N (0.5) | 392 ± 265 | 54 | 0.480 ± 0.283 | 38 |
| Control I (0.5) | 862 ± 199 | 0 | 0.815 ± 0.190 | −5 |
| Control I (12.5) | 299 ± 139 | 65 | 0.438 ± 0.217 | 44 |

In a similar experiment, using selected antibodies in the human IgG4 format yield similar results, as summarized in Table 15.

TABLE 15

Inhibition of A431 Tumor Growth in SCID Mice (Human Fc mAbs - H4H)

| Antibody (mg/kg) | Tumor Growth in mm$^3$ from Start of Treatment (mean ± S.D.) | Average % Decrease in Tumor Growth | Avg Tumor Weight (g) | Average % Decrease in Tumor Weight |
|---|---|---|---|---|
| hFc ctrl (12.5) | 797 ± 65 | — | 1.31 ± 0.142 | — |
| H4H1819N (0.5) | 161 ± 69 | 80 | 0.453 ± 0.010 | 65 |
| H4H1819N (12.5) | 110 ± 47 | 86 | 0.458 ± 0.108 | 65 |
| H4H1821N (0.5) | 148 ± 73 | 81 | 0.482 ± 0.058 | 63 |
| H4H1821N (12.5) | 74 ± 100 | 91 | 0.392 ± 0.117 | 70 |
| Control I (0.5) | 675 ± 228 | 15 | 0.928 ± 0.215 | 29 |
| Control I (12.5) | 95 ± 51 | 88 | 0.361 ± 0.063 | 72 |
| Control III (0.5) | 409 ± 254 | 49 | 0.687 ± 0.269 | 48 |
| Control III (12.5) | 219 ± 129 | 73 | 0.545 ± 0.096 | 58 |

In similar experiments, the effect of various anti-ErbB3 antibodies on the growth of A549 tumor xenografts was determined, as summarized in Table 16.

TABLE 16

Inhibition of A549 Tumor Growth in SCID Mice

| Antibody (mg/kg) | Tumor Growth in mm$^3$ from Start of Treatment (mean ± S.D.) | Average % Decrease in Tumor Growth | Avg Tumor Weight (g) | Average % Decrease in Tumor Weight |
|---|---|---|---|---|
| hFc ctrl (12.5) | 727 ± 184 | — | 1.27 ± 0.332 | — |
| H4H1821N (0.2) | 366 ± 90 | 50 | 0.811 ± 0.145 | 37 |
| H4H1821N (0.5) | 347 ± 52 | 52 | 0.820 ± 0.245 | 36 |
| H4H1821N (2.5) | 346 ± 106 | 52 | 0.783 ± 0.175 | 39 |
| Control I (0.5) | 719 ± 230 | 1 | 1.328 ± 0.363 | −3.78 |
| Control I (2.5) | 614 ± 177 | 15 | 0.985 ± 0.198 | 23 |

As shown in this Example, antibodies H4H1819N and H4H1821N each significantly inhibited tumor growth in vivo to an extent that was superior, or equivalent to the extent of tumor growth inhibition observed with administration of the control anti-ErbB3 antibodies tested.

Example 10. Inhibition of Tumor Growth by Anti-ErbB3 Antibodies in Combination with Agents that Block Other ErbB Family Members The effect of a combination treatment with H4H1821N plus an inhibitory anti-EGFR antibody ("anti-EGFR mAb") on human tumor xenograft growth was tested. Briefly, ×10$^6$ FaDu human hypopharyngeal carcinoma cells (ATCC) were implanted subcutaneously into the flank of 6-8 week old SCID mice (Taconic, Hudson, N.Y.). After tumors reached an average volume of 150-200 mm$^3$, mice were randomized into groups for treatment (n=6 mice per group). Mice were administered human Fc control protein (12.5 mg/kg), H4H1821N (2.5 mg/kg), anti-EGFR mAb (10 mg/kg) or the combination of H4H1821N plus anti-EGFR mAb (2.5+10 mg/kg). All antibodies were administered via subcutaneous injection twice per week. Tumor volumes were measured twice per week over the course of the experiment and tumor weights were determined upon excision of tumors at the conclusion of the experiment. Averages (mean+/−standard deviation) of the tumor growth from the start of treatment and the tumor weights were calculated for each treatment group. The percent decrease of tumor growth and tumor weight was calculated from comparison to the Fc control group. The results are shown in Table 17.

TABLE 17

Inhibition of FaDu tumor xenograft growth in SCID mice

| Antibody (mg/kg) | Tumor Growth in mm$^3$ from Start of Treatment (mean ± S.D.) | Average % Decrease in Tumor Growth | Average Tumor Weight (g) | Average % Decrease in Tumor Weight |
|---|---|---|---|---|
| hFc control (12.5) | 1099 ± 186 | — | 0.993 ± 0.176 | — |
| H4H1821N (2.5) | 284 ± 175 | 74 | 0.522 ± 0.177 | 47 |
| anti-EGFR mab (10) | 55 ± 115 | 95 | 0.215 ± 0.120 | 78 |
| H4H1821N + anti-EGFR mab (2.5 + 10) | −199 ± 38 | 118 | 0.024 ± 0.020 | 98 |

In a similar experiment, the effect of a combination treatment with H4H1821N plus the inhibitory anti-HER2 antibody clone 4D5v8 as described in Carter et al., *Proc. Natl. Acad. Sci. USA* 89:4285-4289 (1992) on human tumor xenograft growth was tested. Briefly, 1×10⁷ BT474 human breast cancer cells (ATCC) were implanted subcutaneously into the flank of 6-8 week old NCR nude mice (Taconic, Hudson, N.Y.). After tumors reached an average volume of 150-200 mm³, mice were randomized into groups for treatment (n=5 mice per group). Mice were administered human Fc control protein (25 mg/kg), H4H1821N (12.5 mg/kg), 4D5v8 (12.5 mg/kg) or the combination of H4H1821N plus 4D5v8 (12.5+12.5 mg/kg). All antibodies were administered via subcutaneous injection twice per week. Tumor volumes were measured twice per week over the course of the experiment. The average (mean+/−standard deviation) tumor growth from the start of treatment was calculated for each treatment group. The percent decrease of tumor growth was calculated from comparison to the Fc control group. The results are shown in Table 18.

TABLE 18

Inhibition of BT474 tumor xenograft growth in nude mice

| Antibody (mg/kg) | Tumor growth in mm3 from start of treatment (mean ± SD) | Average % Decrease in Tumor Growth |
|---|---|---|
| hFc control (25) | 194 ± 39 | — |
| H4H1821N (12.5) | 137 ± 65 | 29 |
| 4D5v8 (12.5) | 34 ± 121 | 82 |
| H4H1821N + 4D5v8 (12.5 + 12.5) | −79 ± 39 | 141 |

This example illustrates that combined treatment with H4H1821N plus anti-EGFR or anti-HER2 antibodies provides more potent inhibition of tumor growth than the single agent treatments. In both FaDu and BT474 tumor xenografts, the combination treatments, but not the single agents, caused the average tumor size to decrease (tumor regression).

Example 11. Epitope Mapping of H4H1821N Binding to ErbB3 by H/D Exchange

Experiments were conducted to determine the amino acid residues of ErbB3 with which H4H1821N interacts. For this purpose H/D exchange epitope mapping was carried out. A general description of the H/D exchange method is set forth in e.g., Ehring (1999) *Analytical Biochemistry* 267(2):252-259; and Engen and Smith (2001) *Anal. Chem.* 73:256A-265A.

To map the binding epitope(s) of antibody H4H1821N on ErbB3 via H/D exchange, a recombinant construct consisting of the extracellular domain of hErbB3 (amino acids 1-613 of SEQ ID NO:498) with a C-terminal myc-myc-hexahistidine tag ("hErbB3-mmH") was used. hErbB3-mmH was first deglycosylated with PNGase F (New England BioLabs) under native conditions. Antibody H4H1821N was covalently attached to N-hydroxysuccinimide (NHS) agarose beads (GE Lifescience).

In the 'on-solution/off-beads' experiment (on-exchange in solution followed by off-exchange on beads), the ligand (deglycosyated hErbB3-mmH) was deuterated for 5 min or 10 min in PBS buffer prepared with $D_2O$, and then bound to H4H1821N beads through a 2 min incubation. The ErbB3-bound beads were washed with PBS aqueous buffer (prepared with $H_2O$) and incubated for half of the on-exchange time in PBS buffer. After the off-exchange, the bound ErbB3 was eluted from beads with an ice-cold low pH TFA solution. The eluted ErbB3 was then digested with immobilized pepsin (Thermo Scientific) for 5 min. The resulting peptides were desalted using ZipTip® chromatographic pipette tips and immediately analyzed by UltrafleXtreme matrix assisted laser desorption ionization time of flight (MALDI-TOF) mass spectrometry (MS).

In the 'on-beads/off-beads' experiment (on-exchange on beads followed by off-exchange on beads), ErbB3 was first bound to H4H1821N beads and then incubated for 5 min or 10 min in $D_2O$ for on-exchange. The following steps (off-exchange, pepsin digestion, and MS analysis) were carried out as described for the 'on-solution/off-beads' procedure. The centroid values or average mass-to-charge ratios (m/z) of all the detected peptides were calculated and compared between these two sets of experiments.

The results are summarized in Table 19 which provides a comparison of the centroid m/z values for all the detected peptides identified by liquid chromatography-matrix assisted laser desorption ionization (LC-MALDI) MS following the H/D exchange and peptic digest procedure. While the majority of the observed peptic peptides gave similar centroid values for both the on-solution/off-beads and on-beads/off-beads experiments, three segments corresponding to residues 345-367, 423-439, and 451-463 of the extracellular domain of ErbB3 (SEQ ID NO:498) had delta centroid values (Δ) greater than or equal to 0.20 m/z in both the '5 min on-/2.5 min off-exchange' experiment (Experiment I) and the '10 min on-/5 min off-exchange' experiment (Experiment II). For purposes of the present Example, a positive difference (Δ) of at least 0.20 m/z in both experiments indicates amino acids protected by antibody binding. Segments meeting this criterion are indicated by bold text and an asterisk (*) in Table 19.

TABLE 19

H4H1821N Binding to hErbB3-mmH

| Residues (of SEQ ID NO: 498) | Experiment I 5 min on-/2.5 min off-exchange | | | Experiment II 10 min on-/5 min off-exchange | | |
|---|---|---|---|---|---|---|
| | On-solution/ Off Beads | On-Beads/ Off-Beads | Δ | On-solution/ Off Beads | On-Beads/ Off-Beads | Δ |
| 46-57 | 1287.52 | 1287.41 | 0.11 | 1287.58 | 1287.64 | −0.06 |
| 58-63 | 844.97 | 844.97 | 0.00 | 845.04 | 844.99 | 0.06 |
| 58-66 | 1102.34 | 1102.25 | 0.09 | 1102.25 | 1102.30 | −0.05 |
| 58-67 | 1265.65 | 1265.60 | 0.05 | 1265.57 | 1265.50 | 0.07 |
| 58-69 | 1477.84 | 1477.77 | 0.07 | 1477.79 | 1477.79 | 0.01 |
| 59-69 | 1364.46 | 1364.48 | −0.02 | 1364.39 | 1364.42 | −0.03 |
| 61-69 | 1050.70 | 1050.67 | 0.03 | 1050.75 | 1050.68 | 0.07 |
| 75-96 | 2509.35 | 2509.27 | 0.08 | 2509.21 | 2509.21 | 0.01 |
| 76-96 | 2362.11 | 2362.09 | 0.01 | 2362.11 | 2361.97 | 0.14 |

TABLE 19-continued

H4H1821N Binding to hErbB3-mmH

| Residues (of SEQ ID NO: 498) | Experiment I 5 min on-/2.5 min off-exchange | | | Experiment II 10 min on-/5 min off-exchange | | |
|---|---|---|---|---|---|---|
| | On-solution/ Off Beads | On-Beads/ Off-Beads | Δ | On-solution/ Off Beads | On-Beads/ Off-Beads | Δ |
| 84-96 | 1526.22 | 1526.05 | 0.16 | 1526.09 | 1526.08 | 0.01 |
| 84-98 | 1710.14 | 1710.11 | 0.03 | 1710.17 | 1710.07 | 0.11 |
| 84-99 | 1857.37 | 1857.34 | 0.03 | 1857.39 | 1857.33 | 0.06 |
| 86-96 | 1270.52 | 1270.50 | 0.02 | 1270.50 | 1270.45 | 0.05 |
| 100-114 | 1750.75 | 1750.60 | 0.15 | 1750.85 | 1750.75 | 0.11 |
| 100-114 | 1766.52 | 1766.55 | −0.03 | 1766.63 | 1766.47 | 0.16 |
| 100-120 | 2476.03 | 2475.80 | 0.23 | 2476.04 | 2475.96 | 0.08 |
| 103-117 | 1789.63 | 1789.48 | 0.14 | 1789.69 | 1789.44 | 0.24 |
| 112-120 | 1142.00 | 1141.95 | 0.05 | 1142.01 | 1142.06 | −0.05 |
| 144-154 | 1431.72 | 1431.72 | 0.00 | 1431.76 | 1431.67 | 0.08 |
| 345-365 | 2328.64 | 2328.64 | 0.00 | 2328.57 | 2328.64 | −0.07 |
| 345-367* | 2542.60 | 2542.34 | 0.26 | 2542.67 | 2542.47 | 0.20 |
| 366-378 | 1568.81 | 1568.70 | 0.11 | 1568.88 | 1568.78 | 0.10 |
| 368-373 | 807.97 | 807.95 | 0.02 | 807.94 | 807.88 | 0.06 |
| 368-376 | 1079.25 | 1079.30 | −0.04 | 1079.38 | 1079.30 | 0.08 |
| 368-377 | 1242.49 | 1242.40 | 0.09 | 1242.48 | 1242.43 | 0.05 |
| 368-378 | 1355.82 | 1355.68 | 0.14 | 1355.70 | 1355.73 | −0.03 |
| 368-379 | 1469.55 | 1469.56 | −0.01 | 1469.63 | 1469.57 | 0.06 |
| 368-380 | 1583.09 | 1583.10 | −0.01 | 1583.04 | 1583.03 | 0.01 |
| 369-378 | 1208.29 | 1208.25 | 0.03 | 1208.33 | 1208.30 | 0.03 |
| 397-408 | 1295.45 | 1295.47 | −0.01 | 1295.41 | 1295.36 | 0.05 |
| 397-411 | 1643.12 | 1643.04 | 0.08 | 1643.03 | 1642.98 | 0.05 |
| 397-412 | 1756.26 | 1756.08 | 0.18 | 1756.18 | 1756.04 | 0.14 |
| 405-411 | 857.06 | 856.97 | 0.09 | 857.09 | 857.02 | 0.07 |
| 423-435 | 1434.94 | 1434.82 | 0.11 | 1434.96 | 1434.78 | 0.18 |
| 423-436* | 1598.08 | 1597.89 | 0.20 | 1598.27 | 1598.06 | 0.21 |
| 424-439* | 1812.55 | 1812.27 | 0.28 | 1812.76 | 1812.37 | 0.39 |
| 423-439* | 1869.57 | 1869.29 | 0.28 | 1869.79 | 1869.41 | 0.38 |
| 424-435 | 1377.85 | 1377.69 | 0.16 | 1378.16 | 1377.93 | 0.22 |
| 424-436* | 1541.12 | 1540.90 | 0.21 | 1541.40 | 1541.00 | 0.20 |
| 425-439* | 1665.29 | 1665.04 | 0.26 | 1665.55 | 1665.22 | 0.33 |
| 451-463* | 1585.74 | 1585.51 | 0.23 | 1585.77 | 1585.53 | 0.24 |
| 618-641 | 2828.04 | 2827.98 | 0.06 | 2827.98 | 2827.89 | 0.10 |
| 621-629 | 989.16 | 989.14 | 0.02 | 989.27 | 989.28 | −0.01 |
| 621-641 | 2498.60 | 2498.59 | 0.01 | 2498.65 | 2498.53 | 0.12 |

The H/D exchange results summarized in Table 19 indicate that the three regions corresponding to amino acids 345-367, 423-439, and 451-463 of SEQ ID NO:498 are protected from full off-exchange by H4H1821N binding to ErbB3 after on-exchange. Significantly, all three regions are located within domain III of the ErbB3 extracellular domain. Therefore, this Example suggests that antibody H4H1821N binds a discontinuous epitope within domain III of the human ErbB3 extracellular domain consisting of these three amino acid segments or otherwise results in protection of these residues from H/D exchange (e.g., via conformational change or allosteric effects upon antibody binding).

Example 12. Clinical Trial of an Anti-ErbB3 Antibody in Combination with Erlotinib or Cetuximab in Patients with Advanced Colorectal Cancer (CRC), Non-Small Cell Lung Cancer (NSCLC) or Head and Neck Cancer (SCCHN)

A clinical trial is conducted with the exemplary anti-ErbB3 antibody H4H1821N in patients with advanced colorectal cancer (CRC), non-small cell lung cancer (NSCLC) or head and neck cancer (SCCHN). The trial is divided into two phases: a dose escalation phase and a safety expansion phase. In the dose escalation phase, all patients are initially administered H4H1821N intravenously (IV) at a dose of 3, 10 or 20 mg/kg. Following the initial dose of H4H1821N, the treatment regimen is modified based on cancer type: NSCLC patients begin a regimen of 150 mg Erlotinib once daily in combination with H4H1821N at 3, 10 or 20 mg/kg IV, once every 14 days; CRC and SCCHN patients begin a regimen of Cetuximab 250 mg/m$^2$ IV once a week in combination with H4H1821N at 3, 10 or 20 mg/kg IV, once every 14 days. In the safety expansion phase, NSCLC patients receive H4H1821N (at the recommended Phase 2 dose) IV once every 14 days in combination with 150 mg Erlotinib once daily; CRC and SCCHN patients receive H4H1821N (at the recommended Phase 2 dose) IV once every 14 days in combination with Cetuximab 250 mg/m$^2$ IV once a week.

It is expected that combination therapy comprising the anti-ErbB3 antibody H4H1821N and Erlotinib or Cetuximab will provide observable clinical improvements in patients with NSCLC, CRC and/or SCCHN to a greater extent than monotreatment with Erlotinib or Cetuximab alone.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. A method of treating a cancer in a subject, the method comprising administering to the subject an antibody that specifically binds ErbB3, or an antigen-binding fragment thereof, wherein the antibody or antigen-binding fragment comprises three heavy chain complementarity determining regions (HCDR1, HCDR2, and HCDR3) comprising the amino acid sequence of SEQ ID NOs: 324, 326, and 328, respectively, and three light chain complementarity determining regions (LCDR1, LCDR2, and LCDR3) comprising the amino acid sequence of SEQ ID NOs: 332, 334, and 336, respectively; wherein the cancer is a lung cancer, a colorectal cancer, or a head and neck cancer.

2. The method of claim 1, wherein the cancer is a lung cancer.

3. The method of claim 1, wherein the cancer is a non-small cell lung cancer.

4. The method of claim 1, wherein the antibody or antigen-binding fragment comprises a heavy chain variable region comprising the amino acid sequence of SEQ ID NO: 322 and a light chain variable region comprising the amino acid sequence of SEQ ID NO: 330.

5. The method of claim 1, wherein the antibody or antigen-binding fragment thereof is formulated in a pharmaceutical composition comprising a pharmaceutically acceptable carrier or diluent.

6. The method of claim 1, further comprising administering to the subject a second therapeutic agent.

7. The method of claim 6, wherein the second therapeutic agent is selected from the group consisting of an anti-EGFR antibody, cetuximab, panitumumab, a small molecule inhibitor of EGFR, erlotinib, gefitinib, an anti-HER2 antibody, trastuzumab, an anti-ErbB4 antibody, and an anti-EGFRvIII antibody.

8. The method of claim 7, wherein the second therapeutic agent is an anti-EGFR antibody.

* * * * *

SEQUENCE LISTING

<160> NUMBER OF SEQ ID NOS: 500

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1

```
caggtgcagc tggtggagtc tgggggaggc gtggtccagt ctgggaagtc cctgagactc      60
tcctgtgtag cgtctggatt caccttcagt aattatggca tgcactgggt ccgccagact     120
ccaggcaagg gctggagtg gtggcacgt atatggtttg atggaactaa taaatactac       180
acagactccg tgaagggccg attcaccctg tccagagaca gttccaagaa cacgctgtat     240
ctgcaaatga acagcctgag agccgaggac acggctgtct atttctgtgc gagagaagag     300
tcattggaac tagaccacta tgttatggac gtctggggcc aagggaccac ggtcaccgtc     360
tcctca                                                                366
```

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Glu Ser Gly Gly Gly Val Val Gln Ser Gly Lys
1               5                   10                  15
Ser Leu Arg Leu Ser Cys Val Ala Ser Gly Phe Thr Phe Ser Asn Tyr
            20                  25                  30
Gly Met His Trp Val Arg Gln Thr Pro Gly Lys Gly Leu Glu Trp Val
        35                  40                  45
Ala Arg Ile Trp Phe Asp Gly Thr Asn Lys Tyr Tyr Thr Asp Ser Val
    50                  55                  60
Lys Gly Arg Phe Thr Leu Ser Arg Asp Ser Ser Lys Asn Thr Leu Tyr
65                  70                  75                  80
Leu Gln Met Asn Ser Leu Arg Ala Glu Asp Thr Ala Val Tyr Phe Cys
                85                  90                  95
Ala Arg Glu Glu Ser Leu Glu Leu Asp His Tyr Val Met Asp Val Trp
            100                 105                 110
Gly Gln Gly Thr Thr Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct tcagtaatta tggc                                             24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic
```

<400> SEQUENCE: 4

Gly Phe Thr Phe Ser Asn Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatggtttg atggaactaa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Trp Phe Asp Gly Thr Asn Lys
1               5

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
gcgagagaag agtcattgga actagaccac tatgttatgg acgtc                   45

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Arg Glu Glu Ser Leu Glu Leu Asp His Tyr Val Met Asp Val
1               5                   10                  15

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9
gccatccaga tgacccagtc tccatcctcc ctgtctgcat ctgtaggaga cagagtcacc    60
atcacttgcc gggcaagtca ggacattaga gatgatttag ctggtttca gcagaaaccc   120 gggaaagccc ctaacctcct gatctatgct gcatccagtt tacaaagtgg ggtcccatca   180
aggttcagcg gcagtggatc tggcacagat tcactctca ccatcagcag cctgcagcct   240 gaggatttg caacttatta ctgtctacaa gattacaatt atccgctcac tttcggcgga   300
gggaccaagg tggagatcaa acga                                         324

```
<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10
```

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asp Asp
            20                  25                  30

Leu Gly Trp Phe Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys Arg
            100                 105

```
<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
caggacatta gagatgat                                                 18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12
```

Gln Asp Ile Arg Asp Asp
1               5

```
<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14
```

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
ctacaagatt acaattatcc gctcact                                         27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Leu Gln Asp Tyr Asn Tyr Pro Leu Thr
1               5

<210> SEQ ID NO 17
<211> LENGTH: 357
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaggt gtggtacggc ctgggggtc cctgagactc      60 tcctgtgcag cctctggatt cacctttgaa gattatggca tgaattgggt ccgccaagtt    120
ccagggaagg gctggagtg gtctctggt actaattgga atggtggtat cacaggttat     180
acaggctctg tgaagggccg attcaccatc tccagagaca cgccaagaa ctccctatat    240 ctacaaatga acagtctgag agccgaggac acggccttgt atcactgtgc gagagatagc    300
ggggatcaag atgcttttga tatctggggc caagggacaa tggtcaccgt ctcttca       357

<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Glu Asp Tyr
            20                  25                  30

Gly Met Asn Trp Val Arg Gln Val Pro Gly Lys Gly Leu Glu Trp Val
        35                  40                  45

Ser Gly Thr Asn Trp Asn Gly Gly Ile Thr Gly Tyr Thr Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Asp Ser Gly Asp Gln Asp Ala Phe Asp Ile Trp Gly Gln Gly
            100                 105                 110

Thr Met Val Thr Val Ser Ser
        115

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct ttgaagatta tggc                                         24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Glu Asp Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
actaattgga atggtggtat caca                                         24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Thr Asn Trp Asn Gly Gly Ile Thr
1               5

<210> SEQ ID NO 23
<211> LENGTH: 36
<212> TYPE: DNA
<213> ORGANISM: Artificial Sequence
<220> FEATURE:
<223> OTHER INFORMATION: Synthetic

<400> SEQUENCE: 23
gcgagagata gcggggatca agatgctttt gatatc                            36

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Ala Arg Asp Ser Gly Asp Gln Asp Ala Phe Asp Ile
1               5                   10

<210> SEQ ID NO 25
<211> LENGTH: 324
<212> TYPE: DNA
<213> ORGANISM: Artificial Sequence
<220> FEATURE:
<223> OTHER INFORMATION: Synthetic

<400> SEQUENCE: 25

```
gacatccagt tgacccagtc tccatccttc ctgtctgcat ctgtaggaga cagagtcacc      60
atcacttgct gggccagtca ggacattagc agttatttag cctggtatca gcaaaaacca     120
gggaaagccc ctaaactcct gatctatgct gcatccactt tccaaagtgg ggtcccatca     180
agattcagcg gcagtggatc tgggacagaa ttcactctca caatcagcaa cctgcagcct     240
gaagattttg caacttatta ctgtcaacag cttgatagtt accctctctc tttcggcgga     300
gggaccaagg tggagatcaa acga                                            324
```

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Phe Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Leu Asp Ser Tyr Pro Leu
                85                  90                  95

Ser Phe Gly Gly Gly Thr Lys Val Glu Ile Lys Arg
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
caggacatta gcagttat                                                    18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Asp Ile Ser Ser Tyr
1               5

<210> SEQ ID NO 29

```
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc                                                                 9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caacagcttg atagttaccc tctctct                                            27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln Leu Asp Ser Tyr Pro Leu Ser
1               5

<210> SEQ ID NO 33
<211> LENGTH: 369
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ttggtacagc ctggggggtc cctgagactc        60
tcctgtgcag cctctggatt caccttagt agctacgaca tgcactgggt ccgccaagca        120
acaggaaaag gtctggagtg ggtctcagct attggtcctg ctggtgacac atactatcca       180
gtctccgcga tgggccgatt caccatctcc agagatgatg ccaagaactc cttgtatctt       240
caaatgaaca gcctgagagc cggggacacg gctgtctatt actgtgcaag agagggggtc       300
acaattcgtc cggacgacta ctttggtctg gacgtctggg gccaaggaac cacggtcacc       360
gtctccgcc                                                              369

<210> SEQ ID NO 34
<211> LENGTH: 123
<212> TYPE: PRT
<213> ORGANISM: Artificial Sequence
<220> FEATURE:
<223> OTHER INFORMATION: Synthetic
```

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Pro Ala Gly Asp Thr Tyr Tyr Pro Val Ser Ala Met
    50                  55                  60

Gly Arg Phe Thr Ile Ser Arg Asp Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Val Thr Ile Arg Pro Asp Asp Tyr Phe Gly Leu Asp Val
            100                 105                 110

Trp Gly Gln Gly Thr Thr Val Thr Val Ser Ala
        115                 120

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct ttagtagcta cgac                                      24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Ser Tyr Asp
1               5

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
attggtcctg ctggtgacac a                                         21

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ile Gly Pro Ala Gly Asp Thr
1               5

<210> SEQ ID NO 39

```
<211> LENGTH: 51
<212> TYPE: DNA
<213> ORGANISM: Artificial Sequence
<220> FEATURE:
<223> OTHER INFORMATION: Synthetic

<400> SEQUENCE: 39
gcaagagagg gggtcacaat tcgtccggac gactactttg gtctggacgt c            51

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Ala Arg Glu Gly Val Thr Ile Arg Pro Asp Asp Tyr Phe Gly Leu Asp
1               5                   10                  15

Val

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gacatccagt tgacccagtc tccatccttc ctgtctgcat ctgtgggaga cagagtcacc    60
atcacttgct gggccagtca gggcattagc gattatttag cctggtatca gaaaaaacca   120
gggaaagccc ctcagctcct gatctatgct gcaaccactt tgcaaagtgg ggtcccatct   180
aggttcagcg gcagtggatc tgggacagaa ttcactctca caatcagcag cctgcagcct   240
gaagattttg caacttatta ctgtcaacag cttaatactt acccactcac tttcggcgga   300
gggaccaagg tggagatcaa acga                                         324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Asp Tyr
            20                  25                  30

Leu Ala Trp Tyr Gln Lys Lys Pro Gly Lys Ala Pro Gln Leu Leu Ile
        35                  40                  45

Tyr Ala Ala Thr Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Thr Tyr Pro Leu
                85                  90                  95

Thr Phe Gly Gly Gly Thr Lys Val Glu Ile Lys Arg
            100                 105
```

```
<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagggcatta gcgattat                                                 18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Gly Ile Ser Asp Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcaacc                                                            9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Thr
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
caacagctta atacttaccc actcact                                       27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Leu Asn Thr Tyr Pro Leu Thr
1               5

<210> SEQ ID NO 49
<211> LENGTH: 360
<212> TYPE: DNA
<213> ORGANISM: Artificial Sequence
```

<220> FEATURE:
<223> OTHER INFORMATION: Synthetic

<400> SEQUENCE: 49

```
caggtgcagc tggtggagtc tgggggaggc gtggtccagc ctgggaggtc cctgagactc    60
tcctgtgcag cgtctggatt caccttcagt agctttggca tgcactgggt ccgccaggct   120
ccaggcaagg ggctggagtg ggtggcagtt atatggtatg ttgaaattaa taaataccat   180
gcagactccg tgaagggccg attcaccatc tccagagacg attccaagaa cacggtatat   240
ctgcaaatga acagcctgag agccgaggac acggctgtgt attactgtgc gagagactgg   300
aacgacgggg actacggtat ggacgtctgg ggccaaggga ccacggtcac cgtctcctca   360
```

<210> SEQ ID NO 50
<211> LENGTH: 120
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Trp Tyr Val Glu Ile Asn Lys Tyr His Ala Asp Ser Val
    50                  55                  60

Lys Gly Arg Phe Thr Ile Ser Arg Asp Asp Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Trp Asn Asp Gly Asp Tyr Gly Met Asp Val Trp Gly Gln
            100                 105                 110

Gly Thr Thr Val Thr Val Ser Ser
        115                 120
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggattcacct tcagtagctt tggc                                           24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Phe Thr Phe Ser Ser Phe Gly
1               5
```

<210> SEQ ID NO 53
<211> LENGTH: 24

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atatggtatg ttgaaattaa taaa                                           24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Trp Tyr Val Glu Ile Asn Lys
1               5

<210> SEQ ID NO 55
<211> LENGTH: 39
<212> TYPE: DNA
<213> ORGANISM: Artificial Sequence
<220> FEATURE:
<223> OTHER INFORMATION: Synthetic

<400> SEQUENCE: 55
gcgagagact ggaacgacgg ggactacggt atggacgtc                           39

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

Ala Arg Asp Trp Asn Asp Gly Asp Tyr Gly Met Asp Val
1               5                   10

<210> SEQ ID NO 57
<211> LENGTH: 324
<212> TYPE: DNA
<213> ORGANISM: Artificial Sequence
<220> FEATURE:
<223> OTHER INFORMATION: Synthetic

<400> SEQUENCE: 57
gacatccagt tgacccagtc tccatccttc ctgtctgcat ctgtaggaga cagagtcacc    60
atcacttgct gggccagtca gggcattagc agttttttag cctggtatca gcaaaaagca   120
gggaaagccc cgaggctcct gatctatgct gcatccactt tgcaaactgg ggtcccatca   180
aggttcagcg gcagtggatc tgggacagaa ttcactctca caatcagcag cctgcagcct   240
ggagattttg caacttatca ctgtcaacag cttaatagtt acccgtacac ttttggccag   300
gggaccaagc tggagatcaa acga                                          324

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Phe
            20                  25                  30

Leu Ala Trp Tyr Gln Gln Lys Ala Gly Lys Ala Pro Arg Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Gly Asp Phe Ala Thr Tyr His Cys Gln Gln Leu Asn Ser Tyr Pro Tyr
                85                  90                  95

Thr Phe Gly Gln Gly Thr Lys Leu Glu Ile Lys Arg
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggcatta gcagtttt                                                    18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

```
Gln Gly Ile Ser Ser Phe
1               5
```

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc                                                               9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

```
Ala Ala Ser
1
```

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagctta atagttaccc gtacact                                              27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Leu Asn Ser Tyr Pro Tyr Thr
1               5

<210> SEQ ID NO 65
<211> LENGTH: 369
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtacagc ctggggggtc cctgagactc          60
tcctgtgcag cctctggatt caccttcagt aactacgaca tacactgggt ccgccaagct         120
acaggaaaag gtctggagtg ggtctcagct attggtcctg ctggtgacac atactattca         180
gactccgtaa agggccgatt caccatctcc agagaagatg ccaagaactc cttgtatctt         240
caaatgagca gcctgagagc cggggacacg gctgtttatt actgtgcaag cgaggggata         300
gcagttcgtc cggacgacta ctacggtatg gacgtctggg gccaagggac cacggtcacc         360
gtctccgcc                                                                369

<210> SEQ ID NO 66
<211> LENGTH: 123
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Ser Asp Ser Val Lys
    50                  55                  60

Gly Arg Phe Thr Ile Ser Arg Glu Asp Ala Lys Asn Ser Leu Tyr Leu
65                  70                  75                  80

Gln Met Ser Ser Leu Arg Ala Gly Asp Thr Ala Val Tyr Tyr Cys Ala
                85                  90                  95

Ser Glu Gly Ile Ala Val Arg Pro Asp Asp Tyr Tyr Gly Met Asp Val
            100                 105                 110

Trp Gly Gln Gly Thr Thr Val Thr Val Ser Ala
        115                 120

<210> SEQ ID NO 67
<211> LENGTH: 24
<212> TYPE: DNA

```
<213> ORGANISM: Artificial Sequence
<220> FEATURE:
<223> OTHER INFORMATION: Synthetic

<400> SEQUENCE: 67
ggattcacct tcagtaacta cgac                                              24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Asn Tyr Asp
 1               5

<210> SEQ ID NO 69
<211> LENGTH: 21
<212> TYPE: DNA
<213> ORGANISM: Artificial Sequence
<220> FEATURE:
<223> OTHER INFORMATION: Synthetic

<400> SEQUENCE: 69
attggtcctg ctggtgacac a                                                 21

<210> SEQ ID NO 70
<211> LENGTH: 7
<212> TYPE: PRT
<213> ORGANISM: Artificial Sequence
<220> FEATURE:
<223> OTHER INFORMATION: Synthetic

<400> SEQUENCE: 70

Ile Gly Pro Ala Gly Asp Thr
 1               5

<210> SEQ ID NO 71
<211> LENGTH: 51
<212> TYPE: DNA
<213> ORGANISM: Artificial Sequence
<220> FEATURE:
<223> OTHER INFORMATION: Synthetic

<400> SEQUENCE: 71
gcaagcgagg ggatagcagt tcgtccggac gactactacg gtatggacgt c                51

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Ala Ser Glu Gly Ile Ala Val Arg Pro Asp Asp Tyr Tyr Gly Met Asp
 1               5                  10                  15
Val

<210> SEQ ID NO 73
<211> LENGTH: 324
<212> TYPE: DNA
<213> ORGANISM: Artificial Sequence
<220> FEATURE:
```

<223> OTHER INFORMATION: Synthetic

<400> SEQUENCE: 73

```
gacatccagt tgacccagtc tccatccttc ctgtctgcat ctgtaggaga cagagtcacc    60
atcacttgct gggccagtca ggacattacc agttatttag cctggtatca gaaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg cagcttatta ctgtcaacag cttaatagtt acccgctcac tttcggcgga   300
gggaccaagg tggagatcaa acga                                          324
```

<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Asp Ile Gln Leu Thr Gln Ser Pro Ser Phe Leu Ser Ala Ser Val Gly
1               5                   10                  15
Asp Arg Val Thr Ile Thr Cys Trp Ala Ser Gln Asp Ile Thr Ser Tyr
            20                  25                  30
Leu Ala Trp Tyr Gln Lys Lys Pro Gly Lys Ala Pro Lys Leu Leu Ile
        35                  40                  45
Tyr Ala Ala Ser Thr Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Ala Tyr Tyr Cys Gln Gln Leu Asn Ser Tyr Pro Leu
                85                  90                  95
Thr Phe Gly Gly Gly Thr Lys Val Asp Ile Lys Arg
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
caggacatta ccagttat                                                  18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Asp Ile Thr Ser Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc                                                                  9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacagctta atagttaccc gctcact                                             27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Leu Asn Ser Tyr Pro Leu Thr
1               5

<210> SEQ ID NO 81
<211> LENGTH: 381
<212> TYPE: DNA
<213> ORGANISM: Artificial Sequence
<220> FEATURE:
<223> OTHER INFORMATION: Synthetic

<400> SEQUENCE: 81
gaggtgcagc tgttggagtc tgggggagac ttggtacagc ctggggggtc cctgagactc         60
tcctgtgcaa cctctggatt cagttttagt agtgatgcca tgaactgggt ccgccaggct        120
ccagggaagg gcctggagtg gtctcaggt attagtggta gtggtggtaa cacatactac         180
gcagactccg tgaagggccg gttcaccatc tccagagaca tttccaagag cacgctgtct        240
ctgcaaatga acagcctgag agccgaggac acggccgtat attattgtgc gaaagagggt       300
actaatatgg ttcggggagt tgttatggag acaacggta tggacgtctg gggccaaggg        360
accacggtca ccgtctccgc c                                                 381

<210> SEQ ID NO 82
<211> LENGTH: 127
<212> TYPE: PRT
<213> ORGANISM: Artificial Sequence
<220> FEATURE:
<223> OTHER INFORMATION: Synthetic

<400> SEQUENCE: 82

Glu Val Gln Leu Leu Glu Ser Gly Gly Asp Leu Val Gln Pro Gly Gly
1               5                   10                  15

```
Ser Leu Arg Leu Ser Cys Ala Thr Ser Gly Phe Ser Phe Ser Ser Asp
         20                  25                  30

Ala Met Asn Trp Val Arg Gln Ala Pro Gly Lys Gly Leu Glu Trp Val
     35                  40                  45

Ser Gly Ile Ser Gly Ser Gly Gly Asn Thr Tyr Tyr Ala Asp Ser Val
 50                  55                  60

Lys Gly Arg Phe Thr Ile Ser Arg Asp Ile Ser Lys Ser Thr Leu Ser
 65                  70                  75                  80

Leu Gln Met Asn Ser Leu Arg Ala Glu Asp Thr Ala Val Tyr Tyr Cys
                 85                  90                  95

Ala Lys Glu Gly Thr Asn Met Val Arg Gly Val Val Met Glu Asp Asn
            100                 105                 110

Gly Met Asp Val Trp Gly Gln Gly Thr Thr Val Thr Val Ser Ala
        115                 120                 125
```

```
<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcagtt ttagtagtga tgcc                                    24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Ser Phe Ser Ser Asp Ala
1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attagtggta gtggtggtaa caca                                    24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Gly Ser Gly Gly Asn Thr
1               5

<210> SEQ ID NO 87
<211> LENGTH: 60
<212> TYPE: DNA
<213> ORGANISM: Artificial Sequence
<220> FEATURE:
<223> OTHER INFORMATION: Synthetic
```

<400> SEQUENCE: 87
gcgaaagagg gtactaatat ggttcgggga gttgttatgg aggacaacgg tatggacgtc    60

<210> SEQ ID NO 88
<211> LENGTH: 20
<212> TYPE: PRT
<213> ORGANISM: Artificial Sequence
<220> FEATURE:
<223> OTHER INFORMATION: Synthetic

<400> SEQUENCE: 88

Ala Lys Glu Gly Thr Asn Met Val Arg Gly Val Val Met Glu Asp Asn
1               5                   10                  15

Gly Met Asp Val
            20

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gacatccaga tgacccagtc gccatcttcc gtgtctgcat ctgtgggaga cagagtcacc    60
atcacttgtc gggcgagtca gggtattagc gactacttag cctggtatca gcagaaacca   120
ggaaaagccc ctaaactcct gatctatgct gcatccagtt tgcaaagtgg ggtcccatcc   180
aggttcagcg gccgtggctc tgggacagat ttcactctca ccatcagcac cctgcagcct   240
gaagattttg caacttacta ttgtcaacag gctaacagtt tcccgctcac tttcggcgga   300
gggaccaagg tggagatcaa acga                                         324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asp Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Asp Ile Lys Arg
            100                 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagggtatta gcgactac                                                       18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Gly Ile Ser Asp Tyr
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                                  9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaggcta acagtttccc gctcact                                             27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Ala Asn Ser Phe Pro Leu Thr
1               5

<210> SEQ ID NO 97
<211> LENGTH: 357
<212> TYPE: DNA
<213> ORGANISM: Artificial Sequence
<220> FEATURE:
<223> OTHER INFORMATION: Synthetic

<400> SEQUENCE: 97

```
caggtgcagc tggtggagtc tgggggaggc gtggtccagc ctgggaggtc cctgagactc    60
tcctgtgcag cgtctggatt caccttcaat aactatggca tgcactgggt ccgccaggct   120
ccaggcaagg ggctggcgtg gtggcagtt atgtggtata gtgaaagtca taaatactat   180
gcagactccg tgaagggccg attcaccatc tccagagaca attccaagaa cacgctgtat   240
ctggaaatga acagcctgag agtcgaggac acggctatat attactgtgc gagagatctc   300
ggtgaccccg atgcttttga tatctggggc caaggacaa tggtcaccgt ctcttca      357
```

<210> SEQ ID NO 98
<211> LENGTH: 119
<212> TYPE: PRT
<213> ORGANISM: Artificial Sequence
<220> FEATURE:
<223> OTHER INFORMATION: Synthetic

<400> SEQUENCE: 98

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Ala Trp Val
        35                  40                  45

Ala Val Met Trp Tyr Ser Glu Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Val Glu Asp Thr Ala Ile Tyr Tyr Cys
                85                  90                  95

Ala Arg Asp Leu Gly Asp Pro Asp Ala Phe Asp Ile Trp Gly Gln Gly
            100                 105                 110

Thr Met Val Thr Val Ser Ser
        115
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcaccct tcaataacta tggc                                          24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Asn Asn Tyr Gly
1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
atgtggtata gtgaaagtca taaa                                            24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Met Trp Tyr Ser Glu Ser His Lys
1               5

<210> SEQ ID NO 103
<211> LENGTH: 36
<212> TYPE: DNA
<213> ORGANISM: Artificial Sequence
<220> FEATURE:
<223> OTHER INFORMATION: Synthetic

<400> SEQUENCE: 103
gcgagagatc tcggtgaccc cgatgctttt gatatc                               36

<210> SEQ ID NO 104
<211> LENGTH: 12
<212> TYPE: PRT
<213> ORGANISM: Artificial Sequence
<220> FEATURE:
<223> OTHER INFORMATION: Synthetic

<400> SEQUENCE: 104

Ala Arg Asp Leu Gly Asp Pro Asp Ala Phe Asp Ile
1               5                   10

<210> SEQ ID NO 105
<211> LENGTH: 324
<212> TYPE: DNA
<213> ORGANISM: Artificial Sequence
<220> FEATURE:
<223> OTHER INFORMATION: Synthetic

<400> SEQUENCE: 105
gacatccagt tgacccagtc tccatccttc ctgtctgcat ctgtaggaga cagagtcacc      60
atcacttgct gggccagtca gggcattagc agttatttag cctggtatca gcaaaaacca     120
gggaaagccc ctaagctcct gatttatggt gcatccactt tgcaaagtgg ggtcccatca     180
aggttcagcg gcagtggatc tgggacagaa ttcactctca caatcagcag cctgcagcct     240
gaagattttg caacttatta ctgtcaacag cttaatagtt accctctcac cttcggcgga     300
gggaccaagg tggagatcaa acga                                           324

<210> SEQ ID NO 106
<211> LENGTH: 108
<212> TYPE: PRT
<213> ORGANISM: Artificial Sequence
<220> FEATURE:
<223> OTHER INFORMATION: Synthetic

<400> SEQUENCE: 106

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr

```
              20                  25                  30
Leu Ala Trp Tyr Gln Gln Lys Pro Gly Lys Ala Pro Lys Leu Leu Ile
             35                  40                  45
Tyr Gly Ala Ser Thr Leu Gln Ser Gly Val Pro Ser Arg Phe Ser Gly
         50                  55                  60
Ser Gly Ser Gly Thr Glu Phe Thr Leu Thr Ile Ser Ser Leu Gln Pro
 65                  70                  75                  80
Glu Asp Phe Ala Thr Tyr Tyr Cys Gln Gln Leu Asn Ser Tyr Pro Leu
                 85                  90                  95
Thr Phe Gly Gly Gly Thr Lys Val Glu Ile Lys Arg
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggcatta gcagttat                                              18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

```
Gln Gly Ile Ser Ser Tyr
 1               5
```

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 ggtgcatcc                                                         9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

```
Gly Ala Ser
 1
```

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacagctta atagttaccc tctcacc                                    27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Leu Asn Ser Tyr Pro Leu Thr
1               5

<210> SEQ ID NO 113
<211> LENGTH: 375
<212> TYPE: DNA
<213> ORGANISM: Artificial Sequence
<220> FEATURE:
<223> OTHER INFORMATION: Synthetic

<400> SEQUENCE: 113
caggtgcagc tggtggagtc tgggggaggc gtggtccagc ctggagagtc cctgagactc      60
tcctgtgcag cctctggatt caccttcagt agctatggca tgcactgggt ccgccaggct     120
ccaggcaagg gctggagtg gtggcaggt atgtcatatg atggaagtag taaatactat      180
gaagactccg tgaagggccg attcaccatc tccagagaca attccaagaa cacgctgaat     240
ctgcaaatga acagcctgag agttgaggac acggctgtgt attactgtgc gaaagaaagg     300
gactacgttg agtacgtaga ctcctactac ggtatggacg tctggggcca agggaccacg     360
gtcaccgtct ccgcc                                                      375

<210> SEQ ID NO 114
<211> LENGTH: 125
<212> TYPE: PRT
<213> ORGANISM: Artificial Sequence
<220> FEATURE:
<223> OTHER INFORMATION: Synthetic

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Gly Met Ser Tyr Asp Gly Ser Ser Lys Tyr Tyr Glu Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Val Glu Asp Thr Ala Val Tyr Tyr Cys
                85                  90                  95

Ala Lys Glu Arg Asp Tyr Val Glu Tyr Val Asp Ser Tyr Tyr Gly Met
            100                 105                 110

Asp Val Trp Gly Gln Gly Thr Thr Val Thr Val Ser Ala
        115                 120                 125

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct tcagtagcta tggc                                           24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Ser Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atgtcatatg atggaagtag taaa                                           24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Met Ser Tyr Asp Gly Ser Ser Lys
1               5

<210> SEQ ID NO 119
<211> LENGTH: 54
<212> TYPE: DNA
<213> ORGANISM: Artificial Sequence
<220> FEATURE:
<223> OTHER INFORMATION: Synthetic

<400> SEQUENCE: 119
gcgaaagaaa gggactacgt tgagtacgta gactcctact acggtatgga cgtc          54

<210> SEQ ID NO 120
<211> LENGTH: 18
<212> TYPE: PRT
<213> ORGANISM: Artificial Sequence
<220> FEATURE:
<223> OTHER INFORMATION: Synthetic

<400> SEQUENCE: 120

Ala Lys Glu Arg Asp Tyr Val Glu Tyr Val Asp Ser Tyr Tyr Gly Met
1               5                   10                  15

Asp Val

<210> SEQ ID NO 121
<211> LENGTH: 324
<212> TYPE: DNA
<213> ORGANISM: Artificial Sequence
<220> FEATURE:
<223> OTHER INFORMATION: Synthetic

<400> SEQUENCE: 121

```
gccatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaaggtcct aatctatgct gcatccagtt tacaaagtgg ggtcccatca   180
aggttcagcg gcagtggatc tggaacagtt ttcactctca ccatcagcag cctgcagcct   240
gaagattttg caacttatta ctgtctacaa gattacaatt acccgctcac tttcggcgga   300
gggaccaagg tggagatcaa acga                                          324
```

<210> SEQ ID NO 122
<211> LENGTH: 108
<212> TYPE: PRT
<213> ORGANISM: Artificial Sequence
<220> FEATURE:
<223> OTHER INFORMATION: Synthetic

<400> SEQUENCE: 122

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys Arg
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123

```
cagggcatta gaaatgat                                                  18
```

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

```
Gln Gly Ile Arg Asn Asp
1               5
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125

```
gctgcatcc                                                             9
```

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Ala Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
ctacaagatt acaattaccc gctcact                                          27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Leu Gln Asp Tyr Asn Tyr Pro Leu Thr
1               5

<210> SEQ ID NO 129
<211> LENGTH: 375
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc tgggggaggt gtggtacggc ctggggggtc cctgagactc        60
tcctgtgcag cctctggatt cacctttgat gattatggca tgagctgggt ccgccaattt       120
ccagggaagg ggctggagtg ggtctctagt attgatggaa atggtggtaa cacaggttat       180
tcagactctg tgaagggccg attcaccatc tccagagaca cgccaaaaa ctccctgcat        240 ctgcaaatga acagtctgag agccgaggac acggccttgt atcactgtgc gagagatccc       300
gattatgatt ccgtttgggg gaattatcgt cccctttgact actggggcca gggaaccctg     360
gtcaccgtct cctca                                                       375

<210> SEQ ID NO 130
<211> LENGTH: 125
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Phe Pro Gly Lys Gly Leu Glu Trp Val
                35                  40                  45

Ser Ser Ile Asp Gly Asn Gly Gly Asn Thr Gly Tyr Ser Asp Ser Val
 50                  55                  60

Lys Gly Arg Phe Thr Ile Ser Arg Asp Asn Ala Lys Asn Ser Leu His
 65                  70                  75                  80

Leu Gln Met Asn Ser Leu Arg Ala Glu Asp Thr Ala Leu Tyr His Cys
                 85                  90                  95

Ala Arg Asp Pro Asp Tyr Asp Ser Val Trp Gly Asn Tyr Arg Pro Phe
            100                 105                 110

Asp Tyr Trp Gly Gln Gly Thr Leu Val Thr Val Ser Ser
        115                 120                 125

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct ttgatgatta tggc                                          24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Asp Asp Tyr Gly
 1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attgatggaa atggtggtaa caca                                          24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Asp Gly Asn Gly Gly Asn Thr
 1               5

<210> SEQ ID NO 135
<211> LENGTH: 54
<212> TYPE: DNA
<213> ORGANISM: Artificial Sequence
<220> FEATURE:
<223> OTHER INFORMATION: Synthetic

<400> SEQUENCE: 135
gcgagagatc ccgattatga ttccgtttgg gggaattatc gtcccttrga ctac         54

<210> SEQ ID NO 136
<211> LENGTH: 18
<212> TYPE: PRT
<213> ORGANISM: Artificial Sequence
<220> FEATURE:
<223> OTHER INFORMATION: Synthetic

<400> SEQUENCE: 136

Ala Arg Asp Pro Asp Tyr Asp Ser Val Trp Gly Asn Tyr Arg Pro Phe
1               5                   10                  15

Asp Tyr

<210> SEQ ID NO 137
<211> LENGTH: 342
<212> TYPE: DNA
<213> ORGANISM: Artificial Sequence
<220> FEATURE:
<223> OTHER INFORMATION: Synthetic

<400> SEQUENCE: 137
gatattgtga tgactcagtc tccagactcc ctggctgtgt ctctgggcga gagggccacc      60
atcaactgca gtccagcca gagtgtttta tccagctcca acgataacaa ctacttagct     120
tggttccagc agaaaccagg acagcctcct aacctactca tttactgggc atccacccgg     180
gattccgggg tccctgaccg attcagtgcc agcgggtctg ggacagattt cacccctcgcc    240 atcagcagcc tgcaggctga agatgtggca gtttattact gtcaccaata ttatagttct     300
cctccgacgt tcggccaagg gaccaaggtg gagatcaaac ga                        342

<210> SEQ ID NO 138
<211> LENGTH: 114
<212> TYPE: PRT
<213> ORGANISM: Artificial Sequence
<220> FEATURE:
<223> OTHER INFORMATION: Synthetic

<400> SEQUENCE: 138

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Ser
                20                  25                  30

Ser Asn Asp Asn Asn Tyr Leu Ala Trp Phe Gln Gln Lys Pro Gly Gln
            35                  40                  45

Pro Pro Asn Leu Leu Ile Tyr Trp Ala Ser Thr Arg Asp Ser Gly Val
        50                  55                  60

Pro Asp Arg Phe Ser Ala Ser Gly Ser Gly Thr Asp Phe Thr Leu Ala
65                  70                  75                  80

Ile Ser Ser Leu Gln Ala Glu Asp Val Ala Val Tyr Tyr Cys His Gln
                85                  90                  95

Tyr Tyr Ser Ser Pro Pro Thr Phe Gly Gln Gly Thr Lys Val Glu Ile
            100                 105                 110

Lys Arg

<210> SEQ ID NO 139
<211> LENGTH: 36
<212> TYPE: DNA
<213> ORGANISM: Artificial Sequence
<220> FEATURE:
<223> OTHER INFORMATION: Synthetic

<400> SEQUENCE: 139
cagagtgttt tatccagctc caacgataac aactac        36

<210> SEQ ID NO 140
<211> LENGTH: 12
<212> TYPE: PRT
<213> ORGANISM: Artificial Sequence
<220> FEATURE:
<223> OTHER INFORMATION: Synthetic

<400> SEQUENCE: 140

Gln Ser Val Leu Ser Ser Ser Asn Asp Asn Asn Tyr
1               5                   10

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 tgggcatcc        9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Trp Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caccaatatt atagttctcc tccgacg        27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

His Gln Tyr Tyr Ser Ser Pro Pro Thr
1               5

<210> SEQ ID NO 145
<211> LENGTH: 372
<212> TYPE: DNA
<213> ORGANISM: Artificial Sequence
<220> FEATURE:
<223> OTHER INFORMATION: Synthetic

<400> SEQUENCE: 145
caggtgcagc tgcaggagtc gggcccagga ctggtgaagc cttcacagac cctgtccctc        60

```
acctgcactg tctctggtgg ctccattaac agtggtggtt attactggag ctggatccgc    120
cagcacccag ggaagggcct ggagtggatt gggtacatct cttacagtgg gaataccaac    180
tacaacccgt ccctcaagag tcgagttacc atatcagtag acacgtctaa gaaccagttc    240
tccctgacac tgacctctgt gactgccgcg gacacggccg tgtattactg tgcgagagac    300
agtgacgtgg atacaggtct ggttgatggt tttgatgtct ggggccaagg aacaatggtc    360
accgtctctt ca                                                        372
```

```
<210> SEQ ID NO 146
<211> LENGTH: 124
<212> TYPE: PRT
<213> ORGANISM: Artificial Sequence
<220> FEATURE:
<223> OTHER INFORMATION: Synthetic

<400> SEQUENCE: 146
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Asn Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Ser Tyr Ser Gly Asn Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Thr Ser Val Thr Ala Ala Asp Thr Ala Val Tyr Tyr
                85                  90                  95

Cys Ala Arg Asp Ser Asp Val Asp Thr Gly Leu Val Asp Gly Phe Asp
            100                 105                 110

Val Trp Gly Gln Gly Thr Met Val Thr Val Ser Ser
        115                 120

```
<210> SEQ ID NO 147
<211> LENGTH: 30
<212> TYPE: DNA
<213> ORGANISM: Artificial Sequence
<220> FEATURE:
<223> OTHER INFORMATION: Synthetic

<400> SEQUENCE: 147
ggtggctcca ttaacagtgg tggttattac                                      30

<210> SEQ ID NO 148
<211> LENGTH: 10
<212> TYPE: PRT
<213> ORGANISM: Artificial Sequence
<220> FEATURE:
<223> OTHER INFORMATION: Synthetic

<400> SEQUENCE: 148
```

Gly Gly Ser Ile Asn Ser Gly Gly Tyr Tyr
1               5                   10

```
<210> SEQ ID NO 149
<211> LENGTH: 21
<212> TYPE: DNA
<213> ORGANISM: Artificial Sequence
<220> FEATURE:
<223> OTHER INFORMATION: Synthetic
```

<400> SEQUENCE: 149
atctcttaca gtgggaatac c                                              21

<210> SEQ ID NO 150
<211> LENGTH: 7
<212> TYPE: PRT
<213> ORGANISM: Artificial Sequence
<220> FEATURE:
<223> OTHER INFORMATION: Synthetic

<400> SEQUENCE: 150

Ile Ser Tyr Ser Gly Asn Thr
1               5

<210> SEQ ID NO 151
<211> LENGTH: 48
<212> TYPE: DNA
<213> ORGANISM: Artificial Sequence
<220> FEATURE:
<223> OTHER INFORMATION: Synthetic

<400> SEQUENCE: 151
gcgagagaca gtgacgtgga tacaggtctg gttgatggtt ttgatgtc                 48

<210> SEQ ID NO 152
<211> LENGTH: 16
<212> TYPE: PRT
<213> ORGANISM: Artificial Sequence
<220> FEATURE:
<223> OTHER INFORMATION: Synthetic

<400> SEQUENCE: 152

Ala Arg Asp Ser Asp Val Asp Thr Gly Leu Val Asp Gly Phe Asp Val
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gatattgtga tgacccagtc tccatcttcc gtgtctgcat ctgtaggaga cagagtcacc    60
atcacttgcc gggcgagtca gggtgttagc agctggttag cctggtatca gcagaaacca  120
gggaaagccc ccaagctcct gatttatact acatccagtt tgcaaagtgg ggtcccatca  180
aggttcagcg gcagtggatc tgggacagat ttcactctca ccatcagcag cctgcagcct  240
gaggattttg caacttacta ttgtcaacag tctaacagtt ttccattcac tttcggccct  300
gggaccaagg tggagatcaa a                                             321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Pro Gly Lys Ala Pro Lys Leu Leu Ile
            35                  40                  45

Tyr Thr Thr Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Phe Pro Phe
                85                  90                  95

Thr Phe Gly Pro Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagggtgtta gcagctgg                                            18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Gly Val Ser Ser Trp
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 actacatcc                                                       9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Thr Thr Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacagtcta acagttttcc attcact                                  27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Ser Asn Ser Phe Pro Phe Thr
1               5

<210> SEQ ID NO 161
<211> LENGTH: 372
<212> TYPE: DNA
<213> ORGANISM: Artificial Sequence
<220> FEATURE:
<223> OTHER INFORMATION: Synthetic

<400> SEQUENCE: 161
gaggtgcagc tggtggagtc tgggggaggc ttggtacagc ctggggggtc cctaagactc      60
tcctgtgcag cctctggatt ctccgtcagt tactacgaca tgcactgggt ccgccaagtt     120
acaggaaaag gtctggagtg ggtctcagct attggtcctg caggtgacac atattaccca     180
ggctccgtga agggccgatt caccatctcc agagaagatg ccacgaactc cttatatctt     240
caaatacaca gcctgggagc cggggacacg gctgtgtatt actgtgcaag agaggggct      300 atagcagctc gtccggacga ctactacggt atggacgtct ggggccaagg gaccacggtc     360
accgtctcct ca                                                         372

<210> SEQ ID NO 162
<211> LENGTH: 124
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Val Ser Tyr Tyr
            20                  25                  30

Asp Met His Trp Val Arg Gln Val Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asp Ala Thr Asn Ser Leu Tyr Leu
65                  70                  75                  80

Gln Ile His Ser Leu Gly Ala Gly Asp Thr Ala Val Tyr Tyr Cys Ala
                85                  90                  95

Arg Glu Gly Ala Ile Ala Ala Arg Pro Asp Asp Tyr Tyr Gly Met Asp
            100                 105                 110

Val Trp Gly Gln Gly Thr Thr Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163

```
ggattctccg tcagttacta cgac                                              24
```

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Ser Val Ser Tyr Tyr Asp
1               5

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165

```
attggtcctg caggtgacac a                                                 21
```

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Ile Gly Pro Ala Gly Asp Thr
1               5

<210> SEQ ID NO 167
<211> LENGTH: 54
<212> TYPE: DNA
<213> ORGANISM: Artificial Sequence
<220> FEATURE:
<223> OTHER INFORMATION: Synthetic

<400> SEQUENCE: 167

```
gcaagagagg gggctatagc agctcgtccg gacgactact acggtatgga cgtc             54
```

<210> SEQ ID NO 168
<211> LENGTH: 18
<212> TYPE: PRT
<213> ORGANISM: Artificial Sequence
<220> FEATURE:
<223> OTHER INFORMATION: Synthetic

<400> SEQUENCE: 168

Ala Arg Glu Gly Ala Ile Ala Ala Arg Pro Asp Asp Tyr Tyr Gly Met
1               5                   10                  15

Asp Val

<210> SEQ ID NO 169
<211> LENGTH: 324
<212> TYPE: DNA
<213> ORGANISM: Artificial Sequence
<220> FEATURE:
<223> OTHER INFORMATION: Synthetic

<400> SEQUENCE: 169

```
gacatccagt tgacccagtc tccatccttc ctgtctgcat ctgtaggaga cagagtcacc       60
```
atcacttgct gggccagtca ggacattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacaa cttaatagtt acccgctcac tttcggcgga    300
gggaccaagg tggagatcaa acga                                          324

```
<210> SEQ ID NO 170
<211> LENGTH: 108
<212> TYPE: PRT
<213> ORGANISM: Artificial Sequence
<220> FEATURE:
<223> OTHER INFORMATION: Synthetic

<400> SEQUENCE: 170
```

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg
            100                 105

```
<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
```
caggacatta gcagttat                                                  18

```
<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172
```

Gln Asp Ile Ser Ser Tyr
1               5

```
<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173
``` gctgcatcc                                                            9

-continued

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacaactta atagttaccc gctcact                                         27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Leu Asn Ser Tyr Pro Leu Thr
1               5

<210> SEQ ID NO 177
<211> LENGTH: 363
<212> TYPE: DNA
<213> ORGANISM: Artificial Sequence
<220> FEATURE:
<223> OTHER INFORMATION: Synthetic

<400> SEQUENCE: 177
gaggtgcagc tggtggagtc tgggggaggc ttggtacagc ctggcaggtc cctgagactc     60
tcctgtgcag cctctggatt cacctttggt gattatgcca tgcactgggt ccggcaagct    120
ccagggaagg gcctggagtg ggtctcaggt attaatttga atagtggcac cataggctat    180
gcggactctg tgaagggccg attcaccatt tcaagagaca acgccaagaa ctccctgtat    240
ctgcaaatga acagtctgag agctgaggac acggccttct attactgtgc aaaagatata    300
gacggctact atcactacgc tatggacgtc tggggccaag gaccacgggt caccgtctcc    360
tca                                                                  363

<210> SEQ ID NO 178
<211> LENGTH: 121
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Gly Asp Tyr
            20                  25                  30

Ala Met His Trp Val Arg Gln Ala Pro Gly Lys Gly Leu Glu Trp Val

```
                35                  40                  45
Ser Gly Ile Asn Leu Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr Tyr Cys
                85                  90                  95

Ala Lys Asp Ile Asp Gly Tyr Tyr His Tyr Ala Met Asp Val Trp Gly
            100                 105                 110

Gln Gly Thr Thr Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct ttggtgatta tgcc                                      24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Gly Asp Tyr Ala
1               5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
attaatttga atagtggcac cata                                      24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Asn Leu Asn Ser Gly Thr Ile
1               5

<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183
gcaaaagata tagacggcta ctatcactac gctatggacg tc                  42
```

```
<210> SEQ ID NO 184
<211> LENGTH: 14
<212> TYPE: PRT
<213> ORGANISM: Artificial Sequence
<220> FEATURE:
<223> OTHER INFORMATION: Synthetic

<400> SEQUENCE: 184

Ala Lys Asp Ile Asp Gly Tyr Tyr His Tyr Ala Met Asp Val
1               5                   10

<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185
gacatccagt tgacccagtc tccatccttc ctgtctgcat ctgtaggaga cagagtcacc      60
atcacttgct gggccagtca gggcattagc agttatttag cctggtatca gcaaaaacca     120
gggaaagccc ctaaactcct gatctatgat gcatccactt tggaaagtgg ggtcccatca     180
aggttcagcg gcagtggatc tgggacagaa ttcactctca caatcagcaa cctgcagcct     240
gaagattttg caacttatta ctgtcaacag gttaatagtt accctctcac tttcggcgga     300
gggaccaagg tggaaatcaa acga                                            324

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

Asp Val Val Met Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Val Asn Ser Tyr Pro Leu
                85                  90                  95

Thr Phe Gly Gly Gly Thr Lys Val Glu Ile Lys Arg
            100                 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagggcatta gcagttat                                                    18
```

```
<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Gly Ile Ser Ser Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gatgcatcc                                                                 9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Asp Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacaggtta atagttaccc tctcact                                            27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Val Asn Ser Tyr Pro Leu Thr
1               5

<210> SEQ ID NO 193
<211> LENGTH: 354
<212> TYPE: DNA
<213> ORGANISM: Artificial Sequence
<220> FEATURE:
<223> OTHER INFORMATION: Synthetic

<400> SEQUENCE: 193
caggtgcagc tggtggagtc tgggggaggc gtggtccagc ctggagggtc cctgagactc        60
tcctgtgcag cgtctggatt caccttcatt aactatggca tacattgggt ccgccagggt       120
ccaggcaagg ggctggagtg ggtggcagtt atatggtatg atggaagtaa tgaatggtat       180
gcagactccg tgaagggccg attcaccatc tccagagaca attccaagaa cacggtgtat       240
```

```
ctggaaatga ataaactgag agccgaggac acggctgtgt attactgtgc gagagaagaa    300
gaggactacg gtatggacgt ctggggtcaa gggaccacgg tcaccgtctc ctca          354
```

<210> SEQ ID NO 194
<211> LENGTH: 118
<212> TYPE: PRT
<213> ORGANISM: Artificial Sequence
<220> FEATURE:
<223> OTHER INFORMATION: Synthetic

<400> SEQUENCE: 194

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ile Asn Tyr
            20                  25                  30

Gly Ile His Trp Val Arg Gln Gly Pro Gly Lys Gly Leu Glu Trp Val
        35                  40                  45

Ala Val Ile Trp Tyr Asp Gly Ser Asn Glu Trp Tyr Ala Asp Ser Val
    50                  55                  60

Lys Gly Arg Phe Thr Ile Ser Arg Asp Asn Ser Lys Asn Thr Val Tyr
65                  70                  75                  80

Leu Glu Met Asn Lys Leu Arg Ala Glu Asp Thr Ala Val Tyr Tyr Cys
                85                  90                  95

Ala Arg Glu Glu Glu Asp Tyr Gly Met Asp Val Trp Gly Gln Gly Thr
            100                 105                 110

Thr Val Thr Val Ser Ser
        115
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
ggattcacct tcattaacta tggc                                           24
```

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Gly Phe Thr Phe Ile Asn Tyr Gly
1               5
```

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197

```
atatggtatg atggaagtaa tgaa                                           24
```

<210> SEQ ID NO 198
<211> LENGTH: 8

```
<212> TYPE: PRT
<213> ORGANISM: Artificial Sequence
<220> FEATURE:
<223> OTHER INFORMATION: Synthetic

<400> SEQUENCE: 198

Ile Trp Tyr Asp Gly Ser Asn Glu
1               5

<210> SEQ ID NO 199
<211> LENGTH: 33
<212> TYPE: DNA
<213> ORGANISM: Artificial Sequence
<220> FEATURE:
<223> OTHER INFORMATION: Synthetic

<400> SEQUENCE: 199
gcgagagaag aagaggacta cggtatggac gtc                                33

<210> SEQ ID NO 200
<211> LENGTH: 11
<212> TYPE: PRT
<213> ORGANISM: Artificial Sequence
<220> FEATURE:
<223> OTHER INFORMATION: Synthetic

<400> SEQUENCE: 200

Ala Arg Glu Glu Glu Asp Tyr Gly Met Asp Val
1               5                   10

<210> SEQ ID NO 201
<211> LENGTH: 339
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccagactcc ctggctgtgt ctctgggcga gagggccgcc    60
atcaactgca gtccagcca gagtgtttta tacatctcca acaataacaa ctacttagct   120
tggtaccagc agaaaccagg acagccgcct aagctcctca tttactgggc atccacccgg   180
gaatccgggg tccctgaccg attcagtggc agcgggtctg ggacagattt cactctcacc   240
atcagcagcc tgcaggctga agatgtggct atttattact gtcaacaata ttatagttct   300
cctccgacgt tcggccaagg gaccaaagtg gatatcaaa                          339

<210> SEQ ID NO 202
<211> LENGTH: 113
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Asp Ser Leu Ala Val Ser Leu Gly
1               5                   10                  15

Glu Arg Ala Ala Ile Asn Cys Lys Ser Ser Gln Ser Val Leu Tyr Ile
            20                  25                  30

Ser Asn Asn Asn Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

-continued

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Ile Tyr Tyr Cys Gln Gln
                 85                  90                  95

Tyr Tyr Ser Ser Pro Pro Thr Phe Gly Gln Gly Thr Lys Val Asp Ile
            100                 105                 110

Lys

<210> SEQ ID NO 203
<211> LENGTH: 36
<212> TYPE: DNA
<213> ORGANISM: Artificial Sequence
<220> FEATURE:
<223> OTHER INFORMATION: Synthetic

<400> SEQUENCE: 203
cagagtgttt tatacatctc caacaataac aactac                            36

<210> SEQ ID NO 204
<211> LENGTH: 12
<212> TYPE: PRT
<213> ORGANISM: Artificial Sequence
<220> FEATURE:
<223> OTHER INFORMATION: Synthetic

<400> SEQUENCE: 204

Gln Ser Val Leu Tyr Ile Ser Asn Asn Asn Asn Tyr
 1               5                  10

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 tgggcatcc                                                          9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Trp Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacaatatt atagttctcc tccgacg                                      27

<210> SEQ ID NO 208
<211> LENGTH: 9
<212> TYPE: PRT
<213> ORGANISM: Artificial Sequence
<220> FEATURE:
```

<223> OTHER INFORMATION: Synthetic

<400> SEQUENCE: 208

Gln Gln Tyr Tyr Ser Ser Pro Pro Thr
1               5

<210> SEQ ID NO 209
<211> LENGTH: 357
<212> TYPE: DNA
<213> ORGANISM: Artificial Sequence
<220> FEATURE:
<223> OTHER INFORMATION: Synthetic

<400> SEQUENCE: 209
caggtgcagc tggtggagtc tgggggaggc ttggttaagc ctggagggtc cctgagactc     60
tcctgtgcag cctctggatt caccttcagt gacttcaaca tgggctggat ccgccaggct    120
ccagggaagg ggctggagtg ggtttcacac attagtggta gtggtaatgt catttactac    180
gcagactctg tgaagggccg attcgccatc tccaggaca acggcaagaa ctcactgtat     240
ctgcaagtga acagcctgag agccgaggac acggccgtgt attactgtgc gagagatatc    300
ggtgactccg atgcgtttga tatctggggc caagggacaa tggtcaccgt ctcttca      357

<210> SEQ ID NO 210
<211> LENGTH: 119
<212> TYPE: PRT
<213> ORGANISM: Artificial Sequence
<220> FEATURE:
<223> OTHER INFORMATION: Synthetic

<400> SEQUENCE: 210

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Asn Met Gly Trp Ile Arg Gln Ala Pro Gly Lys Gly Leu Glu Trp Val
        35                  40                  45

Ser His Ile Ser Gly Ser Gly Asn Val Ile Tyr Tyr Ala Asp Ser Val
    50                  55                  60

Lys Gly Arg Phe Ala Ile Ser Arg Asp Asn Gly Lys Asn Ser Leu Tyr
65                  70                  75                  80

Leu Gln Val Asn Ser Leu Arg Ala Glu Asp Thr Ala Val Tyr Tyr Cys
                85                  90                  95

Ala Arg Asp Ile Gly Asp Ser Asp Ala Phe Asp Ile Trp Gly Gln Gly
            100                 105                 110

Thr Met Val Thr Val Ser Ser
        115

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct tcagtgactt caac                                            24

<210> SEQ ID NO 212
<211> LENGTH: 8
<212> TYPE: PRT

```
<213> ORGANISM: Artificial Sequence
<220> FEATURE:
<223> OTHER INFORMATION: Synthetic

<400> SEQUENCE: 212

Gly Phe Thr Phe Ser Asp Phe Asn
1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attagtggta gtggtaatgt catt                                              24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Gly Ser Gly Asn Val Ile
1               5

<210> SEQ ID NO 215
<211> LENGTH: 36
<212> TYPE: DNA
<213> ORGANISM: Artificial Sequence
<220> FEATURE:
<223> OTHER INFORMATION: Synthetic

<400> SEQUENCE: 215
gcgagagata tcggtgactc cgatgcgttt gatatc                                 36

<210> SEQ ID NO 216
<211> LENGTH: 12
<212> TYPE: PRT
<213> ORGANISM: Artificial Sequence
<220> FEATURE:
<223> OTHER INFORMATION: Synthetic

<400> SEQUENCE: 216

Ala Arg Asp Ile Gly Asp Ser Asp Ala Phe Asp Ile
1               5                   10

<210> SEQ ID NO 217
<211> LENGTH: 324
<212> TYPE: DNA
<213> ORGANISM: Artificial Sequence
<220> FEATURE:
<223> OTHER INFORMATION: Synthetic

<400> SEQUENCE: 217
gacatccagt tgacccagtc tccatccttc ctgtctgcat ctgtaggaga cagagtcacc       60
atcacttgct gggccagtca ggacattagc agttatttag cctggtatca gcaaaaacca      120
gggaaagccc ctaagctcct gatctatggt gcatccactt tggaaagtgg ggtcccatca      180
aggttcagcg gcagtggatc tgggacagaa ttcactctca caatcagcag cctgcagcct      240
gaagatgttg caacttatta ctgtcaacag cttaatactt acccgctcac tttcggcgga      300
```
gggaccaagg tggagatcaa acga                                                   324

<210> SEQ ID NO 218
<211> LENGTH: 108
<212> TYPE: PRT
<213> ORGANISM: Artificial Sequence
<220> FEATURE:
<223> OTHER INFORMATION: Synthetic

<400> SEQUENCE: 218

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Thr Tyr Tyr Cys Gln Gln Leu Asn Thr Tyr Pro Leu
                85                  90                  95

Thr Phe Gly Gly Gly Thr Lys Val Glu Ile Lys Arg
            100                 105

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
caggacatta gcagttat                                                          18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Asp Ile Ser Ser Tyr
1               5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 ggtgcatcc                                                                    9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Gly Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacagctta atacttaccc gctcact                                      27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Leu Asn Thr Tyr Pro Leu Thr
1               5

<210> SEQ ID NO 225
<211> LENGTH: 357
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtacatc ctggcaggtc cctgagactc      60
tcctgtgcag cctctggatt tacctttgat gattatgcca tgcactgggt ccggcaatct     120
ccagggaagg gcctggagtg ggtctcaggt attagttgga atagtgttat caaacactct     180
acggactctg tgaggggccg attcaccatc tccagagaca acgccaagaa ctccctgtat     240
ctgcaaatga acagtctgaa acctgaggac acggcctttt attactgtgc aaaggatgag     300
gatgactgga actaccttga ctactggggc cagggaaccc tggtcaccgt ctcctca        357

<210> SEQ ID NO 226
<211> LENGTH: 119
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val His Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ser Pro Gly Lys Gly Leu Glu Trp Val
        35                  40                  45

Ser Gly Ile Ser Trp Asn Ser Val Ile Lys His Ser Thr Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Pro Glu Asp Thr Ala Phe Tyr Tyr Cys
                85                  90                  95

Ala Lys Asp Glu Asp Asp Trp Asn Tyr Leu Asp Tyr Trp Gly Gln Gly
            100                 105                 110
Thr Leu Val Thr Val Ser Ser
        115

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggatttacct ttgatgatta tgcc                                          24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Phe Asp Asp Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagttgga atagtgttat caaa                                          24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Trp Asn Ser Val Ile Lys
1               5

<210> SEQ ID NO 231
<211> LENGTH: 36
<212> TYPE: DNA
<213> ORGANISM: Artificial Sequence
<220> FEATURE:
<223> OTHER INFORMATION: Synthetic

<400> SEQUENCE: 231
gcaaaggatg aggatgactg gaactacctt gactac                             36

<210> SEQ ID NO 232
<211> LENGTH: 12
<212> TYPE: PRT
<213> ORGANISM: Artificial Sequence
<220> FEATURE:
<223> OTHER INFORMATION: Synthetic

<400> SEQUENCE: 232

Ala Lys Asp Glu Asp Asp Trp Asn Tyr Leu Asp Tyr

<210> SEQ ID NO 233
<211> LENGTH: 324
<212> TYPE: DNA
<213> ORGANISM: Artificial Sequence
<220> FEATURE:
<223> OTHER INFORMATION: Synthetic

<400> SEQUENCE: 233

```
gacatccaga tgacccagtc tccatcttcc gtgtctgcat ctgtaggaga cagagtcacc      60
atcacttgtc gggcgagtca ggatattaac agctggttag cctggtatca gcagaaacca    120
gggaaagccc ctaaactcct gatctatact tcatccaatt tgcaaagtgg ggtcccatca    180
agattcagcg gcagtgggtc tgggacagat tcactctcac catcagcag cctgcagcct    240
gaagattttg caacttacta ttgtcaacag tctgacagtt tcccattcac tttcggccct    300
gggaccaaag tggatatcaa acga                                            324
```

<210> SEQ ID NO 234
<211> LENGTH: 108
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Asp Ile Asn Ser Trp
            20                  25                  30
Leu Ala Trp Tyr Gln Gln Lys Pro Gly Lys Ala Pro Lys Leu Leu Ile
        35                  40                  45
Tyr Thr Ser Ser Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asp Ser Phe Pro Phe
                85                  90                  95
Thr Phe Gly Pro Gly Thr Lys Val Asp Ile Lys Arg
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

```
caggatatta acagctgg                                                    18
```

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Asp Ile Asn Ser Trp
1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 acttcatcc                                                                 9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Thr Ser Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
caacagtctg acagtttccc attcact                                            27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Gln Gln Ser Asp Ser Phe Pro Phe Thr
1               5

<210> SEQ ID NO 241
<211> LENGTH: 366
<212> TYPE: DNA
<213> ORGANISM: Artificial Sequence
<220> FEATURE:
<223> OTHER INFORMATION: Synthetic

<400> SEQUENCE: 241
caggtgcagc tggtggagtc tgggggaggc gtggtccagc ctgggaggtc cctgagactc        60
tcctgtgcag cgtctggatt cacctttagt aactatggca tgcactgggt ccgccaggct       120
ccaggcaagg ggctggagtg gtggcacgt atatggtatg atggaagtaa taagtactat        180
gcagactccg tgaagggccg attcaccatc tccagagaca gttccaagaa cacgctgtat       240
ctgcaaatga acagcctgag agccgaggac acggctgtgt attactgtgc gagagagggg       300
gagcagaacc tggactatta ccctttagac gtctggggcc aagggaccac ggtcaccgtc       360
tcctca                                                                  366

<210> SEQ ID NO 242
<211> LENGTH: 122
<212> TYPE: PRT

<213> ORGANISM: Artificial Sequence
<220> FEATURE:
<223> OTHER INFORMATION: Synthetic

<400> SEQUENCE: 242

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Arg Ile Trp Tyr Asp Gly Ser Asn Lys Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu Gln Asn Leu Asp Tyr Tyr Pro Leu Asp Val Trp
            100                 105                 110

Gly Gln Gly Thr Thr Val Thr Val Ser Ser
        115                 120
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct ttagtaacta tggc                                          24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Phe Ser Asn Tyr Gly
1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatggtatg atggaagtaa taag                                          24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

```
Ile Trp Tyr Asp Gly Ser Asn Lys
1               5
```

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
gcgagagagg gggagcagaa cctggactat taccctttag acgtc        45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Arg Glu Gly Glu Gln Asn Leu Asp Tyr Tyr Pro Leu Asp Val
1               5                   10                  15

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gacatcgtga tgacccagtc tccatcctcc ctgtctgcat ctgttggaga cagagtcacc        60
atcacttgcc gggcaagtca ggacattaga aatgatttag ctggtatca acagaaacca        120 gggaaagccc ctaagctcct gatctatgct gcatccagtt tacaaactgg ggtcccatca        180
aggttcagcg gcagtgtatc tggcacagat ttcactctca ccatcagcag cctgcagcct        240
gaagattttg caacttatta ctgtctacaa gattacactt accctctcac tttcggcgga        300
gggaccaagg tggagatcaa a                                                 321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Val Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Thr Tyr Pro Leu
                85                  90                  95

Thr Phe Gly Gly Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
caggacatta gaaatgat                                                 18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Asp Ile Arg Asn Asp
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gctgcatcc                                                            9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Ala Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
ctacaagatt acacttaccc tctcact                                       27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Leu Gln Asp Tyr Thr Tyr Pro Leu Thr
1               5

<210> SEQ ID NO 257
<211> LENGTH: 354
<212> TYPE: DNA

<213> ORGANISM: Artificial Sequence
<220> FEATURE:
<223> OTHER INFORMATION: Synthetic

<400> SEQUENCE: 257

```
caggtgcagc tggtgcagtc tggagctgag gtgaagaagc ctggggcctc agtgaaggtc      60
tcctgcaagg cttctggtta caccttacc agatatggta tcagctgggt gcgacaggcc     120
cctggactag ggcttgagtg gatgggctgg atcagcgctt acgatggata cacaaacttt    180
gcacagaagt tccagggcag attcaccatg accacagaca catccacgaa cacagcctac    240
atggaactga ggcctgag atctgacgac acggccgtgt attactgtgc gagagaggag     300
gaggatgctg cttttgatat ctggggccaa gggacaatgg tcaccgtctc ttca          354
```

<210> SEQ ID NO 258
<211> LENGTH: 118
<212> TYPE: PRT
<213> ORGANISM: Artificial Sequence
<220> FEATURE:
<223> OTHER INFORMATION: Synthetic

<400> SEQUENCE: 258

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Leu Gly Leu Glu Trp Met
        35                  40                  45

Gly Trp Ile Ser Ala Tyr Asp Gly Tyr Thr Asn Phe Ala Gln Lys Phe
    50                  55                  60

Gln Gly Arg Phe Thr Met Thr Thr Asp Thr Ser Thr Asn Thr Ala Tyr
65                  70                  75                  80

Met Glu Leu Arg Gly Leu Arg Ser Asp Asp Thr Ala Val Tyr Tyr Cys
                85                  90                  95

Ala Arg Glu Glu Glu Asp Ala Ala Phe Asp Ile Trp Gly Gln Gly Thr
            100                 105                 110

Met Val Thr Val Ser Ser
        115
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggttacacct ttaccagata tggt                                             24
```

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

```
Gly Tyr Thr Phe Thr Arg Tyr Gly
1               5
```

<210> SEQ ID NO 261

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
atcagcgctt acgatggata caca                                    24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Ala Tyr Asp Gly Tyr Thr
1               5

<210> SEQ ID NO 263
<211> LENGTH: 33
<212> TYPE: DNA
<213> ORGANISM: Artificial Sequence
<220> FEATURE:
<223> OTHER INFORMATION: Synthetic

<400> SEQUENCE: 263
gcgagagagg aggaggatgc tgcttttgat atc                           33

<210> SEQ ID NO 264
<211> LENGTH: 11
<212> TYPE: PRT
<213> ORGANISM: Artificial Sequence
<220> FEATURE:
<223> OTHER INFORMATION: Synthetic

<400> SEQUENCE: 264

Ala Arg Glu Glu Glu Asp Ala Ala Phe Asp Ile
1               5                   10

<210> SEQ ID NO 265
<211> LENGTH: 342
<212> TYPE: DNA
<213> ORGANISM: Artificial Sequence
<220> FEATURE:
<223> OTHER INFORMATION: Synthetic

<400> SEQUENCE: 265
gacatcgtga tgacccagtc tccagactcc ctagatgtgc ctctgggcga gagggccacc    60
atcaactgca gtccagcca gagtatttta ttcggctcca acaataaaaa ctacttagct   120
tggtaccagc agaaatcagg acagcctcca aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctcacactt ttggccaggg gaccaagctg gagatcaaac ga                     342

<210> SEQ ID NO 266
<211> LENGTH: 114
<212> TYPE: PRT
<213> ORGANISM: Artificial Sequence
<220> FEATURE:
<223> OTHER INFORMATION: Synthetic

<400> SEQUENCE: 266

```
Asp Ile Val Met Thr Gln Ser Pro Asp Ser Leu Asp Val Pro Leu Gly
1               5                   10                  15

Glu Arg Ala Thr Ile Asn Cys Lys Ser Ser Gln Ser Ile Leu Phe Gly
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro His Thr Phe Gly Gln Gly Thr Lys Val Glu Ile
            100                 105                 110

Lys Arg
```

<210> SEQ ID NO 267
<211> LENGTH: 36
<212> TYPE: DNA
<213> ORGANISM: Artificial Sequence
<220> FEATURE:
<223> OTHER INFORMATION: Synthetic

<400> SEQUENCE: 267
cagagtattt tattcggctc aacaataaa aactac        36

<210> SEQ ID NO 268
<211> LENGTH: 12
<212> TYPE: PRT
<213> ORGANISM: Artificial Sequence
<220> FEATURE:
<223> OTHER INFORMATION: Synthetic

<400> SEQUENCE: 268

```
Gln Ser Ile Leu Phe Gly Ser Asn Asn Lys Asn Tyr
1               5                   10
```

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 tgggcatct        9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

```
Trp Ala Ser
1
```

<210> SEQ ID NO 271
<211> LENGTH: 27
<212> TYPE: DNA
<213> ORGANISM: Artificial Sequence

```
<220> FEATURE:
<223> OTHER INFORMATION: Synthetic

<400> SEQUENCE: 271
cagcaatatt atagtactcc tcacact                                          27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Tyr Tyr Ser Thr Pro His Thr
1               5

<210> SEQ ID NO 273
<211> LENGTH: 372
<212> TYPE: DNA
<213> ORGANISM: Artificial Sequence
<220> FEATURE:
<223> OTHER INFORMATION: Synthetic

<400> SEQUENCE: 273
caggtgcagc tgcaggagtc gggcccagga ctgattaacc cttcacagac cctgtccgtc       60
acctgcactg tctctggtgg ctccatcagc agtggtggtt attattggac ctggatacgc      120
cagcacccag gaaagggcct ggagtggatt gggtacatct cttacagtgg gaacaccaac      180
tataatccgt ccctcaagag tcgagttacc atatcagtag acacggctaa gaaccagttc      240
tccctgaagc tgagctctgt gactgccgcg gacacggccg tctacttctg tgcgagagac      300
agtgacgtgg acacagctat ggttgatggt attgatatct ggggccaagg gacaatggtc      360
accgtctctt ca                                                         372

<210> SEQ ID NO 274
<211> LENGTH: 124
<212> TYPE: PRT
<213> ORGANISM: Artificial Sequence
<220> FEATURE:
<223> OTHER INFORMATION: Synthetic

<400> SEQUENCE: 274

Gln Val Gln Leu Gln Glu Ser Gly Pro Gly Leu Ile Asn Pro Ser Gln
1               5                   10                  15

Thr Leu Ser Val Thr Cys Thr Val Ser Gly Gly Ser Ile Ser Ser Gly
                20                  25                  30

Gly Tyr Tyr Trp Thr Trp Ile Arg Gln His Pro Gly Lys Gly Leu Glu
            35                  40                  45

Trp Ile Gly Tyr Ile Ser Tyr Ser Gly Asn Thr Asn Tyr Asn Pro Ser
        50                  55                  60

Leu Lys Ser Arg Val Thr Ile Ser Val Asp Thr Ala Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Asp Ser Asp Val Asp Thr Ala Met Val Asp Gly Ile Asp
            100                 105                 110

Ile Trp Gly Gln Gly Thr Met Val Thr Val Ser Ser
        115                 120
```

<210> SEQ ID NO 275
<211> LENGTH: 30
<212> TYPE: DNA
<213> ORGANISM: Artificial Sequence
<220> FEATURE:
<223> OTHER INFORMATION: Synthetic

<400> SEQUENCE: 275
ggtggctcca tcagcagtgg tggttattat         30

<210> SEQ ID NO 276
<211> LENGTH: 10
<212> TYPE: PRT
<213> ORGANISM: Artificial Sequence
<220> FEATURE:
<223> OTHER INFORMATION: Synthetic

<400> SEQUENCE: 276

Gly Gly Ser Ile Ser Ser Gly Gly Tyr Tyr
 1               5                  10

<210> SEQ ID NO 277
<211> LENGTH: 21
<212> TYPE: DNA
<213> ORGANISM: Artificial Sequence
<220> FEATURE:
<223> OTHER INFORMATION: Synthetic

<400> SEQUENCE: 277
atctcttaca gtgggaacac c         21

<210> SEQ ID NO 278
<211> LENGTH: 7
<212> TYPE: PRT
<213> ORGANISM: Artificial Sequence
<220> FEATURE:
<223> OTHER INFORMATION: Synthetic

<400> SEQUENCE: 278

Ile Ser Tyr Ser Gly Asn Thr
 1               5

<210> SEQ ID NO 279
<211> LENGTH: 48
<212> TYPE: DNA
<213> ORGANISM: Artificial Sequence
<220> FEATURE:
<223> OTHER INFORMATION: Synthetic

<400> SEQUENCE: 279
gcgagagaca gtgacgtgga cacagctatg gttgatggta ttgatatc         48

<210> SEQ ID NO 280
<211> LENGTH: 16
<212> TYPE: PRT
<213> ORGANISM: Artificial Sequence
<220> FEATURE:
<223> OTHER INFORMATION: Synthetic

<400> SEQUENCE: 280

Ala Arg Asp Ser Asp Val Asp Thr Ala Met Val Asp Gly Ile Asp Ile
 1               5                  10                  15

<210> SEQ ID NO 281
<211> LENGTH: 324
<212> TYPE: DNA
<213> ORGANISM: Artificial Sequence
<220> FEATURE:
<223> OTHER INFORMATION: Synthetic

<400> SEQUENCE: 281

```
gacatccaga tgacccagtc tccatcttcc gtgtctgcat ctgtaggaga cagagtcacc      60
atcacttgtc gggcgagtca ggatattagc agctggttag cctggtatca gcagaaaccg    120
gggagagccc ctaaactcct gatctatact gcatccagtt tacaaagtgg ggtcccatca    180
aggttcagcg gcagtggatc tgggacagat ttcactctca ccatcagcag cctgcagcct    240
gaagattttg caacttactt ttgtcaacag gctaacagtt tcccattcac tttcggccct    300
gggaccaaag tggatatcaa acga                                           324
```

<210> SEQ ID NO 282
<211> LENGTH: 108
<212> TYPE: PRT
<213> ORGANISM: Artificial Sequence
<220> FEATURE:
<223> OTHER INFORMATION: Synthetic

<400> SEQUENCE: 282

```
Asp Ile Gln Met Thr Gln Ser Pro Ser Ser Val Ser Ala Ser Val Gly
1               5                   10                  15
Asp Arg Val Thr Ile Thr Cys Arg Ala Ser Gln Asp Ile Ser Ser Trp
            20                  25                  30
Leu Ala Trp Tyr Gln Gln Lys Pro Gly Arg Ala Pro Lys Leu Leu Ile
        35                  40                  45
Tyr Thr Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Phe Cys Gln Gln Ala Asn Ser Phe Pro Phe
                85                  90                  95
Thr Phe Gly Pro Gly Thr Lys Val Asp Ile Lys Arg
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283

```
caggatatta gcagctgg                                                   18
```

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
Gln Asp Ile Ser Ser Trp
1               5
```

<210> SEQ ID NO 285
<211> LENGTH: 9
<212> TYPE: DNA
<213> ORGANISM: Artificial Sequence
<220> FEATURE:

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 285 actgcatcc                                                                 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Thr Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacaggcta acagtttccc attcact                                             27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Ala Asn Ser Phe Pro Phe Thr
1               5

<210> SEQ ID NO 289
<211> LENGTH: 369
<212> TYPE: DNA
<213> ORGANISM: Artificial Sequence
<220> FEATURE:
<223> OTHER INFORMATION: Synthetic

<400> SEQUENCE: 289
gaggtgcagc tgttggagtc tgggggaggc ttggtacagc cggggggggtc cctgagactc        60 tcctgtgtag cctctggatt caccttcagc agttttgcca tgagttgggt ccgccaggct       120
ccagggaagg ggctggagtg ggtctcagtc attagtggta gtggtggcag cacaaatcac       180
gcagactccg tgaggggccg gttcaccatc tccagagaca attccctgaa cacggtgtat       240
ctacaaatgc acagtctgag agccgaggat acggccttat attactgtgt gaaagcggag       300
accagctctt cctacttcta ctacggtatg gacgtctggg gccaagggac cacggtcacc       360
gtctcctca                                                               369

<210> SEQ ID NO 290
<211> LENGTH: 123
<212> TYPE: PRT
<213> ORGANISM: Artificial Sequence
<220> FEATURE:
<223> OTHER INFORMATION: Synthetic

<400> SEQUENCE: 290

Glu Val Gln Leu Leu Glu Ser Gly Gly Gly Leu Val Gln Pro Gly Gly

```
                1               5                  10                 15
Ser Leu Arg Leu Ser Cys Val Ala Ser Gly Phe Thr Phe Ser Ser Phe
                20                 25                 30

Ala Met Ser Trp Val Arg Gln Ala Pro Gly Lys Gly Leu Glu Trp Val
                35                 40                 45

Ser Val Ile Ser Gly Ser Gly Gly Ser Thr Asn His Ala Asp Ser Val
                50                 55                 60

Arg Gly Arg Phe Thr Ile Ser Arg Asp Asn Ser Leu Asn Thr Val Tyr
 65                 70                 75                 80

Leu Gln Met His Ser Leu Arg Ala Glu Asp Thr Ala Leu Tyr Tyr Cys
                85                 90                 95

Val Lys Ala Glu Thr Ser Ser Ser Tyr Phe Tyr Tyr Gly Met Asp Val
                100                105                110

Trp Gly Gln Gly Thr Thr Val Thr Val Ser Ser
                115                120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct tcagcagttt tgcc                                              24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ser Phe Ala
 1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagtggta gtggtggcag caca                                              24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Gly Ser Gly Gly Ser Thr
 1               5

<210> SEQ ID NO 295
<211> LENGTH: 48
<212> TYPE: DNA
<213> ORGANISM: Artificial Sequence
<220> FEATURE:
```

<223> OTHER INFORMATION: Synthetic

<400> SEQUENCE: 295
gtgaaagcgg agaccagctc ttcctacttc tactacggta tggacgtc          48

<210> SEQ ID NO 296
<211> LENGTH: 16
<212> TYPE: PRT
<213> ORGANISM: Artificial Sequence
<220> FEATURE:
<223> OTHER INFORMATION: Synthetic

<400> SEQUENCE: 296

Val Lys Ala Glu Thr Ser Ser Tyr Phe Tyr Tyr Gly Met Asp Val
1               5                   10                  15

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccagt tgacccagtc tccatccttc ctgtctgcat ctgtaggaga cagagtcacc    60
atcacttgct gggccagtca ggacattagc agttatttag cctggtatca gcaaaaacca   120
gggaaagtcc ctaacctcct gatctatggt gcatcctctt tgcaacctgg ggtcccatca   180
cggttcagcg gcagtggatc tgggacagaa ttcactctca caatcagcag cctgcagcct   240
gaagattttg caacttatta ctgtcaacag ttaaataatt accccacttt cggcggaggg   300
accaagctgg agatcaaacg a                                              321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Ile Ser Ser Tyr
                20                  25                  30

Leu Ala Trp Tyr Gln Gln Lys Pro Gly Lys Val Pro Asn Leu Leu Ile
            35                  40                  45

Tyr Gly Ala Ser Ser Leu Gln Pro Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Asn Tyr Pro Thr
                85                  90                  95

Phe Gly Gly Gly Thr Lys Leu Glu Ile Lys Arg
            100                 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

```
<400> SEQUENCE: 299
caggacatta gcagttat                                                    18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Asp Ile Ser Ser Tyr
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 ggtgcatcc                                                               9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Gly Ala Ser
1

<210> SEQ ID NO 303
<211> LENGTH: 24
<212> TYPE: DNA
<213> ORGANISM: Artificial Sequence
<220> FEATURE:
<223> OTHER INFORMATION: Synthetic

<400> SEQUENCE: 303
caacagttaa ataattaccc cact                                             24

<210> SEQ ID NO 304
<211> LENGTH: 8
<212> TYPE: PRT
<213> ORGANISM: Artificial Sequence
<220> FEATURE:
<223> OTHER INFORMATION: Synthetic

<400> SEQUENCE: 304

Gln Gln Leu Asn Asn Tyr Pro Thr
1               5

<210> SEQ ID NO 305
<211> LENGTH: 363
<212> TYPE: DNA
<213> ORGANISM: Artificial Sequence
<220> FEATURE:
<223> OTHER INFORMATION: Synthetic

<400> SEQUENCE: 305
gaagtgcagc tggtggagtc tgggggaggt gtggtacggc ctggggggtc cctgagactc       60
```

```
tcctgtgcag cctctggatt cacctttgat gattatgcca tgcactgggt ccggcaagct      120
ccagggaagg gcctggagtg ggtcgcaggc attagttgga atagtggtag tatagactat      180
gcggactctg tgaagggccg attcaccatt tccagagaca acgccaaaaa ctccctgtat      240
ctgcaaatga acagtctgcg agctggggac acggccttgt attactgtgc aaaagatatt      300
ctggatctag actactacgg tttggacgtc tggggccaag gaccacggt caccgtctcc      360 tca                                                                    363
```

<210> SEQ ID NO 306
<211> LENGTH: 121
<212> TYPE: PRT
<213> ORGANISM: Artificial Sequence
<220> FEATURE:
<223> OTHER INFORMATION: Synthetic

<400> SEQUENCE: 306

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asn Ser Gly Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Leu Tyr Tyr Cys
                85                  90                  95

Ala Lys Asp Ile Leu Asp Leu Asp Tyr Tyr Gly Leu Asp Val Trp Gly
            100                 105                 110

Gln Gly Thr Thr Val Thr Val Ser Ser
        115                 120
```

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307

```
ggattcaccT ttgatgatta tgcc                                              24
```

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

```
Gly Phe Thr Phe Asp Asp Tyr Ala
1               5
```

<210> SEQ ID NO 309
<211> LENGTH: 24
<212> TYPE: DNA
<213> ORGANISM: Artificial Sequence
<220> FEATURE:
<223> OTHER INFORMATION: Synthetic
<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 309
attagttgga atagtggtag tata                                              24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Trp Asn Ser Gly Ser Ile
 1               5

<210> SEQ ID NO 311
<211> LENGTH: 42
<212> TYPE: DNA
<213> ORGANISM: Artificial Sequence
<220> FEATURE:
<223> OTHER INFORMATION: Synthetic

<400> SEQUENCE: 311
gcaaaagata ttctggatct agactactac ggtttggacg tc                          42

<210> SEQ ID NO 312
<211> LENGTH: 14
<212> TYPE: PRT
<213> ORGANISM: Artificial Sequence
<220> FEATURE:
<223> OTHER INFORMATION: Synthetic

<400> SEQUENCE: 312

Ala Lys Asp Ile Leu Asp Leu Asp Tyr Tyr Gly Leu Asp Val
 1               5                  10

<210> SEQ ID NO 313
<211> LENGTH: 321
<212> TYPE: DNA
<213> ORGANISM: Artificial Sequence
<220> FEATURE:
<223> OTHER INFORMATION: Synthetic

<400> SEQUENCE: 313
gacatccaga tgacccagtc tccatcctcc ctgtctgcat ctgtaggaga cagagtcacc        60
atcacttgcc gggcgagtca ggacattagc agttatttag cctggtatca gcagaaacca       120
gggaaagttc ctaacctcct gatctatgat gcatcctctt tgcaatcagg ggtcccatct       180
cggttcagtg gcagtggatc tgggacagat ttcactctca ccctcagcag cctgcagcct       240
gaagattttg ctagttatta ctgtcaaaat tataacagtg ccccgtacac ttttggccag       300
gggaccaagc tggagatcaa a                                                 321

<210> SEQ ID NO 314
<211> LENGTH: 107
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Tyr

```
                    20                  25                  30
Leu Ala Trp Tyr Gln Gln Lys Pro Gly Lys Val Pro Asn Leu Leu Ile
             35                  40                  45

Tyr Asp Ala Ser Ser Leu Gln Ser Gly Val Pro Ser Arg Phe Ser Gly
         50                  55                  60

Ser Gly Ser Gly Thr Asp Phe Thr Leu Thr Leu Ser Ser Leu Gln Pro
 65                  70                  75                  80

Glu Asp Phe Ala Ser Tyr Tyr Cys Gln Asn Tyr Asn Ser Ala Pro Tyr
                 85                  90                  95

Thr Phe Gly Gln Gly Thr Lys Leu Glu Ile Lys
            100                 105
```

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
caggacatta gcagttat                                                 18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Asp Ile Ser Ser Tyr
1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 gatgcatcc                                                            9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Asp Ala Ser
1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
caaaattata acagtgcccc gtacact                                       27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Gln Asn Tyr Asn Ser Ala Pro Tyr Thr
1               5

<210> SEQ ID NO 321
<211> LENGTH: 366
<212> TYPE: DNA
<213> ORGANISM: Artificial Sequence
<220> FEATURE:
<223> OTHER INFORMATION: Synthetic

<400> SEQUENCE: 321
gaagtgcaac tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaagt attagttgga atagtggtag cataggctat     180
gcggactctg tgaagggccg attcaccatt tccagagaca acgccaagaa ttccctgtat     240
cttcaaatga acagtctgaa acctgaggac acggccttgt attactgtac aaaagatacc     300
gactacggtg actaccttga tgcttttgat atctggggcc aagggacaat ggtcgccgtc     360
gcttca                                                                366

<210> SEQ ID NO 322
<211> LENGTH: 122
<212> TYPE: PRT
<213> ORGANISM: Artificial Sequence
<220> FEATURE:
<223> OTHER INFORMATION: Synthetic

<400> SEQUENCE: 322

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ser Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Pro Glu Asp Thr Ala Leu Tyr Tyr Cys
                85                  90                  95

Thr Lys Asp Thr Asp Tyr Gly Asp Tyr Leu Asp Ala Phe Asp Ile Trp
            100                 105                 110

Gly Gln Gly Thr Met Val Ala Val Ala Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct tgatgatta tgcc                                               24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Phe Thr Phe Asp Asp Tyr Ala
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
attagttgga atagtggtag cata                                              24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Trp Asn Ser Gly Ser Ile
1               5

<210> SEQ ID NO 327
<211> LENGTH: 45
<212> TYPE: DNA
<213> ORGANISM: Artificial Sequence
<220> FEATURE:
<223> OTHER INFORMATION: Synthetic

<400> SEQUENCE: 327
acaaaagata ccgactacgg tgactacctt gatgcttttg atatc                       45

<210> SEQ ID NO 328
<211> LENGTH: 15
<212> TYPE: PRT
<213> ORGANISM: Artificial Sequence
<220> FEATURE:
<223> OTHER INFORMATION: Synthetic

<400> SEQUENCE: 328

Thr Lys Asp Thr Asp Tyr Gly Asp Tyr Leu Asp Ala Phe Asp Ile
1               5                   10                  15

<210> SEQ ID NO 329
<211> LENGTH: 339
<212> TYPE: DNA
<213> ORGANISM: Artificial Sequence
<220> FEATURE:
<223> OTHER INFORMATION: Synthetic

<400> SEQUENCE: 329
gatattgtga tgacccagtc tccagactcc ctggctgtgt ctctgggcga gagggccacc       60

-continued

| | |
|---|---|
| atcaactgca agtccagcca gagtgtttta tacaactccg acaataagaa gtacttagct | 120 |
| tggtaccagc agaaacctgg acagcctcct aagctgctca tttactgggc atctacccgg | 180 |
| gaatccgggg tccctgaccg attcagtggc agcgggtctg ggacagattt cactctcacc | 240 |
| atcagcagcc tgcaggctga ggatgtggca gtttattact gtcaccaata ttatactact | 300 |
| cctccgacgt tcggccaagg gaccaaggtg gaaatcaaa | 339 |

<210> SEQ ID NO 330
<211> LENGTH: 113
<212> TYPE: PRT
<213> ORGANISM: Artificial Sequence
<220> FEATURE:
<223> OTHER INFORMATION: Synthetic

<400> SEQUENCE: 330

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Asn
            20                  25                  30
Ser Asp Asn Lys Lys Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys His Gln
                85                  90                  95
Tyr Tyr Thr Thr Pro Pro Thr Phe Gly Gln Gly Thr Lys Val Glu Ile
            100                 105                 110
Lys

<210> SEQ ID NO 331
<211> LENGTH: 36
<212> TYPE: DNA
<213> ORGANISM: Artificial Sequence
<220> FEATURE:
<223> OTHER INFORMATION: Synthetic

<400> SEQUENCE: 331
cagagtgttt tatacaactc cgacaataag aagtac                              36

<210> SEQ ID NO 332
<211> LENGTH: 12
<212> TYPE: PRT
<213> ORGANISM: Artificial Sequence
<220> FEATURE:
<223> OTHER INFORMATION: Synthetic

<400> SEQUENCE: 332

Gln Ser Val Leu Tyr Asn Ser Asp Asn Lys Lys Tyr
1               5                   10

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333 tgggcatct                                                            9

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

Trp Ala Ser
1

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335
caccaatatt atactactcc tccgacg                                          27

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

His Gln Tyr Tyr Thr Thr Pro Pro Thr
1               5

<210> SEQ ID NO 337
<211> LENGTH: 357
<212> TYPE: DNA
<213> ORGANISM: Artificial Sequence
<220> FEATURE:
<223> OTHER INFORMATION: Synthetic

<400> SEQUENCE: 337
gaggtgcagc tggtggagtc tgggggaggt gtggtacggc ctggggggtc cctgagactc        60
tcctgtgcag cctctggatt cacctttgat gattatggca tgagctgggt ccgccaagct      120
ccagggaagg ggctggagtg tgtctctggt attaattgga atggtggtag cacagattat      180
gcagactctg tgaagggccg attcaccatc tccagagaca acgccaagaa ctccctgtat      240
ctgcaaatga acagtctgag agccgaggac acggcctcgt attactgtgc gagagatggt      300
ggggattggg actacttcga tctctggggc cgtggcaccc tggtcactgt ctcctca        357

<210> SEQ ID NO 338
<211> LENGTH: 119
<212> TYPE: PRT
<213> ORGANISM: Artificial Sequence
<220> FEATURE:
<223> OTHER INFORMATION: Synthetic

<400> SEQUENCE: 338

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Cys Val
        35                  40                  45

```
Ser Gly Ile Asn Trp Asn Gly Gly Ser Thr Asp Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Gly Asp Trp Asp Tyr Phe Asp Leu Trp Gly Arg Gly
            100                 105                 110

Thr Leu Val Thr Val Ser Ser
        115
```

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggattcacct ttgatgatta tggc                                    24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

```
Gly Phe Thr Phe Asp Asp Tyr Gly
 1               5
```

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
attaattgga atggtggtag caca                                    24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

```
Ile Asn Trp Asn Gly Gly Ser Thr
 1               5
```

<210> SEQ ID NO 343
<211> LENGTH: 36
<212> TYPE: DNA
<213> ORGANISM: Artificial Sequence
<220> FEATURE:
<223> OTHER INFORMATION: Synthetic

<400> SEQUENCE: 343
gcgagagatg gtggggattg ggactacttc gatctc                       36

```
<210> SEQ ID NO 344
<211> LENGTH: 12
<212> TYPE: PRT
<213> ORGANISM: Artificial Sequence
<220> FEATURE:
<223> OTHER INFORMATION: Synthetic

<400> SEQUENCE: 344

Ala Arg Asp Gly Gly Asp Trp Asp Tyr Phe Asp Leu
1               5                   10

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345
gaaatagtga tgacgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catatatgga gcatccacca gggccactgg tatcccagcc    180
aggttcagtg gcagtgggtc tgggacagag ttcactctca ccatcagcag cctgcagtct    240
gaagattttg cagtttattt ctgtcaggag tataatgact ggccgctcac tttcggcgga    300
gggaccaagg tggagatcaa a                                              321

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Glu Tyr Asn Asp Trp Pro Leu
                85                  90                  95

Thr Phe Gly Gly Gly Thr Lys Val Glu Ile Lys
            100                 105

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
cagagtgtta gcagcaac                                                   18

<210> SEQ ID NO 348
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Ser Val Ser Ser Asn
1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 ggagcatcc                                                                  9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Gly Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caggagtata atgactggcc gctcact                                              27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Glu Tyr Asn Asp Trp Pro Leu Thr
1               5

<210> SEQ ID NO 353
<211> LENGTH: 357
<212> TYPE: DNA
<213> ORGANISM: Artificial Sequence
<220> FEATURE:
<223> OTHER INFORMATION: Synthetic

<400> SEQUENCE: 353
gaggtgcaac tggtggagtc tgggggaggt gtggtacggc ctggggggtc cctgagactc          60
tcctgtgcag cctctggatt cacctttgat gattatggca tgagctgggt ccgccaagct         120
ccagggaagg ggctggagtg tgtctctggt attagttgga atggtggtaa cacagattat         180
gcagactctg tgaagggccg attcaccatc tccagagaca acgccaagaa ctccctgtat         240
```

```
ctgcaaatga acagtctgag agccgaggac acggccttgt atcactgtgc gagagatggt    300
ggggattggg actacttcga tctctggggc cgtggcaccc tggtcactgt ctcctca      357
```

<210> SEQ ID NO 354
<211> LENGTH: 119
<212> TYPE: PRT
<213> ORGANISM: Artificial Sequence
<220> FEATURE:
<223> OTHER INFORMATION: Synthetic

<400> SEQUENCE: 354

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Cys Val
        35                  40                  45

Ser Gly Ile Ser Trp Asn Gly Gly Asn Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Asp Gly Gly Asp Trp Asp Tyr Phe Asp Leu Trp Gly Arg Gly
            100                 105                 110

Thr Leu Val Thr Val Ser Ser
        115
```

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355

```
ggattcacct ttgatgatta tggc                                          24
```

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

```
Gly Phe Thr Phe Asp Asp Tyr Gly
1               5
```

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357

```
attagttgga atggtggtaa caca                                          24
```

<210> SEQ ID NO 358
<211> LENGTH: 8
<212> TYPE: PRT

<213> ORGANISM: Artificial Sequence
<220> FEATURE:
<223> OTHER INFORMATION: Synthetic

<400> SEQUENCE: 358

Ile Ser Trp Asn Gly Gly Asn Thr
1               5

<210> SEQ ID NO 359
<211> LENGTH: 36
<212> TYPE: DNA
<213> ORGANISM: Artificial Sequence
<220> FEATURE:
<223> OTHER INFORMATION: Synthetic

<400> SEQUENCE: 359

```
gcgagagatg gtggggattg ggactacttc gatctc                               36
```

<210> SEQ ID NO 360
<211> LENGTH: 12
<212> TYPE: PRT
<213> ORGANISM: Artificial Sequence
<220> FEATURE:
<223> OTHER INFORMATION: Synthetic

<400> SEQUENCE: 360

Ala Arg Asp Gly Gly Asp Trp Asp Tyr Phe Asp Leu
1               5                   10

<210> SEQ ID NO 361
<211> LENGTH: 321
<212> TYPE: DNA
<213> ORGANISM: Artificial Sequence
<220> FEATURE:
<223> OTHER INFORMATION: Synthetic

<400> SEQUENCE: 361

```
gaaatactga tgacgcagtc tccagccacc ctgtctgtgt ctccagggga aagagccacc     60
ctctcctgca gggccagtca gagtgttagt agcaacttag cctggtacca gcagaaacct   120
ggccaggctc ccaggctcct catatatgga gcatccacca gggccactgg tatcccagcc   180
aggttcagtg gcagtgggtc tgggacagag ttcactctta ccatcagcag cctgcagtct   240
gaagattttg caatttatta ctgtcaggag tataatgact ggccgctcac tttcggcgga   300
gggaccaagg tggagatcaa a                                              321
```

<210> SEQ ID NO 362
<211> LENGTH: 107
<212> TYPE: PRT
<213> ORGANISM: Artificial Sequence
<220> FEATURE:
<223> OTHER INFORMATION: Synthetic

<400> SEQUENCE: 362

Glu Ile Leu Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser

```
            65                  70                  75                  80
Glu Asp Phe Ala Ile Tyr Tyr Cys Gln Glu Tyr Asn Asp Trp Pro Leu
                    85                  90                  95

Thr Phe Gly Gly Gly Thr Lys Val Glu Ile Lys
            100                 105
```

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
cagagtgtta gtagcaac                                              18

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

Gln Ser Val Ser Ser Asn
1               5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 ggagcatcc                                                         9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Gly Ala Ser
1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
caggagtata atgactggcc gctcact                                    27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Glu Tyr Asn Asp Trp Pro Leu Thr
1               5

<210> SEQ ID NO 369
<211> LENGTH: 363
<212> TYPE: DNA
<213> ORGANISM: Artificial Sequence
<220> FEATURE:
<223> OTHER INFORMATION: Synthetic

<400> SEQUENCE: 369
gaagtgcaac tggtggagtc tgggggaggc ttggtacagc ctggcaggtc cctgagactc    60
tcctgtgcag cctctggatt cacctttgat gattatgcca tgtactgggt ccggcaagct   120
ccagggaagg gcctggagtg ggtctcaggt attagttgga atagtggcag cataggctat   180
gcggactctg tgaagggccg attcaccatc tctagagaca cgccaagaa ctccctgtat    240 ctgcaaatgg acagcctgag agctgaggac acggccttgt attactgtgc aagagatatg   300
atggaagttg acctctacgg tatggacgtc tggggccaag ggaccacggt caccgtctcc   360
tca                                                                 363

<210> SEQ ID NO 370
<211> LENGTH: 121
<212> TYPE: PRT
<213> ORGANISM: Artificial Sequence
<220> FEATURE:
<223> OTHER INFORMATION: Synthetic

<400> SEQUENCE: 370

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Leu Tyr Tyr Cys
                85                  90                  95

Ala Arg Asp Met Met Glu Val Asp Leu Tyr Gly Met Asp Val Trp Gly
            100                 105                 110

Gln Gly Thr Thr Val Thr Val Ser Ser
        115                 120

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggattcacct ttgatgatta tgcc                                           24

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

Gly Phe Thr Phe Asp Asp Tyr Ala
1               5

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
attagttgga atagtggcag cata                                        24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Trp Asn Ser Gly Ser Ile
1               5

<210> SEQ ID NO 375
<211> LENGTH: 42
<212> TYPE: DNA
<213> ORGANISM: Artificial Sequence
<220> FEATURE:
<223> OTHER INFORMATION: Synthetic

<400> SEQUENCE: 375
gcaagagata tgatggaagt tgacctctac ggtatggacg tc                    42

<210> SEQ ID NO 376
<211> LENGTH: 14
<212> TYPE: PRT
<213> ORGANISM: Artificial Sequence
<220> FEATURE:
<223> OTHER INFORMATION: Synthetic

<400> SEQUENCE: 376

Ala Arg Asp Met Met Glu Val Asp Leu Tyr Gly Met Asp Val
1               5                   10

<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377
gacatccaga tgacccagtc tccatcttcc gtgtctgcat ctgtaggaga cagagtcacg    60
atcacttgtc gggcgagtca ggatattagc agttggttag cctggtatca gcagaaacca   120
gggacagccc ctaagttcct gatctatgaa acatccagtt tgcaaagtgg ggtcccttca   180
aggttcagcg gcagtggatc tgggacagat ttcattctca ccatcagtag cctgcagcct   240
gaagattttg caacttacta ttgtcaacaa actgacagtt cccgcacac ttttggccag   300 gggaccaagc tggagatcag a                                            321

<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Thr Ala Pro Lys Phe Leu Ile
        35                  40                  45

Tyr Glu Thr Ser Ser Leu Gln Ser Gly Val Pro Ser Arg Phe Ser Gly
50                  55                  60

Ser Gly Ser Gly Thr Asp Phe Ile Leu Thr Ile Ser Ser Leu Gln Pro
65                  70                  75                  80

Glu Asp Phe Ala Thr Tyr Tyr Cys Gln Gln Thr Asp Ser Phe Pro His
                85                  90                  95

Thr Phe Gly Gln Gly Thr Lys Leu Glu Ile Arg
            100                 105

<210> SEQ ID NO 379
<211> LENGTH: 18
<212> TYPE: DNA
<213> ORGANISM: Artificial Sequence
<220> FEATURE:
<223> OTHER INFORMATION: Synthetic

<400> SEQUENCE: 379
caggatatta gcagttgg                                               18

<210> SEQ ID NO 380
<211> LENGTH: 6
<212> TYPE: PRT
<213> ORGANISM: Artificial Sequence
<220> FEATURE:
<223> OTHER INFORMATION: Synthetic

<400> SEQUENCE: 380

Gln Asp Ile Ser Ser Trp
1               5

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381 gaaacatcc                                                          9

<210> SEQ ID NO 382
<211> LENGTH: 3
<212> TYPE: PRT
<213> ORGANISM: Artificial Sequence
<220> FEATURE:
<223> OTHER INFORMATION: Synthetic

<400> SEQUENCE: 382

Glu Thr Ser
1

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
caacaaactg acagtttccc gcacact                27

<210> SEQ ID NO 384
<211> LENGTH: 9
<212> TYPE: PRT
<213> ORGANISM: Artificial Sequence
<220> FEATURE:
<223> OTHER INFORMATION: Synthetic

<400> SEQUENCE: 384

Gln Gln Thr Asp Ser Phe Pro His Thr
1               5

<210> SEQ ID NO 385
<211> LENGTH: 357
<212> TYPE: DNA
<213> ORGANISM: Artificial Sequence
<220> FEATURE:
<223> OTHER INFORMATION: Synthetic

<400> SEQUENCE: 385
gaggtgcagc tggtggagtc tgggggaggt gtggtacggc ctgggggtc cctgagactc        60
tcctgtgtag cctctggatt cacctttgat gattatggca tgagctgggt ccgccaagct       120
ccagggaagg ggctggagtg tgtctctggt attaattgga atggtggtag cacagattat       180
gcagactctg tgaagggccg attcactatc tccagagaca cgccaagaa ctccctgtat        240
ctgcaaatga acagtctgag agccgaggac acggccttgt atcactgtgc gagagatggt       300
ggggattggg actacttcga tctctggggc cgtggcaccc tggtcactgt ctcctca         357

<210> SEQ ID NO 386
<211> LENGTH: 119
<212> TYPE: PRT
<213> ORGANISM: Artificial Sequence
<220> FEATURE:
<223> OTHER INFORMATION: Synthetic

<400> SEQUENCE: 386

Glu Val Gln Leu Val Glu Ser Gly Gly Gly Val Val Arg Pro Gly Gly
1               5                   10                  15

Ser Leu Arg Leu Ser Cys Val Ala Ser Gly Phe Thr Phe Asp Asp Tyr
            20                  25                  30

Gly Met Ser Trp Val Arg Gln Ala Pro Gly Lys Gly Leu Glu Cys Val
        35                  40                  45

Ser Gly Ile Asn Trp Asn Gly Gly Ser Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Asp Gly Gly Asp Trp Asp Tyr Phe Asp Leu Trp Gly Arg Gly

Thr Leu Val Thr Val Ser Ser
        115

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct ttgatgatta tggc          24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Asp Asp Tyr Gly
1               5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attaattgga atggtggtag caca          24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Asn Trp Asn Gly Gly Ser Thr
1               5

<210> SEQ ID NO 391
<211> LENGTH: 36
<212> TYPE: DNA
<213> ORGANISM: Artificial Sequence
<220> FEATURE:
<223> OTHER INFORMATION: Synthetic

<400> SEQUENCE: 391
gcgagagatg gtggggattg ggactacttc gatctc          36

<210> SEQ ID NO 392
<211> LENGTH: 12
<212> TYPE: PRT
<213> ORGANISM: Artificial Sequence
<220> FEATURE:
<223> OTHER INFORMATION: Synthetic

<400> SEQUENCE: 392

Ala Arg Asp Gly Gly Asp Trp Asp Tyr Phe Asp Leu
1               5                   10

<210> SEQ ID NO 393
<211> LENGTH: 321
<212> TYPE: DNA
<213> ORGANISM: Artificial Sequence
<220> FEATURE:
<223> OTHER INFORMATION: Synthetic

<400> SEQUENCE: 393

```
gaaatactga tgacgcagtc tccagccacc ctgtctgtgt ctccagggga aagagccacc        60
ctctcctgca gggccagtca gagtgttagc agcaacttag cctggtacca gcagaaacct       120
ggccaggctc ccaggctcct catatatgga gcatccacca gggccactgg tatcccagcc       180
aggttcagtg gcagtgggtc tgggacagag ttcactctca ccatcagcag cctgcagtct       240
gaagattttg caatttatta ctgtcaggag tataatgact ggccgctcac tttcggcgga       300
gggaccaagg tggagatcaa a                                                 321
```

<210> SEQ ID NO 394
<211> LENGTH: 107
<212> TYPE: PRT
<213> ORGANISM: Artificial Sequence
<220> FEATURE:
<223> OTHER INFORMATION: Synthetic

<400> SEQUENCE: 394

```
Glu Ile Leu Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Glu Tyr Asn Asp Trp Pro Leu
                85                  90                  95

Thr Phe Gly Gly Gly Thr Lys Val Glu Ile Lys
            100                 105
```

<210> SEQ ID NO 395
<211> LENGTH: 18
<212> TYPE: DNA
<213> ORGANISM: Artificial Sequence
<220> FEATURE:
<223> OTHER INFORMATION: Synthetic

<400> SEQUENCE: 395

```
cagagtgtta gcagcaac                                                      18
```

<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396

```
Gln Ser Val Ser Ser Asn
1               5
```

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 ggagcatcc                                                                 9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Gly Ala Ser
1

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399
caggagtata atgactggcc gctcact                                            27

<210> SEQ ID NO 400
<211> LENGTH: 9
<212> TYPE: PRT
<213> ORGANISM: Artificial Sequence
<220> FEATURE:
<223> OTHER INFORMATION: Synthetic

<400> SEQUENCE: 400

Gln Glu Tyr Asn Asp Trp Pro Leu Thr
1               5

<210> SEQ ID NO 401
<211> LENGTH: 357
<212> TYPE: DNA
<213> ORGANISM: Artificial Sequence
<220> FEATURE:
<223> OTHER INFORMATION: Synthetic

<400> SEQUENCE: 401
gaggtgcaac tggtggagtc tgggggaggc ctggtcaagc ctgggggtc cctgagactc          60 tcctgtgtag cctctggatt caccttcagt agctataaca tgaactgggt ccgccaggct        120
ccagggaagg ggctggagtg ggtctcattt ataagtggta gtagtaatta catacactac        180
gcagactcag tgaagggccg attcaccatt tccagagaca cgccaagaa tgcactgtat         240 ctgcagatga acagcctgag agccgaggac acggctgtat attactgtgc gagagacgac        300
ggtgactacg actggttcga cccctggggc cagggaaccc tggtcaccgt ctcctca          357

<210> SEQ ID NO 402
<211> LENGTH: 119
<212> TYPE: PRT
<213> ORGANISM: Artificial Sequence
<220> FEATURE:
<223> OTHER INFORMATION: Synthetic

<400> SEQUENCE: 402

Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Phe Ile Ser Gly Ser Ser Asn Tyr Ile His Tyr Ala Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Gly Asp Tyr Asp Trp Phe Asp Pro Trp Gly Gln Gly
            100                 105                 110

Thr Leu Val Thr Val Ser Ser
        115

<210> SEQ ID NO 403
<211> LENGTH: 24
<212> TYPE: DNA
<213> ORGANISM: Artificial Sequence
<220> FEATURE:
<223> OTHER INFORMATION: Synthetic

<400> SEQUENCE: 403
ggattcacct tcagtagcta taac                                      24

<210> SEQ ID NO 404
<211> LENGTH: 8
<212> TYPE: PRT
<213> ORGANISM: Artificial Sequence
<220> FEATURE:
<223> OTHER INFORMATION: Synthetic

<400> SEQUENCE: 404

Gly Phe Thr Phe Ser Ser Tyr Asn
1               5

<210> SEQ ID NO 405
<211> LENGTH: 24
<212> TYPE: DNA
<213> ORGANISM: Artificial Sequence
<220> FEATURE:
<223> OTHER INFORMATION: Synthetic

<400> SEQUENCE: 405
ataagtggta gtagtaatta cata                                      24

<210> SEQ ID NO 406
<211> LENGTH: 8
<212> TYPE: PRT
<213> ORGANISM: Artificial Sequence
<220> FEATURE:
<223> OTHER INFORMATION: Synthetic

<400> SEQUENCE: 406

Ile Ser Gly Ser Ser Asn Tyr Ile
1               5

<210> SEQ ID NO 407

<211> LENGTH: 36
<212> TYPE: DNA
<213> ORGANISM: Artificial Sequence
<220> FEATURE:
<223> OTHER INFORMATION: Synthetic

<400> SEQUENCE: 407
gcgagagacg acggtgacta cgactggttc gacccc                                      36

<210> SEQ ID NO 408
<211> LENGTH: 12
<212> TYPE: PRT
<213> ORGANISM: Artificial Sequence
<220> FEATURE:
<223> OTHER INFORMATION: Synthetic

<400> SEQUENCE: 408

Ala Arg Asp Asp Gly Asp Tyr Asp Trp Phe Asp Pro
1               5                  10

<210> SEQ ID NO 409
<211> LENGTH: 321
<212> TYPE: DNA
<213> ORGANISM: Artificial Sequence
<220> FEATURE:
<223> OTHER INFORMATION: Synthetic

<400> SEQUENCE: 409
gaaattgtgt tgacgcagtc tccaggcacc ctgtctttgt ctccagggga aagagccacc            60
ctctcctgca gggccagtca gagtgttagt agtagttact tagcctggta ccagcaaaaa           120
cctggccagg ctcccaggct cctcatctat ggtacatcca gcagggccac tggcatccca           180
gacaggttca gtggcagtgg gtctgggaca gacttcactc tcaccatcag cagactggag           240
cctgaagatt ttgcagtgta ttactgtcag cagtatgata actcatacac ttttggccag           300
gggaccaagc tggagatcaa a                                                     321

<210> SEQ ID NO 410
<211> LENGTH: 107
<212> TYPE: PRT
<213> ORGANISM: Artificial Sequence
<220> FEATURE:
<223> OTHER INFORMATION: Synthetic

<400> SEQUENCE: 410

Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Tyr
                85                  90                  95

Thr Phe Gly Gln Gly Thr Lys Leu Glu Ile Lys
            100                 105

<210> SEQ ID NO 411
<211> LENGTH: 21

```
<212> TYPE: DNA
<213> ORGANISM: Artificial Sequence
<220> FEATURE:
<223> OTHER INFORMATION: Synthetic

<400> SEQUENCE: 411
cagagtgtta gtagtagtta c                                          21

<210> SEQ ID NO 412
<211> LENGTH: 7
<212> TYPE: PRT
<213> ORGANISM: Artificial Sequence
<220> FEATURE:
<223> OTHER INFORMATION: Synthetic

<400> SEQUENCE: 412

Gln Ser Val Ser Ser Ser Tyr
1               5

<210> SEQ ID NO 413
<211> LENGTH: 9
<212> TYPE: DNA
<213> ORGANISM: Artificial Sequence
<220> FEATURE:
<223> OTHER INFORMATION: Synthetic

<400> SEQUENCE: 413 ggtacatcc                                                         9

<210> SEQ ID NO 414
<211> LENGTH: 3
<212> TYPE: PRT
<213> ORGANISM: Artificial Sequence
<220> FEATURE:
<223> OTHER INFORMATION: Synthetic

<400> SEQUENCE: 414

Gly Thr Ser
1

<210> SEQ ID NO 415
<211> LENGTH: 24
<212> TYPE: DNA
<213> ORGANISM: Artificial Sequence
<220> FEATURE:
<223> OTHER INFORMATION: Synthetic

<400> SEQUENCE: 415
cagcagtatg ataactcata cact                                       24

<210> SEQ ID NO 416
<211> LENGTH: 8
<212> TYPE: PRT
<213> ORGANISM: Artificial Sequence
<220> FEATURE:
<223> OTHER INFORMATION: Synthetic

<400> SEQUENCE: 416

Gln Gln Tyr Asp Asn Ser Tyr Thr
1               5

<210> SEQ ID NO 417
<211> LENGTH: 357
<212> TYPE: DNA
<213> ORGANISM: Artificial Sequence
<220> FEATURE:
<223> OTHER INFORMATION: Synthetic
```

<400> SEQUENCE: 417

```
gaggtgcagc tggtgcagtc tgggggaggc ctggtcaagc ctgggggtc cctgagactc      60
tcctgtgcag cctctggatt caccttcagt aactttaaca tgaactgggt ccgccaggct    120
ccagggaagg ggctggagtg ggtctcattc attagtagtc ttagtactta tacatactac    180
gcagactcag tgaagggccg attcaccatc tccagagaca acgccaagaa ctcactgtat    240
ctgcaaatga acagcctgag agccgaggac acggctgtgt attactgtgc gagagacgac    300
ggtgaccacg actggttcga ccctgggggc cagggaaccc tggtcaccgt ctcctca       357
```

<210> SEQ ID NO 418
<211> LENGTH: 119
<212> TYPE: PRT
<213> ORGANISM: Artificial Sequence
<220> FEATURE:
<223> OTHER INFORMATION: Synthetic

<400> SEQUENCE: 418

```
Glu Val Gln Leu Val Gln Ser Gly Gly Gly Leu Val Lys Pro Gly Gly
1               5                   10                  15
Ser Leu Arg Leu Ser Cys Ala Ala Ser Gly Phe Thr Phe Ser Asn Phe
            20                  25                  30
Asn Met Asn Trp Val Arg Gln Ala Pro Gly Lys Gly Leu Glu Trp Val
        35                  40                  45
Ser Phe Ile Ser Ser Leu Ser Thr Tyr Thr Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Asp Gly Asp His Asp Trp Phe Asp Pro Trp Gly Gln Gly
            100                 105                 110
Thr Leu Val Thr Val Ser Ser
        115
```

<210> SEQ ID NO 419
<211> LENGTH: 24
<212> TYPE: DNA
<213> ORGANISM: Artificial Sequence
<220> FEATURE:
<223> OTHER INFORMATION: Synthetic

<400> SEQUENCE: 419

```
ggattcacct tcagtaactt taac                                            24
```

<210> SEQ ID NO 420
<211> LENGTH: 8
<212> TYPE: PRT
<213> ORGANISM: Artificial Sequence
<220> FEATURE:
<223> OTHER INFORMATION: Synthetic

<400> SEQUENCE: 420

```
Gly Phe Thr Phe Ser Asn Phe Asn
1               5
```

<210> SEQ ID NO 421
<211> LENGTH: 24
<212> TYPE: DNA
<213> ORGANISM: Artificial Sequence

```
<220> FEATURE:
<223> OTHER INFORMATION: Synthetic

<400> SEQUENCE: 421
attagtagtc ttagtactta taca                                          24

<210> SEQ ID NO 422
<211> LENGTH: 8
<212> TYPE: PRT
<213> ORGANISM: Artificial Sequence
<220> FEATURE:
<223> OTHER INFORMATION: Synthetic

<400> SEQUENCE: 422

Ile Ser Ser Leu Ser Thr Tyr Thr
1               5

<210> SEQ ID NO 423
<211> LENGTH: 36
<212> TYPE: DNA
<213> ORGANISM: Artificial Sequence
<220> FEATURE:
<223> OTHER INFORMATION: Synthetic

<400> SEQUENCE: 423
gcgagagacg acggtgacca cgactggttc gacccc                             36

<210> SEQ ID NO 424
<211> LENGTH: 12
<212> TYPE: PRT
<213> ORGANISM: Artificial Sequence
<220> FEATURE:
<223> OTHER INFORMATION: Synthetic

<400> SEQUENCE: 424

Ala Arg Asp Asp Gly Asp His Asp Trp Phe Asp Pro
1               5                   10

<210> SEQ ID NO 425
<211> LENGTH: 321
<212> TYPE: DNA
<213> ORGANISM: Artificial Sequence
<220> FEATURE:
<223> OTHER INFORMATION: Synthetic

<400> SEQUENCE: 425
gaaattgtgt tgacgcagtc tccagacacc ctgtctttgt ctccagggga aagagccacc    60
ctctcctgca gggccagtca gagtgttagt agcaactact tagcctggta ccaacaaaaa   120
cctggccagg ctcccaggct cctcatctat agtgcatcca cagggccac tggcatccca    180 gacagattca gtggcagtgg gtctgggaca gacttcactc tcaccatcag ccgactggag   240
cctgaagatt ttgcagtgta ttactgtcaa cagtatgata gttcatacac ttttggccag   300
gggaccaagc tggagatcaa a                                             321

<210> SEQ ID NO 426
<211> LENGTH: 107
<212> TYPE: PRT
<213> ORGANISM: Artificial Sequence
<220> FEATURE:
<223> OTHER INFORMATION: Synthetic

<400> SEQUENCE: 426

Glu Ile Val Leu Thr Gln Ser Pro Asp Thr Leu Ser Leu Ser Pro Gly
1               5                   10                  15
```

Glu Arg Ala Thr Leu Ser Cys Arg Ala Ser Gln Ser Val Ser Ser Asn
            20                  25                  30

Tyr Leu Ala Trp Tyr Gln Lys Pro Gly Gln Ala Pro Arg Leu Leu
    35                  40                  45

Ile Tyr Ser Ala Ser Asn Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Asp Ser Ser Tyr
                85                  90                  95

Thr Phe Gly Gln Gly Thr Lys Leu Glu Ile Lys
            100                 105

<210> SEQ ID NO 427
<211> LENGTH: 21
<212> TYPE: DNA
<213> ORGANISM: Artificial Sequence
<220> FEATURE:
<223> OTHER INFORMATION: Synthetic

<400> SEQUENCE: 427
cagagtgtta gtagcaacta c                                           21

<210> SEQ ID NO 428
<211> LENGTH: 7
<212> TYPE: PRT
<213> ORGANISM: Artificial Sequence
<220> FEATURE:
<223> OTHER INFORMATION: Synthetic

<400> SEQUENCE: 428

Gln Ser Val Ser Ser Asn Tyr
 1               5

<210> SEQ ID NO 429
<211> LENGTH: 9
<212> TYPE: DNA
<213> ORGANISM: Artificial Sequence
<220> FEATURE:
<223> OTHER INFORMATION: Synthetic

<400> SEQUENCE: 429 agtgcatcc                                                          9

<210> SEQ ID NO 430
<211> LENGTH: 3
<212> TYPE: PRT
<213> ORGANISM: Artificial Sequence
<220> FEATURE:
<223> OTHER INFORMATION: Synthetic

<400> SEQUENCE: 430

Ser Ala Ser
 1

<210> SEQ ID NO 431
<211> LENGTH: 24
<212> TYPE: DNA
<213> ORGANISM: Artificial Sequence
<220> FEATURE:
<223> OTHER INFORMATION: Synthetic

<400> SEQUENCE: 431
caacagtatg atagttcata cact    24

<210> SEQ ID NO 432
<211> LENGTH: 8
<212> TYPE: PRT
<213> ORGANISM: Artificial Sequence
<220> FEATURE:
<223> OTHER INFORMATION: Synthetic

<400> SEQUENCE: 432

Gln Gln Tyr Asp Ser Ser Tyr Thr
1               5

<210> SEQ ID NO 433
<211> LENGTH: 363
<212> TYPE: DNA
<213> ORGANISM: Artificial Sequence
<220> FEATURE:
<223> OTHER INFORMATION: Synthetic

<400> SEQUENCE: 433
gaaatgcagc tggtagagtc tgggggaggc ttggtacagc ctgacaggtc cctgagactc    60
tcctgtgcag cctctggatt caactttgat aattatgcca tacactgggt ccggcaagct   120
ccagggaagg gcctcgagtg ggtctcaggt attagttgga atagtggtaa cataggttat   180
gcggactctg tgaagggccg attcaccatc tccagagaca cgccaagaa ctccctgttt   240 ctgctaatga acagtctgag acctgacgac tcggccttgt attactgtac aagaggatac   300
aactggaacg cgttatcccc tatggacgtc tggggccaag ggaccacggt caccgtctcc   360
tca   363

<210> SEQ ID NO 434
<211> LENGTH: 121
<212> TYPE: PRT
<213> ORGANISM: Artificial Sequence
<220> FEATURE:
<223> OTHER INFORMATION: Synthetic

<400> SEQUENCE: 434

Glu Met Gln Leu Val Glu Ser Gly Gly Gly Leu Val Gln Pro Asp Arg
1               5                   10                  15

Ser Leu Arg Leu Ser Cys Ala Ala Ser Gly Phe Asn Phe Asp Asn Tyr
            20                  25                  30

Ala Ile His Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Leu Met Asn Ser Leu Arg Pro Asp Asp Ser Ala Leu Tyr Tyr Cys
                85                  90                  95

Thr Arg Gly Tyr Asn Trp Asn Ala Leu Ser Pro Met Asp Val Trp Gly
            100                 105                 110

Gln Gly Thr Thr Val Thr Val Ser Ser
        115                 120

<210> SEQ ID NO 435
<211> LENGTH: 24
<212> TYPE: DNA
<213> ORGANISM: Artificial Sequence
<220> FEATURE:

<223> OTHER INFORMATION: Synthetic

<400> SEQUENCE: 435
ggattcaact tgataatta tgcc                                    24

<210> SEQ ID NO 436
<211> LENGTH: 8
<212> TYPE: PRT
<213> ORGANISM: Artificial Sequence
<220> FEATURE:
<223> OTHER INFORMATION: Synthetic

<400> SEQUENCE: 436

Gly Phe Asn Phe Asp Asn Tyr Ala
1               5

<210> SEQ ID NO 437
<211> LENGTH: 24
<212> TYPE: DNA
<213> ORGANISM: Artificial Sequence
<220> FEATURE:
<223> OTHER INFORMATION: Synthetic

<400> SEQUENCE: 437
attagttgga atagtggtaa cata                                   24

<210> SEQ ID NO 438
<211> LENGTH: 8
<212> TYPE: PRT
<213> ORGANISM: Artificial Sequence
<220> FEATURE:
<223> OTHER INFORMATION: Synthetic

<400> SEQUENCE: 438

Ile Ser Trp Asn Ser Gly Asn Ile
1               5

<210> SEQ ID NO 439
<211> LENGTH: 42
<212> TYPE: DNA
<213> ORGANISM: Artificial Sequence
<220> FEATURE:
<223> OTHER INFORMATION: Synthetic

<400> SEQUENCE: 439
acaagaggat acaactggaa cgcgttatcc cctatggacg tc               42

<210> SEQ ID NO 440
<211> LENGTH: 14
<212> TYPE: PRT
<213> ORGANISM: Artificial Sequence
<220> FEATURE:
<223> OTHER INFORMATION: Synthetic

<400> SEQUENCE: 440

Thr Arg Gly Tyr Asn Trp Asn Ala Leu Ser Pro Met Asp Val
1               5                   10

<210> SEQ ID NO 441
<211> LENGTH: 321
<212> TYPE: DNA
<213> ORGANISM: Artificial Sequence
<220> FEATURE:
<223> OTHER INFORMATION: Synthetic

<400> SEQUENCE: 441

```
gacatccaaa tgacccagtc tccatcctcc ctgtctgcat ctgtagggga cagagtcacc      60
gtcacttgcc gggcgagtca gggcattagc aattatttag cctggtatca gcaaaaacct     120
ggtaaagttc ctaaactcct gatctatgct gcatccactt tgcaatcagg ggtcccatct     180
cggttcagtg gcagtggatc tgggacagat ttcactctca ccatcagcag cctgcagcct     240
gaagatgttg caagttatta ctgtcaaaac tataacagtg cccctatgac gttcggccaa     300
gggaccaagg tggaaatcaa a                                                321
```

<210> SEQ ID NO 442
<211> LENGTH: 107
<212> TYPE: PRT
<213> ORGANISM: Artificial Sequence
<220> FEATURE:
<223> OTHER INFORMATION: Synthetic

<400> SEQUENCE: 442

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Ser Tyr Tyr Cys Gln Asn Tyr Asn Ser Ala Pro Met
                85                  90                  95

Thr Phe Gly Gln Gly Thr Lys Val Glu Ile Lys
            100                 105

<210> SEQ ID NO 443
<211> LENGTH: 18
<212> TYPE: DNA
<213> ORGANISM: Artificial Sequence
<220> FEATURE:
<223> OTHER INFORMATION: Synthetic

<400> SEQUENCE: 443
cagggcatta gcaattat                                                     18

<210> SEQ ID NO 444
<211> LENGTH: 6
<212> TYPE: PRT
<213> ORGANISM: Artificial Sequence
<220> FEATURE:
<223> OTHER INFORMATION: Synthetic

<400> SEQUENCE: 444

Gln Gly Ile Ser Asn Tyr
1               5

<210> SEQ ID NO 445
<211> LENGTH: 9
<212> TYPE: DNA
<213> ORGANISM: Artificial Sequence
<220> FEATURE:
<223> OTHER INFORMATION: Synthetic

<400> SEQUENCE: 445 gctgcatcc                                                                9

<210> SEQ ID NO 446
<211> LENGTH: 3
<212> TYPE: PRT
<213> ORGANISM: Artificial Sequence
<220> FEATURE:
<223> OTHER INFORMATION: Synthetic

<400> SEQUENCE: 446

Ala Ala Ser
1

<210> SEQ ID NO 447
<211> LENGTH: 27
<212> TYPE: DNA
<213> ORGANISM: Artificial Sequence
<220> FEATURE:
<223> OTHER INFORMATION: Synthetic

<400> SEQUENCE: 447
caaaactata acagtgcccc tatgacg                                      27

<210> SEQ ID NO 448
<211> LENGTH: 9
<212> TYPE: PRT
<213> ORGANISM: Artificial Sequence
<220> FEATURE:
<223> OTHER INFORMATION: Synthetic

<400> SEQUENCE: 448

Gln Asn Tyr Asn Ser Ala Pro Met Thr
1               5

<210> SEQ ID NO 449
<211> LENGTH: 366
<212> TYPE: DNA
<213> ORGANISM: Artificial Sequence
<220> FEATURE:
<223> OTHER INFORMATION: Synthetic

<400> SEQUENCE: 449
caggtgcagc tacaacagtg ggacgcagga ctgttgaagc cttcggagac cctgtccctc      60
acctgcgctg tctatggtgg gtccttcagt tcttactact ggagctggat ccgccagccc     120
ccagggaagg ggctggaatg gattgggaaa tcaatcatc gtggaagcac caactacaac      180
ccgtccctca gagtcgagt caccatctca gtagacacgt ccaagaacca gttctcccta     240
aagctgaggt ctgtgaccgc cgcggacacg gctgtgtatt actgtgcgcg agggggggta     300
gcagctcgtc cggactggca cttctttgac tactggggcc agggaaccct ggtcaccgtc     360
tcctca                                                              366

<210> SEQ ID NO 450
<211> LENGTH: 122
<212> TYPE: PRT
<213> ORGANISM: Artificial Sequence
<220> FEATURE:
<223> OTHER INFORMATION: Synthetic

<400> SEQUENCE: 450

Gln Val Gln Leu Gln Gln Trp Asp Ala Gly Leu Leu Lys Pro Ser Glu
1               5                   10                  15

Thr Leu Ser Leu Thr Cys Ala Val Tyr Gly Gly Ser Phe Ser Ser Tyr
            20                  25                  30

Tyr Trp Ser Trp Ile Arg Gln Pro Gly Lys Gly Leu Glu Trp Ile
            35                  40                  45

Gly Glu Ile Asn His Arg Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95

Arg Gly Gly Val Ala Ala Arg Pro Asp Trp His Phe Phe Asp Tyr Trp
             100                 105                 110

Gly Gln Gly Thr Leu Val Thr Val Ser Ser
            115                 120

<210> SEQ ID NO 451
<211> LENGTH: 24
<212> TYPE: DNA
<213> ORGANISM: Artificial Sequence
<220> FEATURE:
<223> OTHER INFORMATION: Synthetic

<400> SEQUENCE: 451
ggtgggtcct tcagttctta ctac                                              24

<210> SEQ ID NO 452
<211> LENGTH: 8
<212> TYPE: PRT
<213> ORGANISM: Artificial Sequence
<220> FEATURE:
<223> OTHER INFORMATION: Synthetic

<400> SEQUENCE: 452

Gly Gly Ser Phe Ser Ser Tyr Tyr
 1               5

<210> SEQ ID NO 453
<211> LENGTH: 21
<212> TYPE: DNA
<213> ORGANISM: Artificial Sequence
<220> FEATURE:
<223> OTHER INFORMATION: Synthetic

<400> SEQUENCE: 453
atcaatcatc gtggaagcac c                                                 21

<210> SEQ ID NO 454
<211> LENGTH: 7
<212> TYPE: PRT
<213> ORGANISM: Artificial Sequence
<220> FEATURE:
<223> OTHER INFORMATION: Synthetic

<400> SEQUENCE: 454

Ile Asn His Arg Gly Ser Thr
 1               5

<210> SEQ ID NO 455
<211> LENGTH: 48
<212> TYPE: DNA
<213> ORGANISM: Artificial Sequence
<220> FEATURE:
<223> OTHER INFORMATION: Synthetic

<400> SEQUENCE: 455
gcgcgagggg gggtagcagc tcgtccggac tggcacttct ttgactac                    48

<210> SEQ ID NO 456
<211> LENGTH: 16
<212> TYPE: PRT
<213> ORGANISM: Artificial Sequence
<220> FEATURE:
<223> OTHER INFORMATION: Synthetic

<400> SEQUENCE: 456

Ala Arg Gly Gly Val Ala Ala Arg Pro Asp Trp His Phe Phe Asp Tyr
1               5                   10                  15

<210> SEQ ID NO 457
<211> LENGTH: 321
<212> TYPE: DNA
<213> ORGANISM: Artificial Sequence
<220> FEATURE:
<223> OTHER INFORMATION: Synthetic

<400> SEQUENCE: 457
gacatccaga tgacccagtc tccatcctcc ctctctgcct ctgtaggaga cagagtcacc      60
atcacttgcc gggcaagtca ggtcattcga aatgatttag ctggtttca gcagagacca     120 gggaaagccc ctaagcgcct gatctatgct gcatccagtt tacaaagtga ggtcccatca    180
agattcagcg gcagtggatc tgggacagaa ttcactctca caatcaccag cctgcagcct    240
gaagattttg caacttatta ctgtcttcag cataatagtt acccgctcac cttcggccaa    300
gggacacgac tggagattaa a                                              321

<210> SEQ ID NO 458
<211> LENGTH: 107
<212> TYPE: PRT
<213> ORGANISM: Artificial Sequence
<220> FEATURE:
<223> OTHER INFORMATION: Synthetic

<400> SEQUENCE: 458

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Arg Asn Asp
                20                  25                  30

Leu Gly Trp Phe Gln Gln Arg Pro Gly Lys Ala Pro Lys Arg Leu Ile
        35                  40                  45

Tyr Ala Ala Ser Ser Leu Gln Ser Glu Val Pro Ser Arg Phe Ser Gly
    50                  55                  60

Ser Gly Ser Gly Thr Glu Phe Thr Leu Thr Ile Thr Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gln Gly Thr Arg Leu Glu Ile Lys
            100                 105

<210> SEQ ID NO 459
<211> LENGTH: 18
<212> TYPE: DNA
<213> ORGANISM: Artificial Sequence
<220> FEATURE:
<223> OTHER INFORMATION: Synthetic

<400> SEQUENCE: 459
caggtcattc gaaatgat                                                   18

<210> SEQ ID NO 460
<211> LENGTH: 6
<212> TYPE: PRT
<213> ORGANISM: Artificial Sequence
<220> FEATURE:
<223> OTHER INFORMATION: Synthetic

<400> SEQUENCE: 460

Gln Val Ile Arg Asn Asp
1               5

<210> SEQ ID NO 461
<211> LENGTH: 9
<212> TYPE: DNA
<213> ORGANISM: Artificial Sequence
<220> FEATURE:
<223> OTHER INFORMATION: Synthetic

<400> SEQUENCE: 461 gctgcatcc                                                            9

<210> SEQ ID NO 462
<211> LENGTH: 3
<212> TYPE: PRT
<213> ORGANISM: Artificial Sequence
<220> FEATURE:
<223> OTHER INFORMATION: Synthetic

<400> SEQUENCE: 462

Ala Ala Ser
1

<210> SEQ ID NO 463
<211> LENGTH: 27
<212> TYPE: DNA
<213> ORGANISM: Artificial Sequence
<220> FEATURE:
<223> OTHER INFORMATION: Synthetic

<400> SEQUENCE: 463
cttcagcata atagttaccc gctcacc                                       27

<210> SEQ ID NO 464
<211> LENGTH: 9
<212> TYPE: PRT
<213> ORGANISM: Artificial Sequence
<220> FEATURE:
<223> OTHER INFORMATION: Synthetic

<400> SEQUENCE: 464

Leu Gln His Asn Ser Tyr Pro Leu Thr
1               5

<210> SEQ ID NO 465
<211> LENGTH: 357
<212> TYPE: DNA
<213> ORGANISM: Artificial Sequence
<220> FEATURE:
<223> OTHER INFORMATION: Synthetic

<400> SEQUENCE: 465
gaggtgcagc tggtggagtc tgggggaggt gtggtacggc ctgggggggtc cctgagactc     60 tcctgtgcag cctctggatt cacctttgat gattatggca tgagctgggt ccgccaagtt    120
ccagggaagg ggctggagtg ggtctctggt cttaattgga atggtggaat cacaggttat    180

```
acagactctg tgaagggccg attcaccatc tccagagaca acgccaagaa ctccctgtat    240
ctgcaaatga acagtctgag agccgaggac acggccttct atcactgtgc gcgagatagt    300
ggggatcagg atgcttttga tatatggggc caggggacaa tggtcaccgt ctcctca      357
```

<210> SEQ ID NO 466
<211> LENGTH: 119
<212> TYPE: PRT
<213> ORGANISM: Artificial Sequence
<220> FEATURE:
<223> OTHER INFORMATION: Synthetic

<400> SEQUENCE: 466

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Val Pro Gly Lys Gly Leu Glu Trp Val
        35                  40                  45

Ser Gly Leu Asn Trp Asn Gly Gly Ile Thr Gly Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Phe Tyr His Cys
                85                  90                  95

Ala Arg Asp Ser Gly Asp Gln Asp Ala Phe Asp Ile Trp Gly Gln Gly
            100                 105                 110

Thr Met Val Thr Val Ser Ser
        115
```

<210> SEQ ID NO 467
<211> LENGTH: 24
<212> TYPE: DNA
<213> ORGANISM: Artificial Sequence
<220> FEATURE:
<223> OTHER INFORMATION: Synthetic

<400> SEQUENCE: 467

```
ggattcacct ttgatgatta tggc                                           24
```

<210> SEQ ID NO 468
<211> LENGTH: 8
<212> TYPE: PRT
<213> ORGANISM: Artificial Sequence
<220> FEATURE:
<223> OTHER INFORMATION: Synthetic

<400> SEQUENCE: 468

```
Gly Phe Thr Phe Asp Asp Tyr Gly
1               5
```

<210> SEQ ID NO 469
<211> LENGTH: 24
<212> TYPE: DNA
<213> ORGANISM: Artificial Sequence
<220> FEATURE:
<223> OTHER INFORMATION: Synthetic

<400> SEQUENCE: 469

```
cttaattgga atggtggaat caca                                           24
```

<210> SEQ ID NO 470

```
<211> LENGTH: 8
<212> TYPE: PRT
<213> ORGANISM: Artificial Sequence
<220> FEATURE:
<223> OTHER INFORMATION: Synthetic

<400> SEQUENCE: 470

Leu Asn Trp Asn Gly Gly Ile Thr
1               5

<210> SEQ ID NO 471
<211> LENGTH: 36
<212> TYPE: DNA
<213> ORGANISM: Artificial Sequence
<220> FEATURE:
<223> OTHER INFORMATION: Synthetic

<400> SEQUENCE: 471
gcgcgagata gtggggatca ggatgctttt gatata                        36

<210> SEQ ID NO 472
<211> LENGTH: 12
<212> TYPE: PRT
<213> ORGANISM: Artificial Sequence
<220> FEATURE:
<223> OTHER INFORMATION: Synthetic

<400> SEQUENCE: 472

Ala Arg Asp Ser Gly Asp Gln Asp Ala Phe Asp Ile
1               5                   10

<210> SEQ ID NO 473
<211> LENGTH: 318
<212> TYPE: DNA
<213> ORGANISM: Artificial Sequence
<220> FEATURE:
<223> OTHER INFORMATION: Synthetic

<400> SEQUENCE: 473
caaatagtga tgacgcagtc tccagccacc ctgtctgtat ctccagggga aagagccacc    60
ctctcctgca gggccagtca gagtattact ccctacttag cctggtacca gcaaaaacct   120
ggccagactc ccaggctcct catctatggt gtatccaccc gggccactgg tatcccagcc   180
aggttcagtg gcagtgggtc tgggacagag ttcactctca ccatcagcag cctgcagtct   240
gaagattttg cagtttatta ctgtcagcag tatgacaact ggtatacttt tggccagggg   300
accaagctgg agatcaaa                                                 318

<210> SEQ ID NO 474
<211> LENGTH: 106
<212> TYPE: PRT
<213> ORGANISM: Artificial Sequence
<220> FEATURE:
<223> OTHER INFORMATION: Synthetic

<400> SEQUENCE: 474

Gln Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Thr Pro Tyr
            20                  25                  30

Leu Ala Trp Tyr Gln Gln Lys Pro Gly Gln Thr Pro Arg Leu Leu Ile
        35                  40                  45

Tyr Gly Val Ser Thr Arg Ala Thr Gly Ile Pro Ala Arg Phe Ser Gly
    50                  55                  60
```

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asn Trp Tyr Thr
                85                  90                  95

Phe Gly Gln Gly Thr Lys Leu Glu Ile Lys
            100                 105

<210> SEQ ID NO 475
<211> LENGTH: 18
<212> TYPE: DNA
<213> ORGANISM: Artificial Sequence
<220> FEATURE:
<223> OTHER INFORMATION: Synthetic

<400> SEQUENCE: 475
cagagtatta ctccctac                                                     18

<210> SEQ ID NO 476
<211> LENGTH: 6
<212> TYPE: PRT
<213> ORGANISM: Artificial Sequence
<220> FEATURE:
<223> OTHER INFORMATION: Synthetic

<400> SEQUENCE: 476

Gln Ser Ile Thr Pro Tyr
1               5

<210> SEQ ID NO 477
<211> LENGTH: 9
<212> TYPE: DNA
<213> ORGANISM: Artificial Sequence
<220> FEATURE:
<223> OTHER INFORMATION: Synthetic

<400> SEQUENCE: 477 ggtgtatcc                                                                9

<210> SEQ ID NO 478
<211> LENGTH: 3
<212> TYPE: PRT
<213> ORGANISM: Artificial Sequence
<220> FEATURE:
<223> OTHER INFORMATION: Synthetic

<400> SEQUENCE: 478

Gly Val Ser
1

<210> SEQ ID NO 479
<211> LENGTH: 24
<212> TYPE: DNA
<213> ORGANISM: Artificial Sequence
<220> FEATURE:
<223> OTHER INFORMATION: Synthetic

<400> SEQUENCE: 479
cagcagtatg acaactggta tact                                              24

<210> SEQ ID NO 480
<211> LENGTH: 8
<212> TYPE: PRT
<213> ORGANISM: Artificial Sequence
<220> FEATURE:
<223> OTHER INFORMATION: Synthetic

<400> SEQUENCE: 480

Gln Gln Tyr Asp Asn Trp Tyr Thr
1               5

<210> SEQ ID NO 481
<211> LENGTH: 366
<212> TYPE: DNA
<213> ORGANISM: Artificial Sequence
<220> FEATURE:
<223> OTHER INFORMATION: Synthetic

<400> SEQUENCE: 481

```
caggtgcagg tggtggagtc tgggggaggc gtggtccagc ctggagggtc cctgagactc      60
tcctgtgcgg cctctggatt caccttcagt gactatggca tgcactgggt ccgccaggct     120
ccaggcaagg ggctggagtg ggtggcaatt atatcatatg atggaagtaa taaatactat     180
gcagactccg tgaagggccg attcaccgtg tccagagaca attccaagaa cactctgtat     240
ctgcaattgg acagcctgag acctgaggac gcggctgtct tttactgtgc gagagagggg     300
gcatttaact tagactacta cgccatggac gtctggggcc aagggacaac ggtcaccgtc     360
tcctca                                                                366
```

<210> SEQ ID NO 482
<211> LENGTH: 122
<212> TYPE: PRT
<213> ORGANISM: Artificial Sequence
<220> FEATURE:
<223> OTHER INFORMATION: Synthetic

<400> SEQUENCE: 482

Gln Val Gln Val Val Glu Ser Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Ile Ile Ser Tyr Asp Gly Ser Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Leu Asp Ser Leu Arg Pro Glu Asp Ala Ala Val Phe Tyr Cys
                85                  90                  95

Ala Arg Glu Gly Ala Phe Asn Leu Asp Tyr Tyr Ala Met Asp Val Trp
            100                 105                 110

Gly Gln Gly Thr Thr Val Thr Val Ser Ser
        115                 120

<210> SEQ ID NO 483
<211> LENGTH: 24
<212> TYPE: DNA
<213> ORGANISM: Artificial Sequence
<220> FEATURE:
<223> OTHER INFORMATION: Synthetic

<400> SEQUENCE: 483

```
ggattcacct tcagtgacta tggc                                             24
```

<210> SEQ ID NO 484
<211> LENGTH: 8

```
<212> TYPE: PRT
<213> ORGANISM: Artificial Sequence
<220> FEATURE:
<223> OTHER INFORMATION: Synthetic

<400> SEQUENCE: 484

Gly Phe Thr Phe Ser Asp Tyr Gly
1               5

<210> SEQ ID NO 485
<211> LENGTH: 24
<212> TYPE: DNA
<213> ORGANISM: Artificial Sequence
<220> FEATURE:
<223> OTHER INFORMATION: Synthetic

<400> SEQUENCE: 485
atatcatatg atggaagtaa taaa                                              24

<210> SEQ ID NO 486
<211> LENGTH: 8
<212> TYPE: PRT
<213> ORGANISM: Artificial Sequence
<220> FEATURE:
<223> OTHER INFORMATION: Synthetic

<400> SEQUENCE: 486

Ile Ser Tyr Asp Gly Ser Asn Lys
1               5

<210> SEQ ID NO 487
<211> LENGTH: 45
<212> TYPE: DNA
<213> ORGANISM: Artificial Sequence
<220> FEATURE:
<223> OTHER INFORMATION: Synthetic

<400> SEQUENCE: 487
gcgagagagg gggcatttaa cttagactac tacgccatgg acgtc                       45

<210> SEQ ID NO 488
<211> LENGTH: 15
<212> TYPE: PRT
<213> ORGANISM: Artificial Sequence
<220> FEATURE:
<223> OTHER INFORMATION: Synthetic

<400> SEQUENCE: 488

Ala Arg Glu Gly Ala Phe Asn Leu Asp Tyr Tyr Ala Met Asp Val
1               5                   10                  15

<210> SEQ ID NO 489
<211> LENGTH: 321
<212> TYPE: DNA
<213> ORGANISM: Artificial Sequence
<220> FEATURE:
<223> OTHER INFORMATION: Synthetic

<400> SEQUENCE: 489
gccatccaga tgacccagtc tccatcctcc ctgtctgcct ctgtaggaga cagagtcacc       60
atcacttgcc gggcaagtca ggacattaga aatgatttag gttggtatca gcagaaacca      120
gggaaagccc ctaacctcct gatctatgct gcatccagtt tacaaagtgg ggtcccatca      180
aggttcagcg gcagtgggtc tggcacagat ttcactctca ccatcagcag cctgcagcct      240
gaagattttg caacttatta ctgtctacaa gattccaatt acccgctcac tttcggcgga      300
```

-continued gggaccaagg tggagatcaa g    321

<210> SEQ ID NO 490
<211> LENGTH: 107
<212> TYPE: PRT
<213> ORGANISM: Artificial Sequence
<220> FEATURE:
<223> OTHER INFORMATION: Synthetic

<400> SEQUENCE: 490

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Lys Val Glu Ile Lys
            100                 105

<210> SEQ ID NO 491
<211> LENGTH: 18
<212> TYPE: DNA
<213> ORGANISM: Artificial Sequence
<220> FEATURE:
<223> OTHER INFORMATION: Synthetic

<400> SEQUENCE: 491
caggacatta gaaatgat    18

<210> SEQ ID NO 492
<211> LENGTH: 6
<212> TYPE: PRT
<213> ORGANISM: Artificial Sequence
<220> FEATURE:
<223> OTHER INFORMATION: Synthetic

<400> SEQUENCE: 492

Gln Asp Ile Arg Asn Asp
1               5

<210> SEQ ID NO 493
<211> LENGTH: 9
<212> TYPE: DNA
<213> ORGANISM: Artificial Sequence
<220> FEATURE:
<223> OTHER INFORMATION: Synthetic

<400> SEQUENCE: 493 gctgcatcc    9

<210> SEQ ID NO 494
<211> LENGTH: 3
<212> TYPE: PRT
<213> ORGANISM: Artificial Sequence
<220> FEATURE:
<223> OTHER INFORMATION: Synthetic

<400> SEQUENCE: 494

Ala Ala Ser
1

<210> SEQ ID NO 495
<211> LENGTH: 27
<212> TYPE: DNA
<213> ORGANISM: Artificial Sequence
<220> FEATURE:
<223> OTHER INFORMATION: Synthetic

<400> SEQUENCE: 495
ctacaagatt ccaattaccc gctcact                                          27

<210> SEQ ID NO 496
<211> LENGTH: 9
<212> TYPE: PRT
<213> ORGANISM: Artificial Sequence
<220> FEATURE:
<223> OTHER INFORMATION: Synthetic

<400> SEQUENCE: 496

Leu Gln Asp Ser Asn Tyr Pro Leu Thr
1               5

<210> SEQ ID NO 497
<211> LENGTH: 670
<212> TYPE: PRT
<213> ORGANISM: Artificial Sequence
<220> FEATURE:
<223> OTHER INFORMATION: Synthetic

<400> SEQUENCE: 497

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

```
His Asp Glu Cys Ala Gly Gly Cys Ser Gly Pro Gln Asp Thr Asp Cys
    210             215                 220
Phe Ala Cys Arg His Phe Asn Asp Ser Gly Ala Cys Val Pro Arg Cys
225             230                 235                 240
Pro Gln Pro Leu Val Tyr Asn Lys Leu Thr Phe Gln Leu Glu Pro Asn
                245                 250                 255
Pro His Thr Lys Tyr Gln Tyr Gly Gly Val Cys Val Ala Ser Cys Pro
            260                 265                 270
His Asn Phe Val Val Asp Gln Thr Ser Cys Val Arg Ala Cys Pro Pro
        275                 280                 285
Asp Lys Met Glu Val Asp Lys Asn Gly Leu Lys Met Cys Glu Pro Cys
    290                 295                 300
Gly Gly Leu Cys Pro Lys Ala Cys Glu Gly Thr Gly Ser Gly Ser Arg
305             310                 315                 320
Phe Gln Thr Val Asp Ser Ser Asn Ile Asp Gly Phe Val Asn Cys Thr
                325                 330                 335
Lys Ile Leu Gly Asn Leu Asp Phe Leu Ile Thr Gly Leu Asn Gly Asp
            340                 345                 350
Pro Trp His Lys Ile Pro Ala Leu Asp Pro Glu Lys Leu Asn Val Phe
        355                 360                 365
Arg Thr Val Arg Glu Ile Thr Gly Tyr Leu Asn Ile Gln Ser Trp Pro
    370                 375                 380
Pro His Met His Asn Phe Ser Val Phe Ser Asn Leu Thr Thr Ile Gly
385             390                 395                 400
Gly Arg Ser Leu Tyr Asn Arg Gly Phe Ser Leu Leu Ile Met Lys Asn
                405                 410                 415
Leu Asn Val Thr Ser Leu Gly Phe Arg Ser Leu Lys Glu Ile Ser Ala
            420                 425                 430
Gly Arg Ile Tyr Ile Ser Ala Asn Arg Gln Leu Cys Tyr His His Ser
        435                 440                 445
Leu Asn Trp Thr Lys Val Leu Arg Gly Pro Thr Glu Glu Arg Leu Asp
    450                 455                 460
Ile Lys His Asn Arg Pro Arg Arg Asp Cys Val Ala Glu Gly Lys Val
465             470                 475                 480
Cys Asp Pro Leu Cys Ser Ser Gly Gly Cys Trp Gly Pro Gly Pro Gly
                485                 490                 495
Gln Cys Leu Ser Cys Arg Asn Tyr Ser Arg Gly Gly Val Cys Val Thr
            500                 505                 510
His Cys Asn Phe Leu Asn Gly Glu Pro Arg Glu Phe Ala His Glu Ala
        515                 520                 525
Glu Cys Phe Ser Cys His Pro Glu Cys Gln Pro Met Glu Gly Thr Ala
    530                 535                 540
Thr Cys Asn Gly Ser Gly Ser Asp Thr Cys Ala Gln Cys Ala His Phe
545             550                 555                 560
Arg Asp Gly Pro His Cys Val Ser Ser Cys Pro His Gly Val Leu Gly
                565                 570                 575
Ala Lys Gly Pro Ile Tyr Lys Tyr Pro Asp Val Gln Asn Glu Cys Arg
            580                 585                 590
Pro Cys His Glu Asn Cys Thr Gln Gly Cys Lys Gly Pro Glu Leu Gln
        595                 600                 605
Asp Cys Leu Gly Gln Gly Thr Lys Thr His Leu Arg Arg Gly Ser Gly
    610                 615                 620
Trp Arg Thr Lys Thr His Leu Arg Arg Gly Ser Ala Pro Ser Pro Ser
```

```
                625                 630                 635                 640
Pro Leu Glu Gln Lys Leu Ile Ser Glu Glu Asp Leu Gly Gly Glu Gln
                    645                 650                 655
Lys Leu Ile Ser Glu Glu Asp Leu His His His His His His
                    660                 665                 670

<210> SEQ ID NO 498
<211> LENGTH: 840
<212> TYPE: PRT
<213> ORGANISM: Artificial Sequence
<220> FEATURE:
<223> OTHER INFORMATION: Synthetic

<400> SEQUENCE: 498

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
                20                  25                  30

Leu Tyr Glu Arg Cys Glu Val Val Met Gly Asn Leu Glu Ile Val Leu
            35                  40                  45

Thr Gly His Asn Ala Asp Leu Ser Phe Leu Gln Trp Ile Arg Glu Val
        50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
```

```
                   325                 330                 335
    Lys Ile Leu Gly Asn Leu Asp Phe Leu Ile Thr Gly Leu Asn Gly Asp
                   340                 345                 350
    Pro Trp His Lys Ile Pro Ala Leu Asp Pro Glu Lys Leu Asn Val Phe
                   355                 360                 365
    Arg Thr Val Arg Glu Ile Thr Gly Tyr Leu Asn Ile Gln Ser Trp Pro
                   370                 375                 380
    Pro His Met His Asn Phe Ser Val Phe Ser Asn Leu Thr Thr Ile Gly
    385                 390                 395                 400
    Gly Arg Ser Leu Tyr Asn Arg Gly Phe Ser Leu Leu Ile Met Lys Asn
                   405                 410                 415
    Leu Asn Val Thr Ser Leu Gly Phe Arg Ser Leu Lys Glu Ile Ser Ala
                   420                 425                 430
    Gly Arg Ile Tyr Ile Ser Ala Asn Arg Gln Leu Cys Tyr His His Ser
                   435                 440                 445
    Leu Asn Trp Thr Lys Val Leu Arg Gly Pro Thr Glu Glu Arg Leu Asp
                   450                 455                 460
    Ile Lys His Asn Arg Pro Arg Arg Asp Cys Val Ala Glu Gly Lys Val
    465                 470                 475                 480
    Cys Asp Pro Leu Cys Ser Ser Gly Gly Cys Trp Gly Pro Gly Pro Gly
                   485                 490                 495
    Gln Cys Leu Ser Cys Arg Asn Tyr Ser Arg Gly Gly Val Cys Val Thr
                   500                 505                 510
    His Cys Asn Phe Leu Asn Gly Glu Pro Arg Glu Phe Ala His Glu Ala
                   515                 520                 525
    Glu Cys Phe Ser Cys His Pro Glu Cys Gln Pro Met Glu Gly Thr Ala
                   530                 535                 540
    Thr Cys Asn Gly Ser Gly Ser Asp Thr Cys Ala Gln Cys Ala His Phe
    545                 550                 555                 560
    Arg Asp Gly Pro His Cys Val Ser Ser Cys Pro His Gly Val Leu Gly
                   565                 570                 575
    Ala Lys Gly Pro Ile Tyr Lys Tyr Pro Asp Val Gln Asn Glu Cys Arg
                   580                 585                 590
    Pro Cys His Glu Asn Cys Thr Gln Gly Cys Lys Gly Pro Glu Leu Gln
                   595                 600                 605
    Asp Cys Leu Gly Gln Asp Lys Thr His Thr Cys Pro Pro Cys Pro Ala
                   610                 615                 620
    Pro Glu Leu Leu Gly Gly Pro Ser Val Phe Leu Phe Pro Pro Lys Pro
    625                 630                 635                 640
    Lys Asp Thr Leu Met Ile Ser Arg Thr Pro Glu Val Thr Cys Val Val
                   645                 650                 655
    Val Asp Val Ser His Glu Asp Pro Glu Val Lys Phe Asn Trp Tyr Val
                   660                 665                 670
    Asp Gly Val Glu Val His Asn Ala Lys Thr Lys Pro Arg Glu Glu Gln
                   675                 680                 685
    Tyr Asn Ser Thr Tyr Arg Val Val Ser Val Leu Thr Val Leu His Gln
                   690                 695                 700
    Asp Trp Leu Asn Gly Lys Glu Tyr Lys Cys Lys Val Ser Asn Lys Ala
    705                 710                 715                 720
    Leu Pro Ala Pro Ile Glu Lys Thr Ile Ser Lys Ala Lys Gly Gln Pro
                   725                 730                 735
    Arg Glu Pro Gln Val Tyr Thr Leu Pro Pro Ser Arg Asp Glu Leu Thr
                   740                 745                 750
```

Lys Asn Gln Val Ser Leu Thr Cys Leu Val Lys Gly Phe Tyr Pro Ser
            755                 760                 765

Asp Ile Ala Val Glu Trp Glu Ser Asn Gly Gln Pro Glu Asn Asn Tyr
    770                 775                 780

Lys Thr Thr Pro Pro Val Leu Asp Ser Asp Gly Ser Phe Phe Leu Tyr
785                 790                 795                 800

Ser Lys Leu Thr Val Asp Lys Ser Arg Trp Gln Gln Gly Asn Val Phe
                805                 810                 815

Ser Cys Ser Val Met His Glu Ala Leu His Asn His Tyr Thr Gln Lys
            820                 825                 830

Ser Leu Ser Leu Ser Pro Gly Lys
            835                 840

<210> SEQ ID NO 499
<211> LENGTH: 846
<212> TYPE: PRT
<213> ORGANISM: Artificial Sequence
<220> FEATURE:
<223> OTHER INFORMATION: Synthetic

<400> SEQUENCE: 499

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

```
His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
                355                 360                 365

Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
            435                 440                 445

Leu Asn Trp Thr Lys Val Leu Arg Gly Pro Thr Glu Glu Arg Leu Asp
        450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
                500                 505                 510

His Cys Asn Phe Leu Asn Gly Glu Pro Arg Glu Phe Ala His Glu Ala
        515                 520                 525

Glu Cys Phe Ser Cys His Pro Glu Cys Gln Pro Met Glu Gly Thr Ala
    530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
                580                 585                 590

Pro Cys His Glu Asn Cys Thr Gln Gly Cys Lys Gly Pro Glu Leu Gln
            595                 600                 605

Asp Cys Leu Gly Gln Glu Pro Arg Gly Pro Thr Ile Lys Pro Cys Pro
    610                 615                 620

Pro Cys Lys Cys Pro Ala Pro Asn Leu Leu Gly Pro Ser Val Phe
625                 630                 635                 640

Ile Phe Pro Pro Lys Ile Lys Asp Val Leu Met Ile Ser Leu Ser Pro
                645                 650                 655

Ile Val Thr Cys Val Val Asp Val Ser Glu Asp Pro Asp Val
            660                 665                 670

Gln Ile Ser Trp Phe Val Asn Asn Val Glu Val His Thr Ala Gln Thr
        675                 680                 685
```

-continued

```
Gln Thr His Arg Glu Asp Tyr Asn Ser Thr Leu Arg Val Val Ser Ala
    690                 695                 700
Leu Pro Ile Gln His Gln Asp Trp Met Ser Gly Lys Glu Phe Lys Cys
705                 710                 715                 720
Lys Val Asn Asn Lys Asp Leu Pro Ala Pro Ile Glu Arg Thr Ile Ser
                725                 730                 735
Lys Pro Lys Gly Ser Val Arg Ala Pro Gln Val Tyr Val Leu Pro Pro
            740                 745                 750
Pro Glu Glu Glu Met Thr Lys Lys Gln Val Thr Leu Thr Cys Met Val
        755                 760                 765
Thr Asp Phe Met Pro Glu Asp Ile Tyr Val Glu Trp Thr Asn Asn Gly
    770                 775                 780
Lys Thr Glu Leu Asn Tyr Lys Asn Thr Glu Pro Val Leu Asp Ser Asp
785                 790                 795                 800
Gly Ser Tyr Phe Met Tyr Ser Lys Leu Arg Val Glu Lys Lys Asn Trp
                805                 810                 815
Val Glu Arg Asn Ser Tyr Ser Cys Ser Val Val His Glu Gly Leu His
            820                 825                 830
Asn His His Thr Thr Lys Ser Phe Ser Arg Thr Pro Gly Lys
        835                 840                 845

<210> SEQ ID NO 500
<211> LENGTH: 227
<212> TYPE: PRT
<213> ORGANISM: Artificial Sequence
<220> FEATURE:
<223> OTHER INFORMATION: Synthetic

<400> SEQUENCE: 500

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
```

```
-continued

His Glu Ala Leu His Asn His Tyr Thr Gln Lys Ser Leu Ser Leu Ser
    210                 215                 220

Pro Gly Lys
225
```